(12) United States Patent
Goble et al.

(10) Patent No.: US 7,867,280 B2
(45) Date of Patent: Jan. 11, 2011

(54) METHODS FOR MOUNTING AND USING TETHERED JOINT BEARING IMPLANTS

(75) Inventors: E. Marlowe Goble, Alta, WY (US); Robert A. Hodorek, Warsaw, IN (US); Daniel F. Justin, Logan, UT (US); Joel Dever, Providence, UT (US); Marc Yap, Millville, UT (US)

(73) Assignee: Zimmer, Inc., Warsaw, IN (US)

( * ) Notice: Subject to any disclaimer, the term of this patent is extended or adjusted under 35 U.S.C. 154(b) by 1190 days.

(21) Appl. No.: 10/901,935

(22) Filed: Jul. 28, 2004

(65) Prior Publication Data

US 2006/0009774 A1 Jan. 12, 2006

Related U.S. Application Data

(60) Provisional application No. 60/586,706, filed on Jul. 9, 2004.

(51) Int. Cl.
*A61F 2/38* (2006.01)
(52) U.S. Cl. .................. 623/20.32; 623/20.14; 606/304
(58) Field of Classification Search ................ 606/300, 606/301, 304, 321, 74, 80, 85, 96, 103, 104, 606/151; 623/20.15, 23.44, 20.3, 20.33, 623/20.34, 20.36, 23.27, 20.14, 20.32
See application file for complete search history.

(56) References Cited

U.S. PATENT DOCUMENTS

| | | | |
|---|---|---|---|
| 3,748,662 A | 7/1973 | Helfet | |
| 4,000,525 A | 1/1977 | Klawitter et al. | |
| 4,224,696 A | 9/1980 | Murray et al. | |
| 4,479,271 A | 10/1984 | Bolesky et al. | |
| 4,502,161 A | 3/1985 | Wall | |
| 4,627,853 A | 12/1986 | Campbell et al. | |
| 4,657,549 A | 4/1987 | Keller | |
| 4,673,407 A | 6/1987 | Martin | |
| 4,838,891 A | 6/1989 | Branemark et al. | |
| 4,919,671 A | 4/1990 | Karf | |
| 4,927,421 A | 5/1990 | Goble et al. | |

(Continued)

FOREIGN PATENT DOCUMENTS

DE 3 917 285 11/1990

(Continued)

OTHER PUBLICATIONS

Restriction Requirement mailed Jul. 2, 2007 in U.S. Appl. No. 10/935,941.

(Continued)

*Primary Examiner*—Eduardo C Robert
*Assistant Examiner*—David Comstock
(74) *Attorney, Agent, or Firm*—Baker & Daniels LLP

(57) ABSTRACT

A method includes the acts of sliding a first end of a flexible first line through a channel in a first bone anchor. A portion of the first line is connected to an implant having a top articular surface and an opposing bone apposition surface. The first line extending between the implant and the first bone anchor is then tensioned. While the tensioning force is maintained on the first line, the first line is secured to the first bone anchor.

27 Claims, 60 Drawing Sheets

U.S. PATENT DOCUMENTS

| | | | |
|---|---|---|---|
| 4,950,270 | A | 8/1990 | Bowman et al. |
| 4,963,153 | A | 10/1990 | Noesberger et al. |
| 4,964,868 | A | 10/1990 | Bloebaum |
| 5,019,103 | A | 5/1991 | Van Zile et al. |
| 5,035,699 | A | 7/1991 | Coates |
| 5,037,439 | A | 8/1991 | Albrektsson et al. |
| 5,092,895 | A | 3/1992 | Albrektsson et al. |
| 5,100,409 | A | 3/1992 | Coates et al. |
| 5,176,684 | A | 1/1993 | Ferrante et al. |
| 5,180,383 | A | 1/1993 | Haydon |
| 5,258,015 | A * | 11/1993 | Li et al. ............ 606/232 |
| 5,282,868 | A | 2/1994 | Bahler |
| 5,346,496 | A | 9/1994 | Penning |
| 5,474,559 | A | 12/1995 | Bertin et al. |
| 5,489,311 | A | 2/1996 | Cipolletti |
| 5,507,812 | A | 4/1996 | Moore |
| 5,549,683 | A | 8/1996 | Bonutti |
| 5,569,259 | A | 10/1996 | Ferrante et al. |
| 5,571,196 | A | 11/1996 | Stein |
| 5,571,203 | A | 11/1996 | Masini |
| 5,593,411 | A | 1/1997 | Stalcup et al. |
| 5,634,927 | A | 6/1997 | Houston et al. |
| 5,674,224 | A | 10/1997 | Howell et al. |
| 5,702,397 | A | 12/1997 | Goble et al. |
| 5,702,459 | A | 12/1997 | Hummer et al. |
| 5,709,689 | A | 1/1998 | Ferrante et al. |
| 5,741,262 | A | 4/1998 | Albrektsson et al. |
| 5,743,915 | A | 4/1998 | Bertin et al. |
| 5,746,771 | A * | 5/1998 | Clement et al. ......... 623/23.22 |
| 5,755,800 | A | 5/1998 | O'Neil et al. |
| 5,755,803 | A | 5/1998 | Haines et al. |
| 5,766,255 | A | 6/1998 | Slamin et al. |
| 5,769,855 | A | 6/1998 | Bertin et al. |
| 5,776,201 | A | 7/1998 | Colleran et al. |
| 5,782,924 | A | 7/1998 | Johnson |
| 5,800,553 | A | 9/1998 | Albrektsson et al. |
| 5,824,098 | A | 10/1998 | Stein |
| 5,860,981 | A | 1/1999 | Bertin et al. |
| 5,879,391 | A | 3/1999 | Slamin |
| 5,885,035 | A | 3/1999 | Hoffschneider |
| 5,968,045 | A | 10/1999 | Frazier |
| 6,068,648 | A | 5/2000 | Cole et al. |
| 6,071,311 | A | 6/2000 | O'Neil et al. |
| 6,102,954 | A | 8/2000 | Albrektsson et al. |
| 6,132,468 | A | 10/2000 | Mansmann |
| 6,162,234 | A | 12/2000 | Freedland et al. |
| 6,168,629 | B1 | 1/2001 | Timoteo |
| 6,171,342 | B1 | 1/2001 | O'Neil et al. |
| 6,245,110 | B1 | 6/2001 | Grundel et al. |
| 6,299,645 | B1 | 10/2001 | Ogden |
| 6,319,271 | B1 | 11/2001 | Schwartz et al. |
| 6,368,326 | B1 | 4/2002 | Dakin et al. |
| 6,436,101 | B1 | 8/2002 | Hamada |
| 6,461,373 | B2 | 10/2002 | Wyman et al. |
| 6,508,841 | B2 | 1/2003 | Martin et al. |
| 6,520,964 | B2 | 2/2003 | Tallarida et al. |
| 6,544,267 | B1 | 4/2003 | Cole et al. |
| 6,554,838 | B2 | 4/2003 | McGovern et al. |
| 6,610,067 | B2 | 8/2003 | Tallarida et al. |
| 6,652,587 | B2 | 11/2003 | Felt et al. |
| 6,679,917 | B2 | 1/2004 | Ek |
| 6,736,819 | B2 | 5/2004 | Tiirneni |
| 6,773,461 | B2 | 8/2004 | Meyers |
| 6,866,683 | B2 | 3/2005 | Gerbec et al. |
| 6,905,514 | B2 | 6/2005 | Carignan et al. |
| 6,969,393 | B2 | 11/2005 | Pinczewski et al. |
| 6,994,725 | B1 | 2/2006 | Goble |
| 7,150,761 | B2 | 12/2006 | Justin et al. |
| 7,250,061 | B2 | 7/2007 | Jacobsson et al. |
| 2002/0019637 | A1 | 2/2002 | Frey et al. |
| 2002/0055783 | A1 | 5/2002 | Tallarida et al. |
| 2002/0107520 | A1 * | 8/2002 | Hoffman ............ 606/72 |
| 2002/0138150 | A1 | 9/2002 | Leclercq |
| 2002/0147498 | A1 | 10/2002 | Tallarida et al. |
| 2002/0198528 | A1 | 12/2002 | Engh et al. |
| 2003/0033018 | A1 | 2/2003 | Merchant |
| 2003/0060887 | A1 | 3/2003 | Ek |
| 2003/0120276 | A1 | 6/2003 | Tallarida et al. |
| 2003/0158606 | A1 | 8/2003 | Coon et al. |
| 2003/0225456 | A1 | 12/2003 | Ek |
| 2003/0225457 | A1 | 12/2003 | Justin et al. |
| 2004/0015170 | A1 | 1/2004 | Tallarida et al. |
| 2004/0106928 | A1 | 6/2004 | Ek |
| 2004/0148030 | A1 | 7/2004 | Ek |
| 2005/0137708 | A1 | 6/2005 | Clark |
| 2005/0143831 | A1 | 6/2005 | Justin et al. |
| 2005/0149044 | A1 | 7/2005 | Justin et al. |
| 2005/0154398 | A1 | 7/2005 | Miniaci et al. |
| 2005/0177242 | A1 | 8/2005 | Lotke |
| 2006/0009853 | A1 | 1/2006 | Justin et al. |

FOREIGN PATENT DOCUMENTS

| | | |
|---|---|---|
| EP | 0 336 774 B1 | 10/1989 |
| EP | 0 714 645 B1 | 6/1996 |
| EP | 0 850 606 A2 | 7/1998 |
| EP | 0 980 679 A2 | 2/2000 |
| EP | 0 985 386 A2 | 3/2000 |
| FR | 2 521 421 | 11/1975 |
| FR | 2 630 639 | 3/1988 |
| FR | 2 682 589 | 4/1993 |
| FR | 2 718 953 | 10/1995 |
| GB | 2 007 980 A | 5/1979 |
| WO | WO 89/09578 A1 | 10/1989 |
| WO | WO 89/11837 | 12/1989 |
| WO | WO 91/06260 | 5/1991 |
| WO | WO 94/09723 | 5/1994 |
| WO | WO 01/28457 A1 | 4/2001 |
| WO | WO 01/66021 A1 | 9/2001 |
| WO | WO 01/66022 A1 | 9/2001 |
| WO | WO 03/051210 A2 | 6/2003 |
| WO | WO 03/051211 A1 | 6/2003 |
| WO | WO 03/099159 A2 | 12/2003 |
| WO | WO 2005/069809 A3 | 8/2005 |

OTHER PUBLICATIONS

Restriction Requirement mailed Jan. 24, 2008 in U.S. Appl. No. 10/935,941.

Office Action mailed Jul. 8, 2008 in U.S. Appl. No. 10/935,941.

Final Office Action mailed Jul. 21, 2009 in U.S. Appl. No. 10/935,941.

The Office Action mailed Apr. 9, 2009 in related Candian application No. 2,490,673.

The Response filed Oct. 8, 2009 to the Office Action mailed Apr. 9, 2009 in related Canadian application No. 2,490,673.

* cited by examiner

METHODS FOR MOUNTING AND USING TETHERED JOINT BEARING IMPLANTS

CROSS-REFERENCE TO RELATED APPLICATIONS

This application claims priority to U.S. Provisional Patent Application Ser. No. 60/586,706, filed Jul. 9, 2004, which is incorporated herein by specific reference.

BACKGROUND OF THE INVENTION

1. The Field of the Invention

The present invention relates to methods for mounting tethered implants on a natural or resected articulation surface of an orthopedic joint of a patient.

2. The Relevant Technology

The human body has a variety of movable orthopedic joints such as the knee joint, hip joint, shoulder joint, and the like. These joints are formed by the intersection of two bones. The intersecting end of each bone has smooth articular surface that is comprised of cartilage. As a result of injury, wear, arthritis, disease or other causes, it is occasionally necessary to replace all or part of an orthopedic joint with an artificial implant. This procedure is referred to as a joint replacement or arthroplasty. For example, a total knee arthroplasty comprises cutting off or resecting the articular surfaces at both the distal end of the femur and the proximal end of the tibia. Complementary artificial implants are then mounted on the distal end of the femur and the proximal end of the tibia. Where only a portion of a joint is damaged, a partial joint arthroplasty can be performed. In this procedure, one or more artificial implants replace only a portion of a joint.

Although joint replacement is now a common procedure that has met with popular success, conventional implants and related mounting techniques have significant shortcomings. One significant drawback of many joint replacements is the extended and painful patient recovery. For example, a traditional knee replacement requires an open procedure wherein a relatively large incision is made which severs a portion of the muscle bounding the femur. The large incision is made so as to fully expose the respective ends of the femur and tibia.

This exposure is necessary when using conventional techniques to resect the femur and tibia and to mount the implants. For example, some conventional tibial implants are screwed directly into the resected end face of the tibia. Mounting such screws requires exposure of the resected end face. In yet other embodiments, the implants are formed with posts projecting therefrom. The posts are received within sockets formed on the resected end face of the tibia and femur. Again, forming of the sockets and inserting the posts into the sockets requires substantially full exposure of the resected end face of the tibia and femur.

In general, the more invasive the surgery, the more painful, difficult, and time consuming the patient recovery. This is largely due to the significant amount of scar tissue produced by the incision and resection of various soft tissues. Furthermore, such open and invasive surgeries have a greater risk of infection.

Another problem with conventional joint implants and related techniques for mounting is that it can be difficult to fit, adjust, and/or exchange different implants during the fitting stage. That is, implants come in a variety of different sizes, shapes, and configurations. During the joint replacement procedure, the surgeon may often test a variety of different sized implants to determine the best fit and alignment. As conventional implants are screwed into or pounded onto the bone during placement, the fitting, adjustment, and/or replacement of different conventional implants can be difficult and potentially damaging to the bone. Likewise, it can often be difficult to replace worn or damaged implants.

Accordingly, what is needed are implants and related methods and systems for preparing an articular surface of a joint and mounting an implant thereat which minimizes the length of incision, the amount of bone resection, and/or the impact on soft tissue. What is also needed are implants and related methods and systems which enable easier fitting, alignment, testing and/or replacement of implants.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
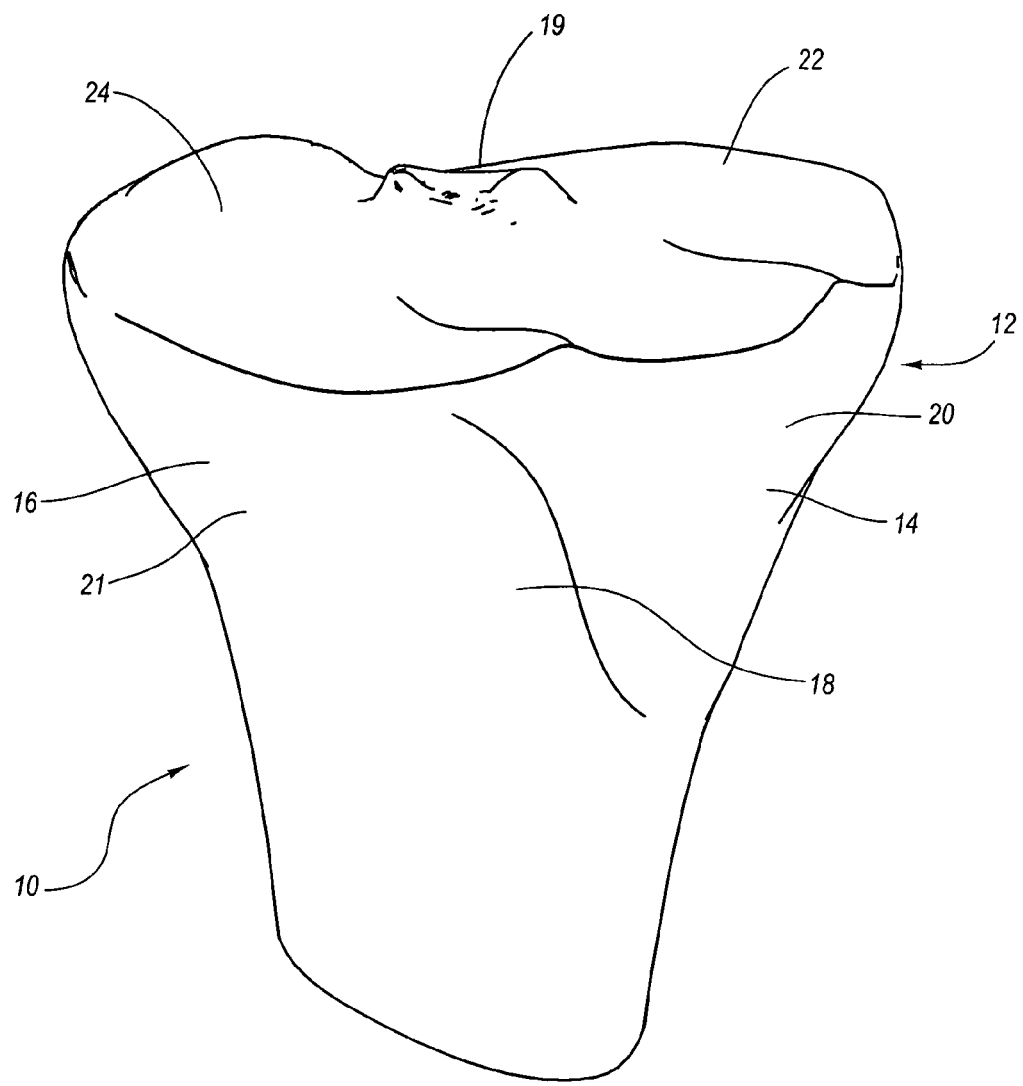
FIG. 1 is a perspective view of the proximal end of a tibia.

The present invention relates to methods and apparatus for preparing an articulation surface of an orthopedic joint to receive an implant, implants for mounting at an articulation surface of an orthopedic joint, anchoring systems for securing an implant at an articulation surface of an orthopedic joint, and related methods and instruments. As used in the specification and appended claims, the terms "articulation surface" and "natural articulation surface" are broadly intended to include all natural articular surfaces of a bone forming a portion of an orthopedic joint and all articulation wear surfaces of a bone forming a portion of an orthopedic joint which are produced as a result of ware, trauma, disease, or other causes which remove all or a portion of the natural articular surface.

The implants, anchoring systems, instruments, and methods of the present invention can be used in combination to mount an inventive implant or can be used separately or in combinations with other conventional implants, anchoring systems, instruments and/or methods. It is appreciated that the implants, anchoring systems, instruments, and methods of the present invention can be used for mounting an implant on virtually any articulation surface of any orthopedic joint in a human or other mammal. By way of example and not by limitation, the implants, anchoring systems, instruments, and methods of the present invention can be used in association with resurfacing an articulation surface of a knee joint, ankle joint, hip joint, shoulder joint, elbow joint, wrist joint, interphalangeal joint, or other joints. As such, the implants can be mounted on the proximal end and distal end of the femur, tibia, humerus, radius, and ulna, and on the articular surfaces of the scapula, pelvis, bones within the foot and hand, and other bone articular surfaces. Likewise, the implants, anchoring systems, instruments, and methods of the present invention can be used in facilitating a partial joint arthroplasty or a total joint arthroplasty.

In one embodiment, the implants, anchoring systems, instruments, and/or methods of the present invention are designed so that an articulation surface of a joint can be prepared and an implant mounted thereon using procedures that are minimally invasive. As a result, recovery time is significantly improved while the damage to soft tissue if decreased and the risk of infection minimized. Also in one embodiment of the present invention, the implants, anchoring systems, instruments, and/or methods are designed so that the implant can be selectively adjusted, tightened, and/or loosened after the implant is positioned on the articulation surface. This ability allows for greater ease in adjustment and fitting of an implant at the time of initial placement and for greater easy in replacement of an implant.

Set forth below are several embodiments of the present invention used in association with preparing an articulation surface at a proximal end of a tibia and mounting a condylar implant at the proximal end of the tibia. It is again noted that these embodiments are only given by way of example and that one skilled in the art based on the teaching provided herein would be able to use corresponding implants, methods, and instruments to prepare and/or mount an implant on other joint articulation surfaces.

Depicted in FIG. 1 is a proximal end 10 of a tibia 12. Proximal end 10 has a lateral side 14 and a medial side 16 which each extend between an anterior side 18 and a posterior side 19. Proximal end 10 further comprises a lateral condyle 20 and a medial condyle 21. Lateral condyle 20 terminates proximally at a lateral facet 22 of a superior articular surface of tibia 12 while medial condyle 21 terminates proximally at medial facet 24 of a superior articular surface of tibia 12.

Although tibia 12 shown in FIG. 1 is from a left leg, it is appreciated that the tibia of the right leg has a complimentary configuration and that the methods and apparatus of this specific example are equally applicable thereto. Furthermore, the methods and apparatus of this example are primarily illustrated in association with medial condyle 21 of tibia 12. It is also appreciated that the methods and apparatus can be used in association with lateral condyle 20.

In one embodiment, to facilitate mounting of a condylar implant on medial condyle 21, conventional arthroscopic procedures are used to resect the posterior portion of the medial meniscus. Once the posterior portion of the medial meniscus is removed, a vertical or horizontal incision, generally in a range between about 2 cm to about 6 cm, is formed over the anterior side of the medial meniscus. Following retraction of the surrounding tissue, the anterior side of the medial meniscus is resected. A coarse rasp is then inserted between the medial condyle of the femur and medial condyle 21 of tibia 12. The rasp is used to remove approximately 1-2 mm of articular cartilage on medial facet 24 of tibia 12. Removal of the meniscus and the articular cartilage provides increased access to medial facet 24 of tibia 12.

Figure 2:
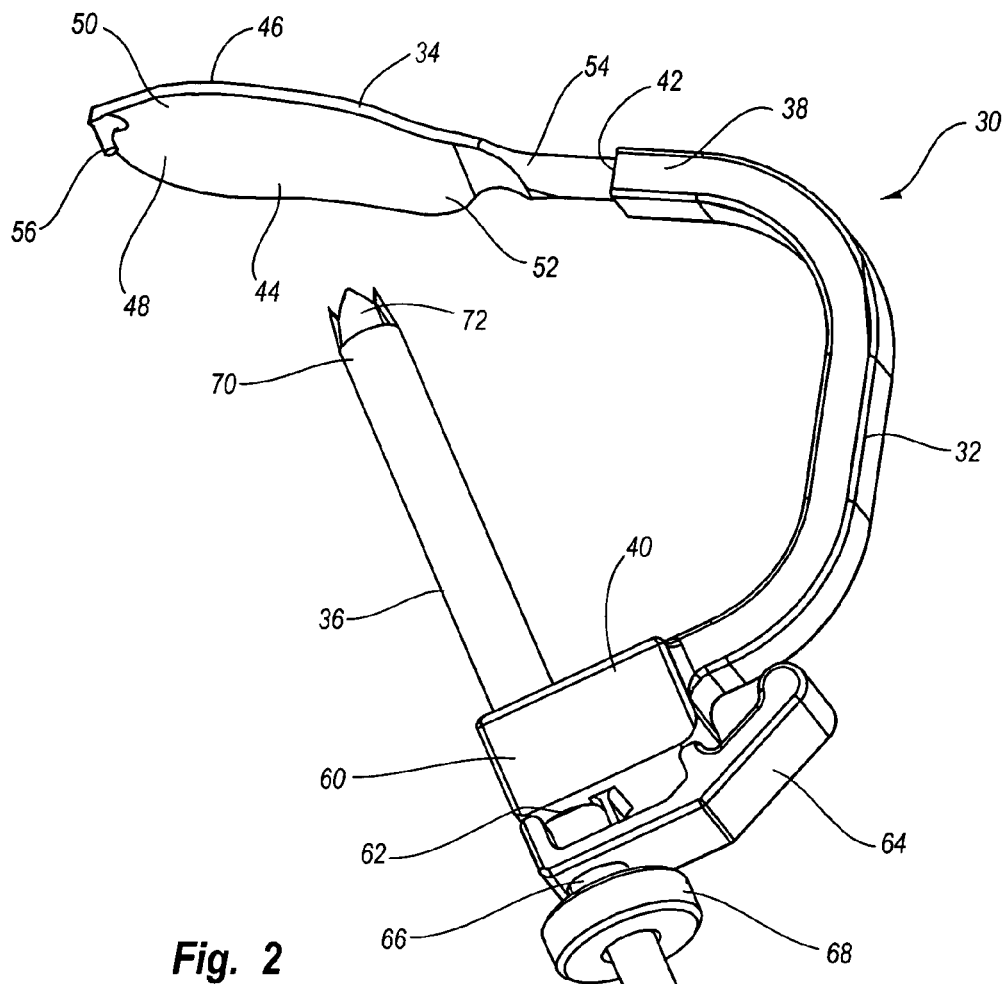
FIG. 2 is a perspective view of a guide assembly for forming a tunnel on the proximal end of the tibia shown in FIG. 1.

Depicted in FIG. 2 is one embodiment of a guide assembly 30 which is now used for forming a tunnel through a portion of tibia 12. As discussed below in greater detail, the tunnel can be used for preparing tibia 12 for a condylar implant and/or securing a condylar implant to tibia 12. In general, guide assembly 30 includes a substantially U-shaped guide brace 32 having a template 34 and a tubular guide sleeve 36 mounted on opposing ends thereof. More specifically, guide brace 32 has a first end 38 and an opposing second end 40. Recessed in first end 38 is a socket 42.

Template 34 comprises a low profile base plate 44 having a top surface 46 and an opposing bottom surface 48 which each extend between a first end 50 and an opposing second end 52. Although not required, in one embodiment bottom surface 48 has a configuration generally complementary to medial facet 24 of the superior auricular surface of tibia 12. Base plate 44 typically has a maximum thickness extending between surfaces 46 and 48 in a range between about 1 mm to about 4 mm. Projecting from second 52 of base plate 44 is a stem 54. Stem 54 is configured to be slidably received within socket 42 of guide brace 32. A catch 56 downwardly extends from bottom surface 48 of base plate 44 at first end 50. As depicted, catch 56 has the configuration of a narrow finger. In other embodiments, catch 56 can comprise an elongated ridge or other configurations.

Formed on second end 40 of guide brace 32 is an enlarged housing 60 having a passage 62 extending therethrough. A resiliently flexible clamp arm 64 is mounted to housing 60. An aperture 66 extends through clamp arm 64 in general alignment with passage 62.

Tubular guide sleeve 36 slidably extends through passage 62 and aperture 66. Guide sleeve 36 has a proximal end 68 and an opposing distal end 70. A plurality of sharpened teeth 72 are formed at distal end 70. By pressing clamp arm 64 toward housing 60, passage 62 and aperture 66 are aligned allowing guide sleeve 36 to freely slide within passage 62 and aperture 66 to a desired location. As clamp arm 64 is released, clamp arm 64 resiliently biases away from housing 60 so as to bind guide sleeve 36, thereby securing guide sleeve 36 in the desired location. In alternative embodiments, it is appreciated that clamp arm 64 can be replaced with a set screw, clamp, or a variety of other types of fasteners that can be used to selectively secure guide sleeve 36 to second end 40 of guide brace 32.

Figure 3:
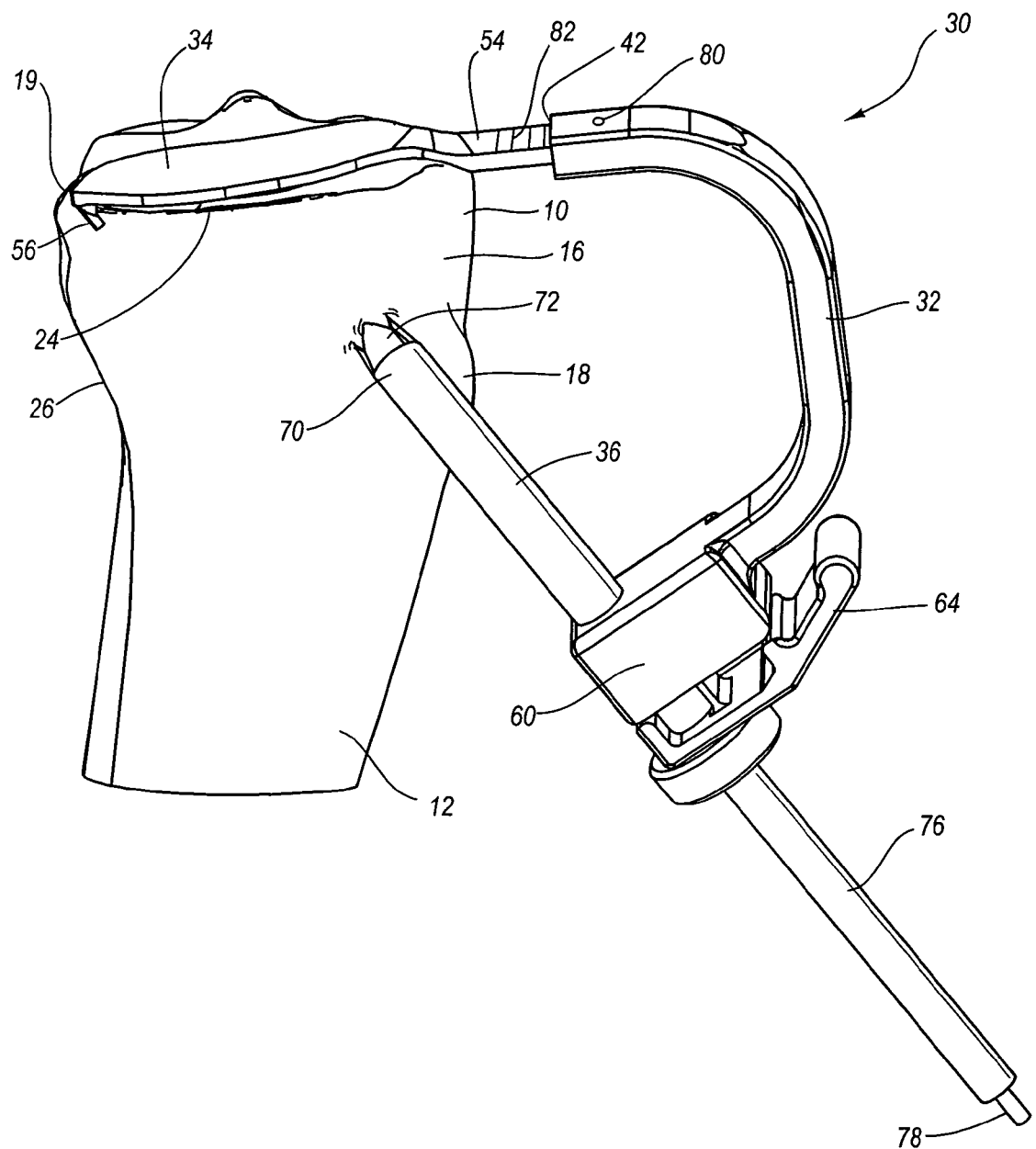
FIG. 3 is a perspective view showing the guide assembly in FIG. 2 mounted on the tibia of FIG. 1.

During use, as depicted in FIG. 3, template 34 is slid over medial facet 24 of tibia 12, i.e., the articulation surface, so that catch 56 catches on posterior side 19 of tibia 12. Catch 56 thus facilitates proper positioning of template 34 and also helps to retain template 34 on medial facet 24. It is appreciated that the size and shape of the lateral and medial facets of the superior articular surfaces of the tibia varies between different patients. As such, the present invention comprises a plurality of alternative templates 34 which are configured for placement on one of the lateral and medial facet and which each have a different configuration. As such a number of the alternative templates 34 can be initially test fitted to determine one that has a best fit for a particular patient.

Figure 2A:
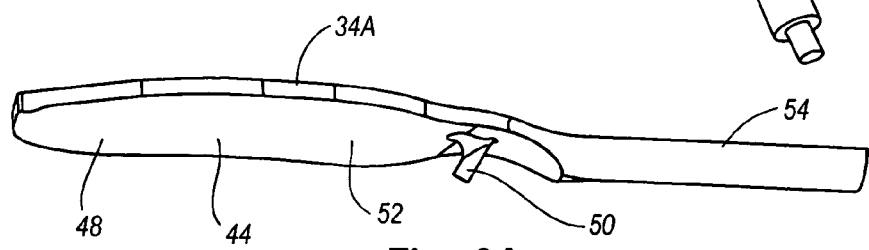
FIG. 2A is a perspective view of an alternative template used with the guide assembly shown in FIG. 2.

For example, depicted in FIG. 2A is one alternative template 34A that is smaller than template 34. Like elements between templates 34 and 34A are identified by like reference characters. In further contrast to template 34, template 34A has a catch 56A downwardly extending from second end 52 of base plate 44. Catch 56A thus biases against anterior side 18 or medial side 16 of tibia 12 to help properly position template 34A. In yet other embodiments, in contrast to positioning the projection on one of the opposing ends of base plate 44, the projection can be positioned along one of the opposing sides of base plate 44 so as to bias against lateral side 14 (when used on lateral facet 22) or bias against medial side 16 of tibia 12.

Once template 34 is selected and properly positioned on medial facet 24, tubular guide sleeve 36 is advanced within housing 60 so that teeth 72 at distal end 70 bias against medial side 16 of proximal end 10 of tibia 12. As such, tubular guide sleeve 36 biases against tibia 12 at a location spaced apart from the articulation surface of medial facet 24. Guide sleeve 36 is then secured in place by releasing clamp arm 64. By securing guide sleeve 36 against tibia 12, guide assembly 30 is clamped onto tibia 12. In one alternative embodiment, guide sleeve 36 can be biased against anterior side 18 of tibia 12.

Next, a tubular drill sleeve 76 is inserted into tubular guide sleeve 36. Positioned within drill sleeve 76 is a guide wire 78. Using drill sleeve 76 as a guide, guide wire 78 is drilled through tibia 12 until guide wire 78 reaches template 34, thereby forming a guide tunnel. In part, template 34 functions as a shield to prevent guide wire 78 and/or other drill tools from accidentally contacting and damaging the femur. In other embodiments, a hole or recess is formed on template 34. Guide wire 78 can be passed through or into the hole or recess to ensure complete formation of the tunnel on medial facet 24.

Once the guide tunnel is formed, guide wire 78 and drill sleeve 76 are removed from guide sleeve 60. A larger drill tool, not show, such as a larger guide wire, drill bit, or the like is then passed through guide sleeve 60 and drilled through tibia 12 along the guide tunnel to form a final tunnel 90 (FIG. 4) through tibia 12. It is appreciated that any number of progressively larger drill tools can be used. In alternative embodiments guide wire 78 and drill sleeve 76 can be eliminated. A single larger drill tool can then be used to form tunnel 90 in a single pass. Using a sequence of larger drill tools, however, helps ensure proper placement of tunnel 90 and facilitates forming the opening of the tunnel adjacent to template 34.

As discussed below in greater detail, the angular orientation of tunnel 90 is typically held constant and is based on the configuration of the implant. However, depending on the amount of bone needed to be resected for mounting the condylar implant, it may be necessary to shift the position of tunnel 90 posterior or anterior. Shifting the position of tunnel 90 posterior-anterior is accomplished by selectively moving stem 54 of template 34 further into or further out of socket 42 of guide brace 32. Once template 34 and guide brace 32 are positioned at their relative positions, a set screw 80 is tightened so as to secure template 34 and guide brace 32 together. Predefined markings 82 are formed on stem 54 to help define the relative positioning between template 34 and guide brace 32.

Figure 4:
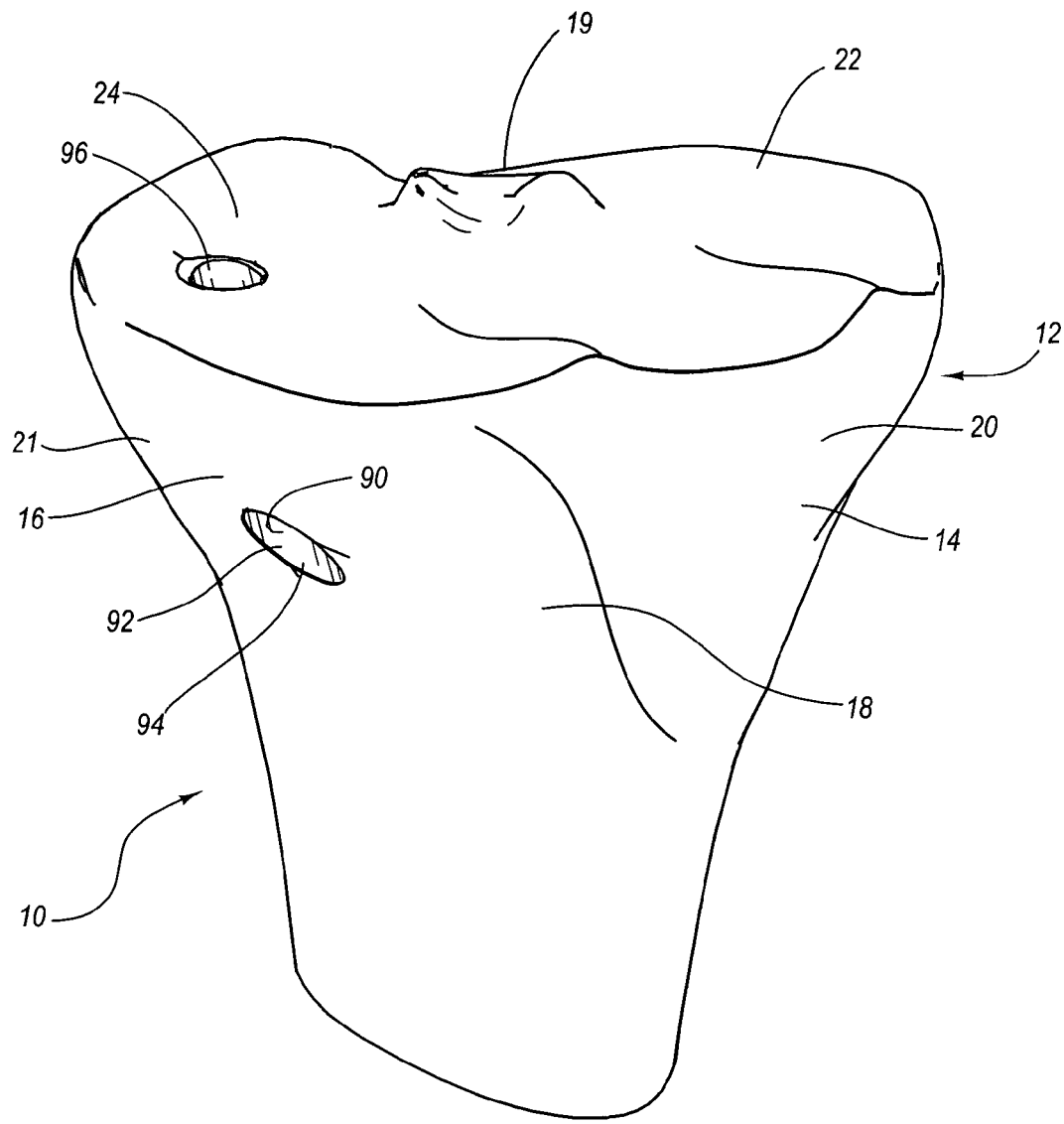
FIG. 4 is a perspective view of the tibia shown in FIG. 1 having a tunnel formed thereon.

Once tunnel 90 is formed, guide assembly 30 is removed so as to produce tibia 12 shown in FIG. 4. As depicted, tunnel 90 has an interior surface 92 that extends from a first end 94 to an opposing end second end 96. First end 94 is formed on medial side 16 of proximal end 10 of tibia 12. Second end 96 is formed on medial facet 24 of tibia 12. Expressed in other terms, second end 96 of tunnel 90 is formed on a section of an articulation surface, i.e., medial facet 24, while first end 94 is at a location on tibia 12 that is spaced apart from the articulation surface. Although tunnel 90 can be any desired size, in one embodiment tunnel 90 has a diameter in a range between about 5 mm to about 10 mm.

Using the above discussed methods and instruments, tunnel 90 is formed by procedures that are minimally invasive to the patient. As discussed below in greater detail, once tunnel 90 is formed, tunnel 90 can then be used to assist in the resection of medial fact 24 and/or the mounting of a condylar implant on the resected medial facet 24. Furthermore, by using tunnel 90 the resection of medial facet 24 and the mounting of the condylar implant can also be performed using procedures that are minimally invasive.

Figure 5:
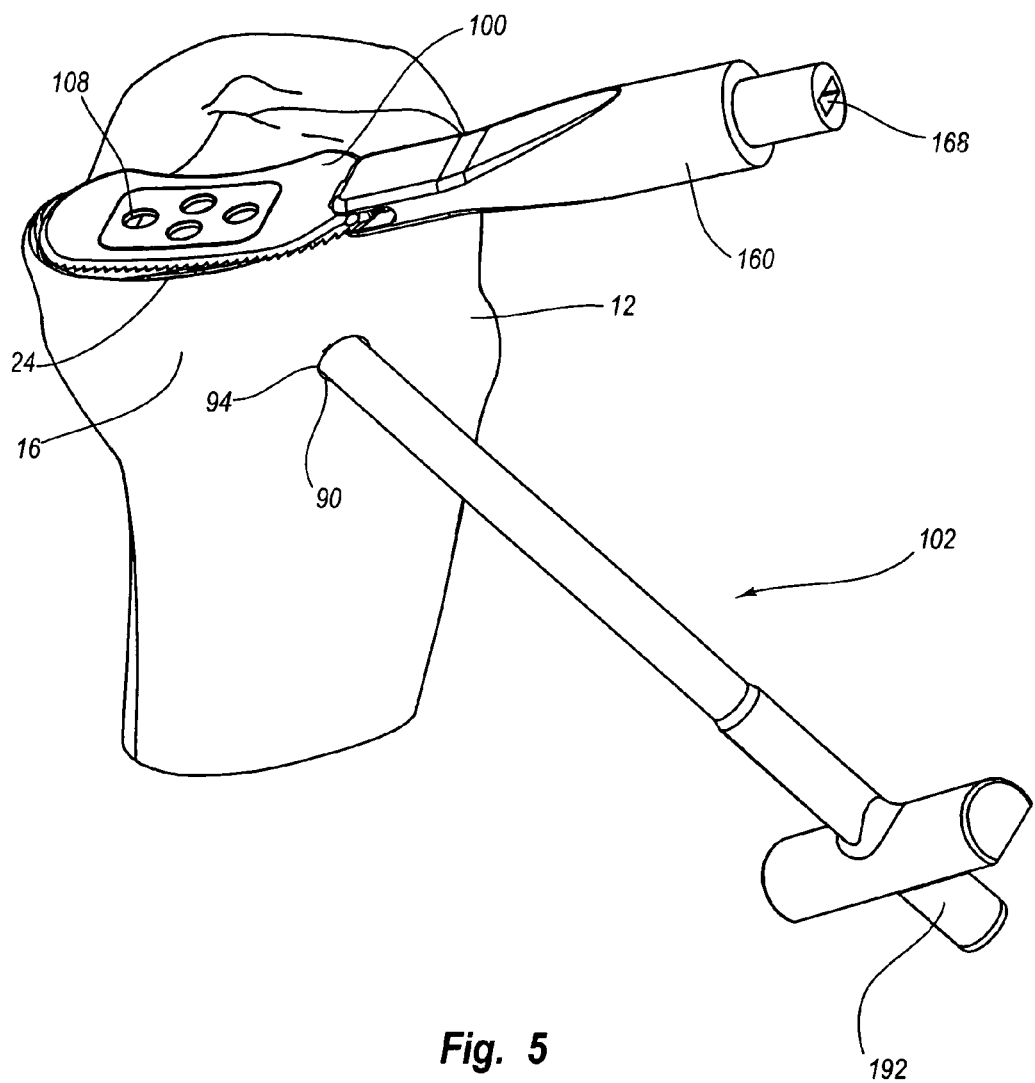
FIG. 5 is a perspective view of a rasp assembly resecting the tibia of FIG. 4.

Although not required, in one embodiment as mentioned above, tunnel 90 is used in the resection of tibia 12 for preparing tibia 12 to receive a condylar implant. The resection of tibia 12 can be accomplished using a number of different procedures. For example, as depicted in FIG. 5, is one embodiment a rasp assembly 100 is used in association with a retention rod 102 to facilitate resection of tibia 12.

Figure 6:
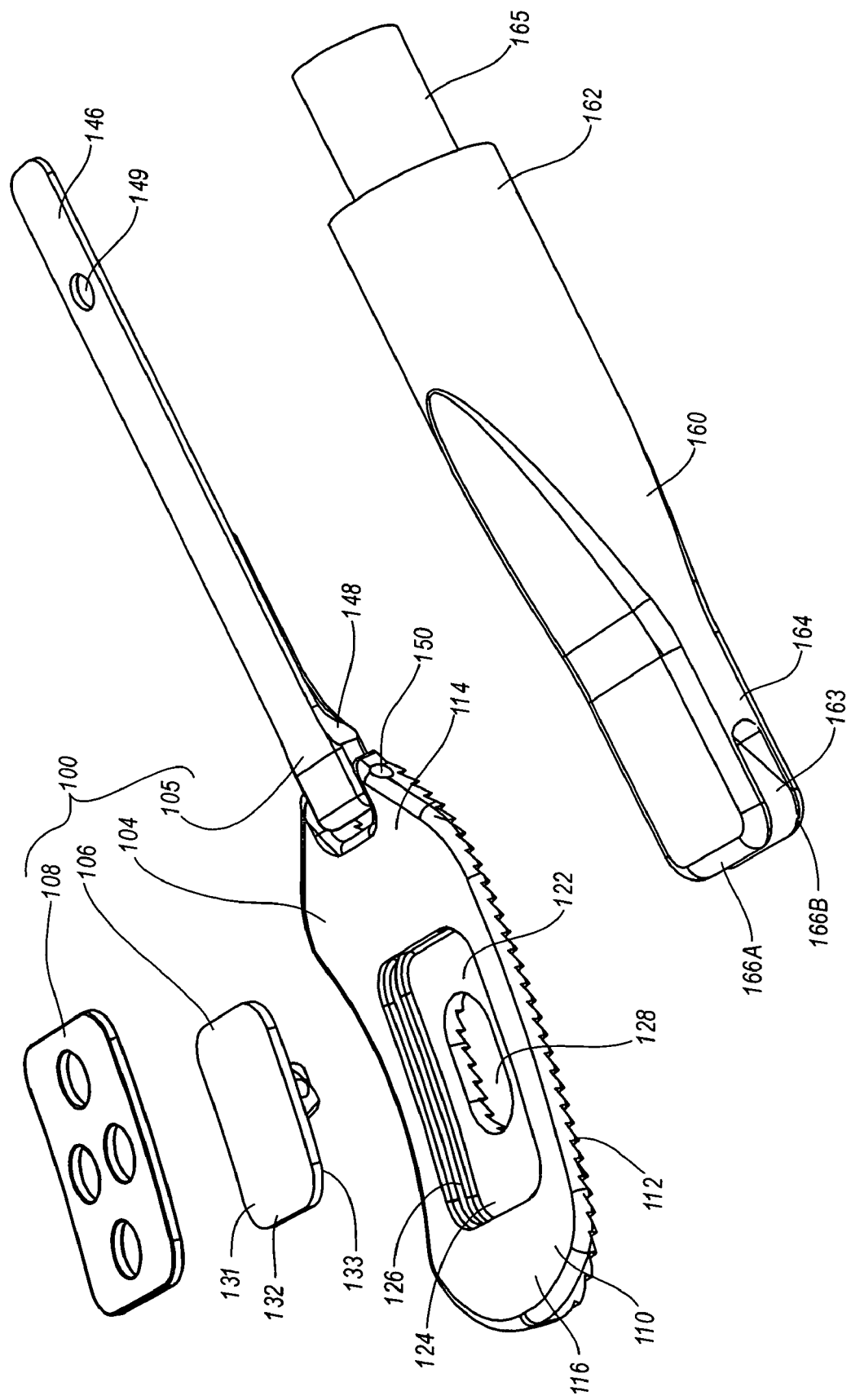
FIG. 6 is a top perspective view of the raps assembly shown in FIG. 5.
Figure 7:
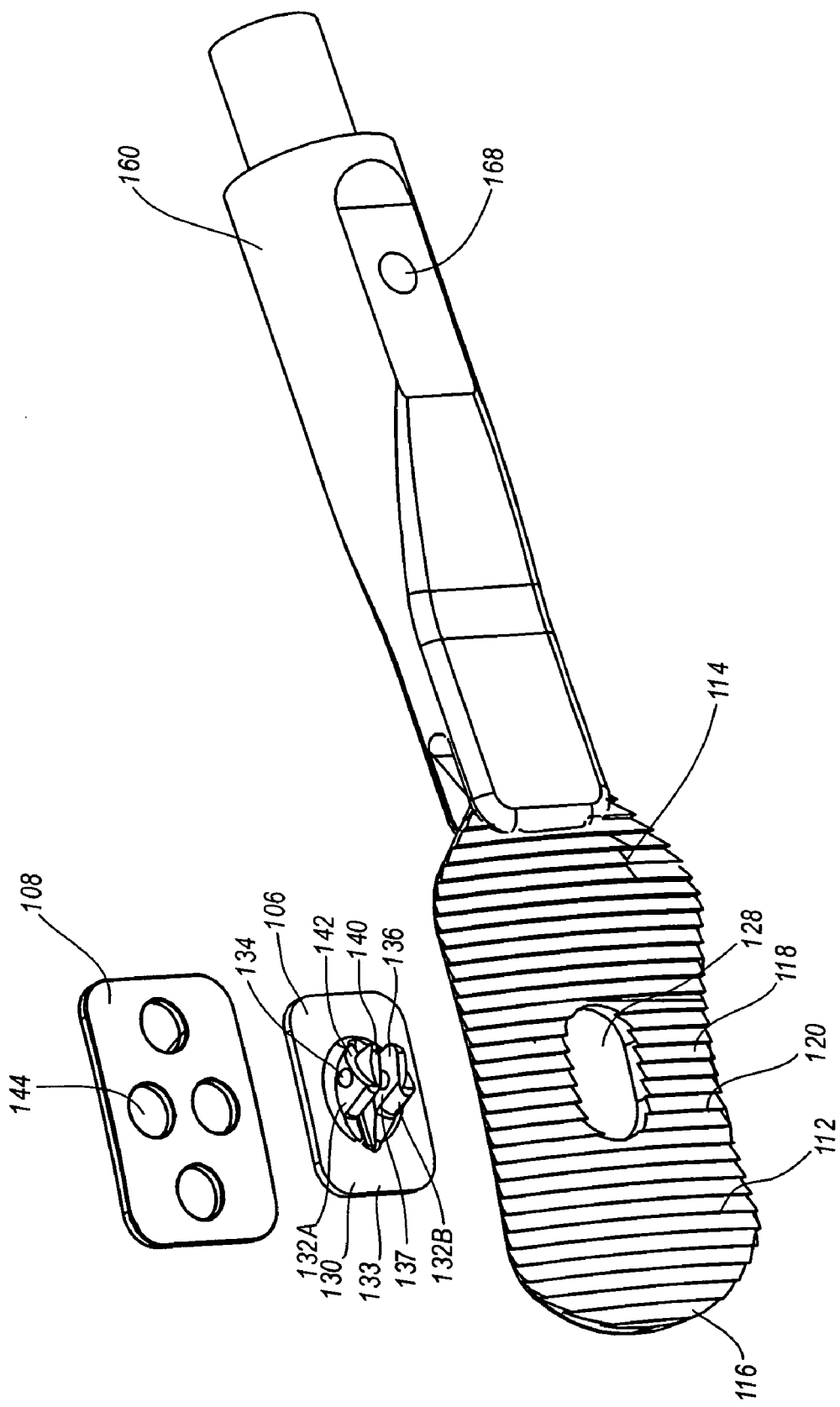
FIG. 7 is a bottom perspective view of the rasp assembly shown in FIG. 6.

As depicted in FIG. 6, rasp assembly 100 comprises a rasp body 104 having a pivot arm 105 mounted thereon, a rasp guide 106, and a cover plate 108. More specifically, as depicted in FIGS. 6 and 7, rasp body 104 has a top surface 110 and an opposing bottom surface 112 that each extend between a proximal end 114 and an opposing distal end 116. Transversely extending across bottom surface 112 are a plurality of ridges 118 that each terminate at a sharpened cutting edge 120. It is appreciated that ridges 118 and cutting edges 120 can be at any desired orientation or combination of different orientation that facilitate cutting. Bottom surface 112 is configured such that reciprocating movement of bottom surface 112 on tibia 12 produces a recess on tibia 12 that can receive a desired implant. Recessed on top surface 110 of rasp body 104 is a guide slot 122. Guide slot 122 is bounded by a floor 124 and a sidewall 126 upstanding from floor 124. Extending through floor 124 to bottom surface 112 is an opening 128.

Rasp guide 106 comprises a slide plate 130 having a top surface 131 and an opposing bottom surface 133. Downwardly projecting from bottom surface 133 are a pair of spaced apart forks 132A and 132B with a pin 134 extending therebetween. Forks 132A and B have facing interior surfaces 136 which bound a gap 137 and have opposing exterior surfaces 138. Forks 132A and B terminate at a free terminus 140. Exterior surface 138 of each fork 132A and B is recessed at terminus 140 such that a sloping shoulder 142 is formed on each fork 132A and B.

Rasp guide 106 is received within guide slot 122 so that forks 132A and B project through opening 128. Rasp guide 106 is slightly smaller than guide slot 122 such that forks 132A and B are free to reciprocate within opening 128 as slide plate 130 reciprocates within guide slot 122. As shown in FIG. 5, cover plate 108 is secured within guide slot 122 so as to retain rasp guide 106 within guide slot 122. Cover plate 108 can be mounted using conventional techniques such as welding, press fit, and the like. Holes 144 are formed through cover plate 108 to prevent unwanted build-up of resected bone particles within guide slot 122.

As depicted in FIG. 6, pivot arm 105 has a proximal end 146 and an opposing distal end 148. A set hole 149 extends through pivot arm 105 toward proximal end 146. Distal end 148 of arm 105 is hingedly mounted to proximal end 114 of rasp body 104 by a pin 150.

In one embodiment, an insertion handle 160 is used to place rasp body 104 over medial facet 24 of tibia 12. Insertion handle 160 has a proximal end 162 and an opposing distal end 164. A post 165 is formed a proximal end 162. Post 165 is adapted to receive an extension handle if desired. A pair of spaced apart lips 166A and B project from distal end 164 and bound a slot 163. A channel 168 (FIG. 5) longitudinally extends through insertion handle 160 so as to communicate with slot 163. Channel 168 is configured to receive pivot arm 105 when rasp body 104 is received within slot 163.

During use, pivot arm 105 is slid into channel 165 from between lips 166A and B. Lips 166A and B are then advanced to extend above and below proximal end 114 of rasp body 104. A set screw 168 (FIG. 7) is then advanced into insertion handle 160 so as to extend through set hole 149 on pivot arm 105. In this configuration insertion handle 160 rigidly supports rasp body 104 so as to prevent hinged movement of rasp body 104 during insertion.

Figure 8:
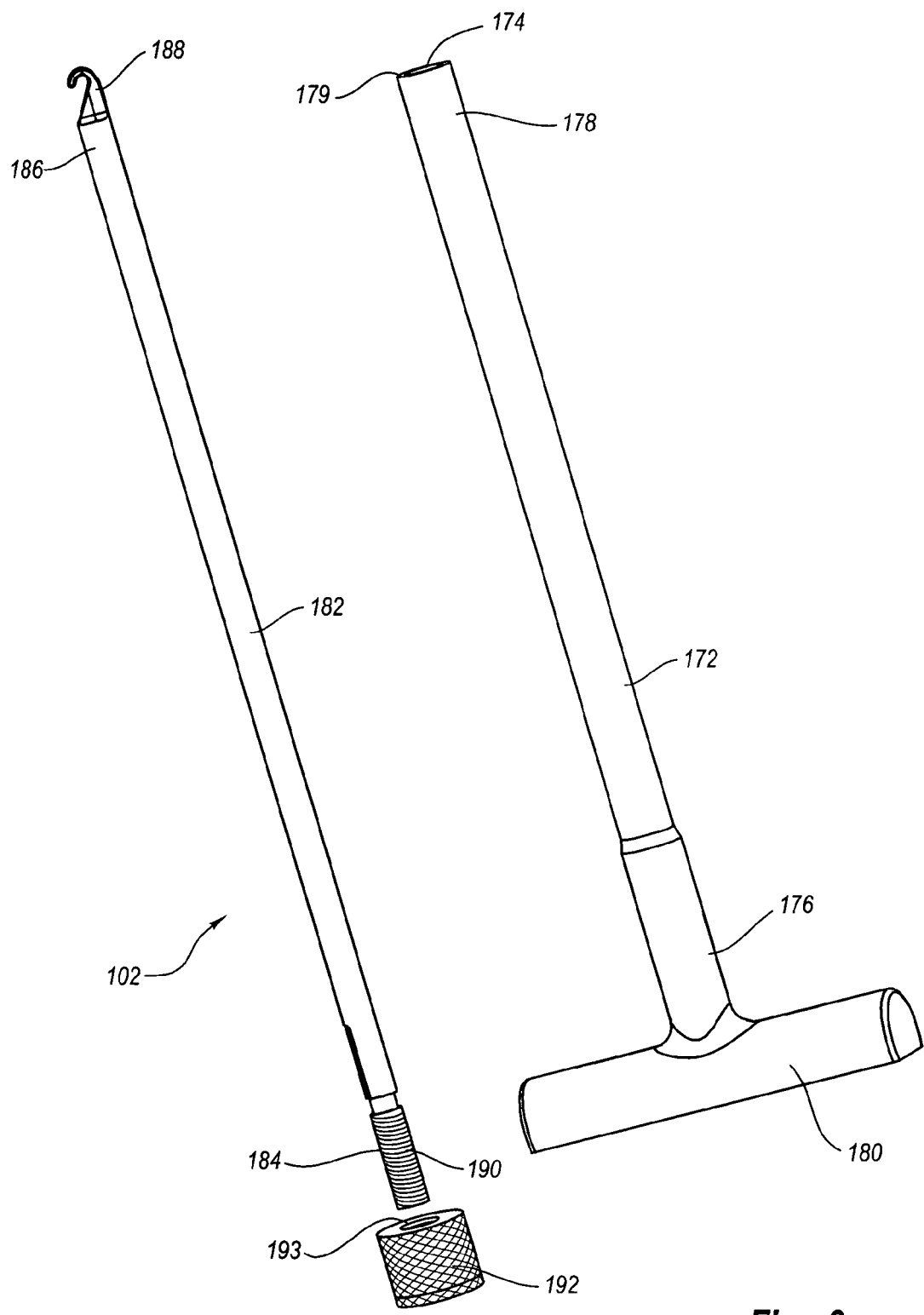
FIG. 8 is an exploded perspective view of the retention rod shown in FIG. 5.

Turning to FIG. 8, retention rod 102 comprises a tubular set rod 172 bounding a channel 174 extending from a proximal end 176 to an opposing distal end 178. Distal end 178 terminates at a distal end face 179. A handle 180 outwardly projects from proximal end 176 to facilitating grasping retention rod 102.

Retention rod 102 further comprises a hook rod 182. Hook rod 182 has a proximal end 184 and an opposing distal end 186. Projecting from distal end 186 is a hook 188. Threads 190 are formed on proximal end 184. A knob 192 is also provided having a threaded port 193. Threads 190 on hook rod 182 are configured to mate with threaded port 193 of knob 192. Hook rod 182 is received within channel 174 of set rod 172 such that knob 192 biases against handle 180 and hook 188 extends beyond distal end face 179. In this configuration, rotation of knob 192 relative to hook rod 182 causes hook 188 to extend or retract relative to set rod 172.

Figure 9A:
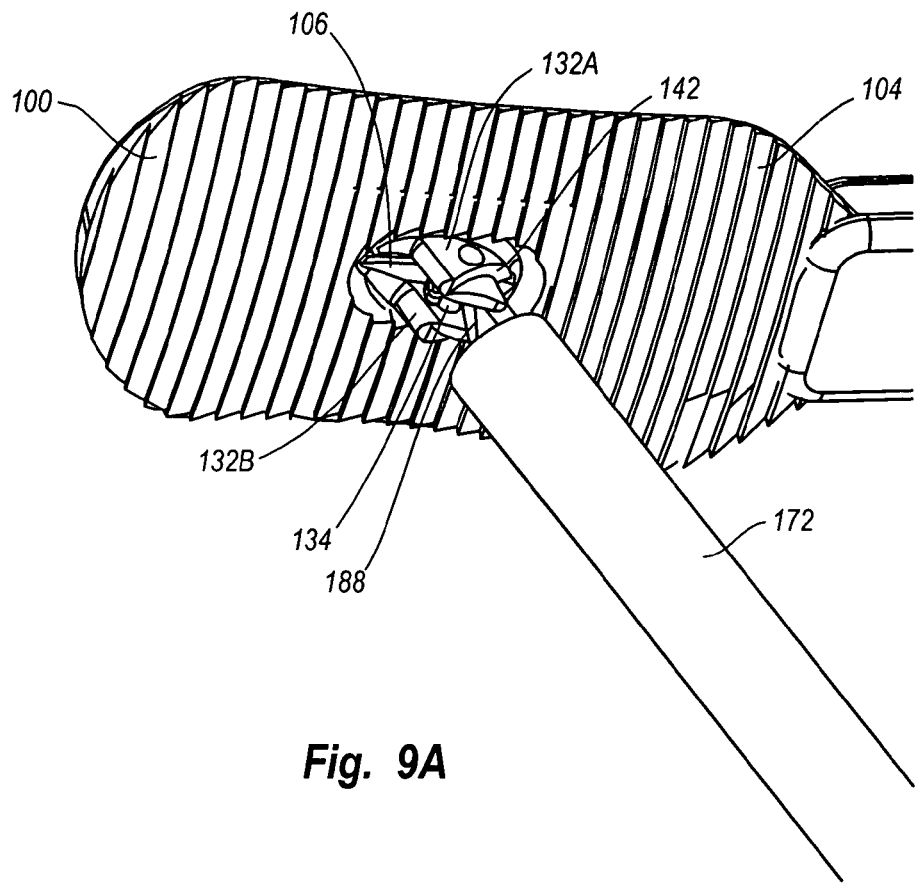
FIGS. 9A and 9B are perspective views of the retention rod shown in FIG. 8 being mounted to the rasp assembly shown in FIG. 5.

During operation, as depicted in FIG. 5, rasp assembly 100 is mounted on medial facet 24 of tibia 12. Rasp assembly 100 is positioned using the rigidly mounted insertion handle 160, as discussed above, such that forks 132A and B (FIG. 7) are aligned with the second end 96 of tunnel 90. Once rasp assembly 100 is positioned, retention rod 102 is advance within tunnel 90 from first end 94. As depicted in FIG. 9A, knob 192 is rotated so that hook 188 extends beyond set rod 172. With hook 188 freely exposed, hook 188 is hooked over pin 134 extending between forks 132A and B.

Figure 9B:
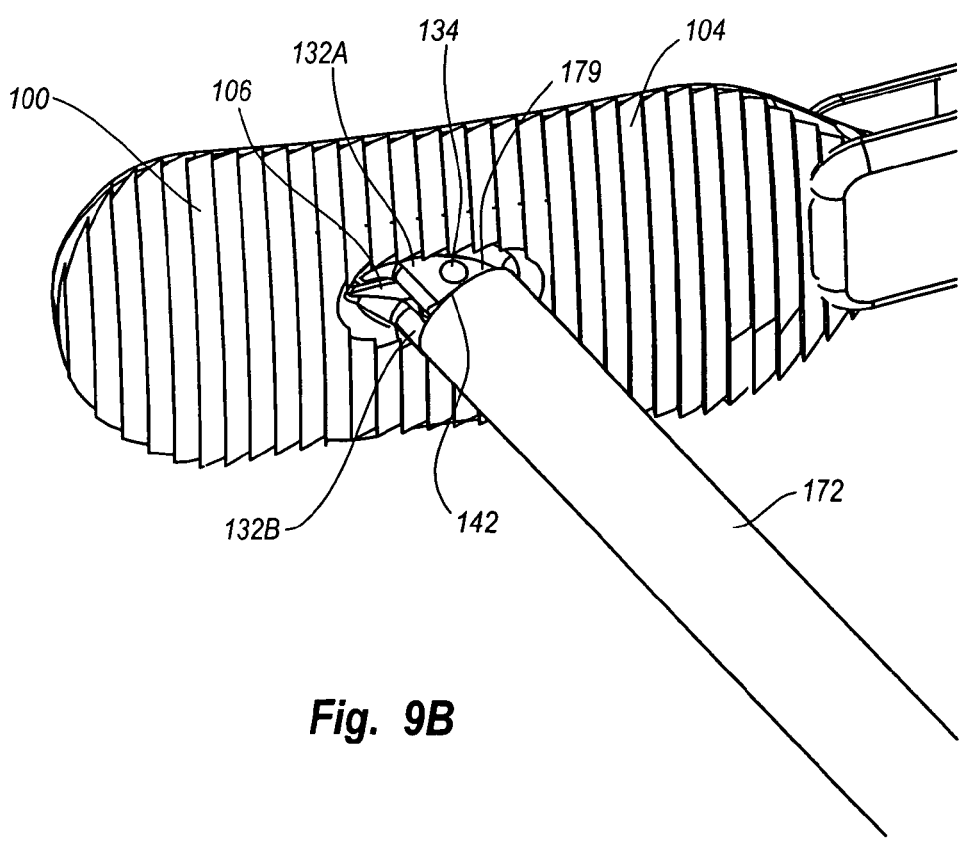

As depicted in FIG. 9B, once hook 188 has captured pin 134, knob 192 is rotated so as to advance set rod 172 toward hook 188. Set rod 172 is advanced until distal end face 179 of set rod 172 biases against shoulders 142 of forks 132A and B. Shoulders 142 are sloped such that end face 179 can sit flush against shoulder 142 while set rod 172 retains its orientation within tunnel 90. In this configuration, retention rod 102 is securely fixed to rasp guide 106.

Once retention rod 102 is secured to rasp assembly 100, insertion handle 160 is removed from pivot arm 105. A reciprocal driver, such as a reciprocal saw, not shown, is then connected pivot arm 105. While holding rasp guide 106 substantially stationary by holding onto retention rod 102, the reciprocal driver rapidly reciprocates rasp body 104 so that cutting edges 120 resect medial facet 24 of tibia 12. In one embodiment, rasp body 104 reciprocates along a length in a range between about 1 mm to about 4 mm. Other dimensions can also be used.

In one embodiment bottom surface 112 of rasp body 104 slightly arched so as to be convex. By having pivot arm 105 hingedly attached to rasp body 104, rasp body 104 is free to reciprocate along the arched path. The hinged attachment also helps to minimize binding of rasp body 104. In alternative embodiments, arm 105 can be rigidly attached to rasp body 104.

In one embodiment of the present invention means are provided for removably engaging retention rod 102 with rasp body 104 such that rasp body 104 can be selectively reciprocated without substantial movement of retention rod 102. By way of example and not by limitation, one embodiment of the means comprises rasp guide 106 slidably mounted on rasp body 104 and hook 188 mounted on retention rod 102. In alternative embodiments it is appreciated that a variety of different structures can accomplish the same function. For example, pin 134 and hook 188 can be replaced with a threaded connection, bayonet connection, or any number of other conventional connections which allows retention rod 102 to engage with rasp guide 106.

It is also appreciated that rasp guide 106 can be mounted on rasp body 104 in a variety of different ways. For example, opening 128 can extend through rasp body 104 without the formation of guide slot 122. In this embodiment slide plate 130 can be positioned directly on top surface 110 of rasp body 104 while forks 132A and B extend through opening 128. In yet another alternative, guide slot 122 can be formed on bottom surface 112 of rasp body 104. Cover plate 108 can be formed having opening 128 extending therethrough and cutting edges 120 formed on a bottom surface thereof. Slide plate 130 can be positioned within the guide slot 122 so that when cover plate 108 is secured over guide slot 122, forks 132A and B extend through opening 128 formed on cover plate 108.

It is also appreciated that retention rod 102 can have a variety of different configurations. For example, in alternative embodiments set rod 172 can be eliminated. As such, retention rod 102 can simply comprise hook rod 182. Furthermore, as discussed above, hook 188 can be replaced with a variety of different types of connectors.

Figure 10:
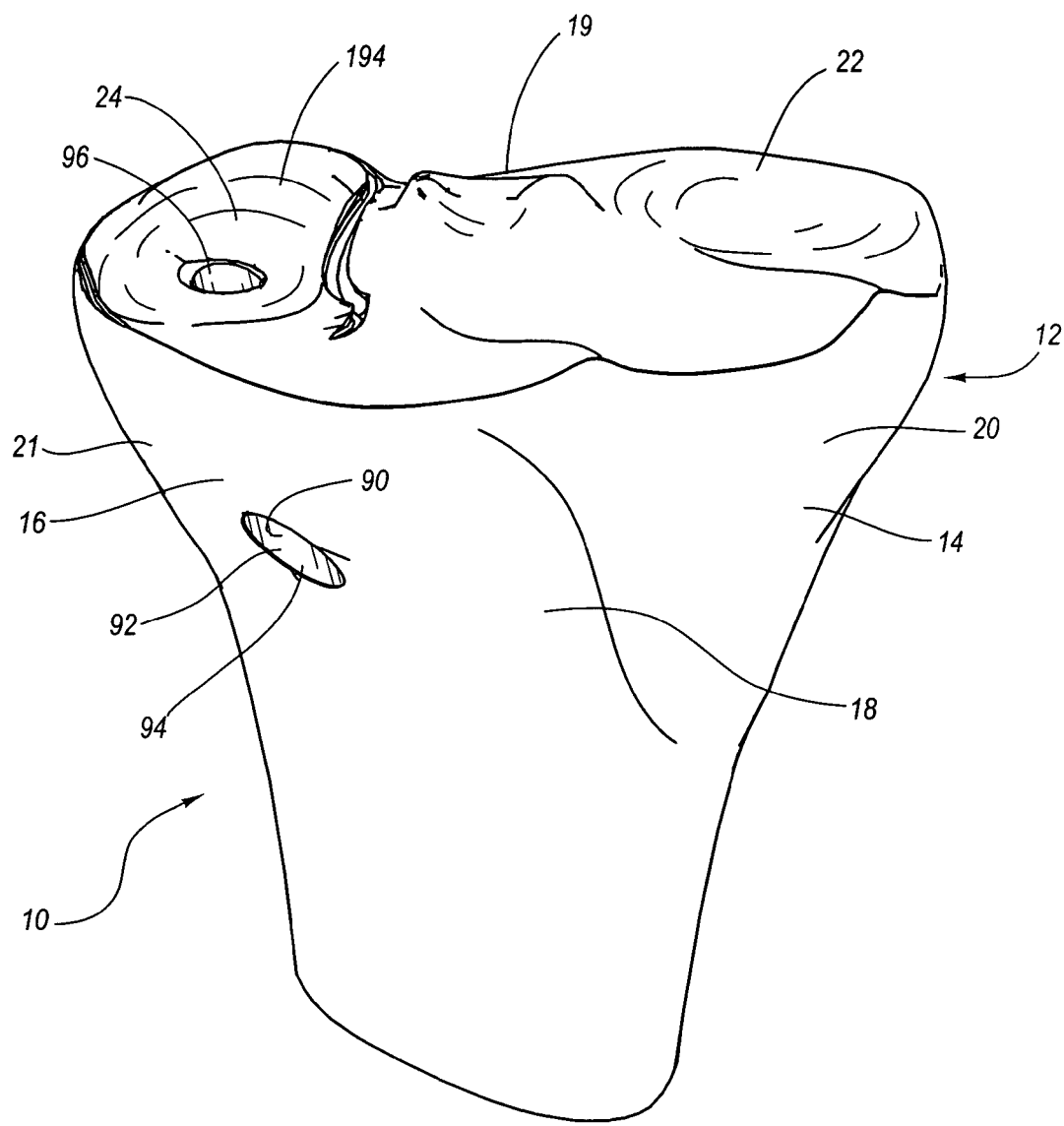
FIG. 10 is a perspective view of the tibia shown in FIG. 4 having a recess formed thereon.

Once medial facet 24 has been sufficiently resected by rasp body 104, rasp assembly 100 and retention rod 102 are removed. The resected bone particles are removed by conventional flushing and suction. As depicted in FIG. 10, tibia 12 now has a resected recess 194 formed on medial facet 24.

Figure 11:
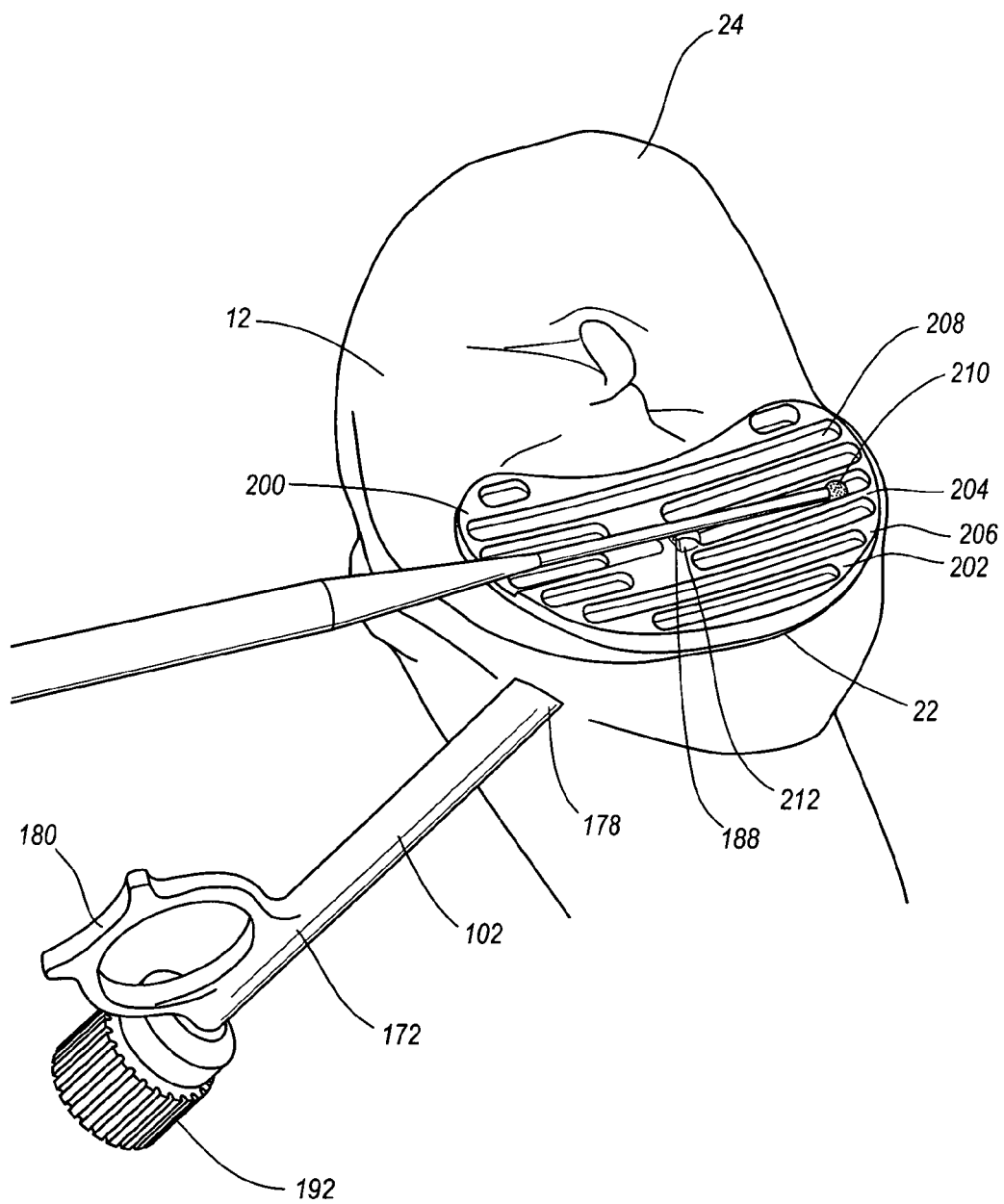
FIG. 11 is a perspective view of a cutting template being mounted on the tibia shown in FIG. 4.

It is appreciated that the resection of tibia 12 can be accomplished using a variety of different techniques. For example, in one alternative depicted in FIG. 11, the resection of tibia 12 is accomplished by cutting through an area bounded by a cutting template 200. Cutting template 200 comprises a plate 202 having a top surface 204 and an opposing bottom surface 206. In the embodiment depicted cutting template 200 is configured to rest on lateral facet 22 of tibia 12. Of course, cutting template 200 can also be designed for resting on medial facet 24.

Extending between opposing surfaces 204 and 206 are a plurality of guide spaces 208. Guide spaces 208 are formed so that when cutting template 200 is positioned, guide spaces 208 are positioned over at least a portion of the facet to be resected. In the embodiment depicted, guide spaces 208 have the configuration of an elongated channel. As will be discussed below in greater detail, the channels facilitate guided receipt of a cutting burr 210 which is used to selectively remove the unwanted bone. In alternative embodiments, depending on the type and size of tool used to remove the bone, guide spaces 208 can come in a variety of different sizes, shapes, and orientations.

In one embodiment, although not required or shown, a second cutting template is provided having guide spaces extending therethrough. In the second cutting template, the guide spaces are aligned so as to bound the area of the facet to be resected which was blocked by plate 202 of cutting template 200. As a result, by sequentially using both cutting templates, all or at least a greater proportion of the bone can be removed by cutting burr 210. Additional cutting templates can also be used.

Cutting template 200 is used in association with retention rod 102 as previously discussed. In the embodiment depicted, handle 180 has a different configuration. During use, cutting template 200 is position over lateral facet 22. Distal end 178 of set rod 172 is advanced through tunnel 90 so that hook 188 of hook rod 182 projects out of set rod 172. Hook 188 is passed though a guide space 208 and then pulled back onto top surface 204 of plate 202. A rib 212 upwardly projects from plate 202 adjacent to guide space 208. Hook 188 is hooked over rib 212 so as to improve the engagement between hook 188 and cutting template 200.

Once hook 188 is engaged to cutting template 200, knob 192 is rotated so as to bias set rod 172 against bottom surface 206 of template 200. As a result, retention rod 102 is securely clamped to cutting template 200. Accordingly, by pulling retention rod 102, cutting template 200 is securely held in place on lateral facet 22. Cutting burr 210 or some other form of drill bit is then advanced into and along each of guide spaces 208 so as to resect the portion of the bone directly below guide space 208. As previously discussed, in one embodiment cutting template 200 can be removed and replaced with a second template. Burr 100 can then be passed through guide spaces of the second template to remove further bone that was covered by cutting template 200.

In other alternatives, it is appreciated that once cutting template 200 is removed, the remaining bone portion can be removed by sight and feel without the use of a template. In yet other embodiments, depending on the type and amount of bone needed to be resected, a single template can be rotated or shifted on lateral facet 22 so that the single template is used to remove the desired bone.

In one embodiment of the present invention, means are provided for removably engaging retention rod 102 to cutting template 200 so that retention rod 102 secures cutting template 200 to the lateral or medial facet of tibia 12 when retention rod 102 is received within tunnel 90 of tibia 12. By way of example and not by limitation, one embodiment of such means comprises hook 188 and guide space 208 which enables hook 188 to engage with cutting template 200.

The present invention also envisions that there are a variety of other structures that can accomplish the same function. For example, the same structures and techniques as discussed above for securing retention rod 102 to rasp assembly 100 can also be used with cutting template 200. That is, in one alternative forks 132A and B with pin 134 can be mounted on bottom surface 206 of plate 202. Other connections such as threaded connection, bayonet connections, and the like can also be used.

Figure 12:
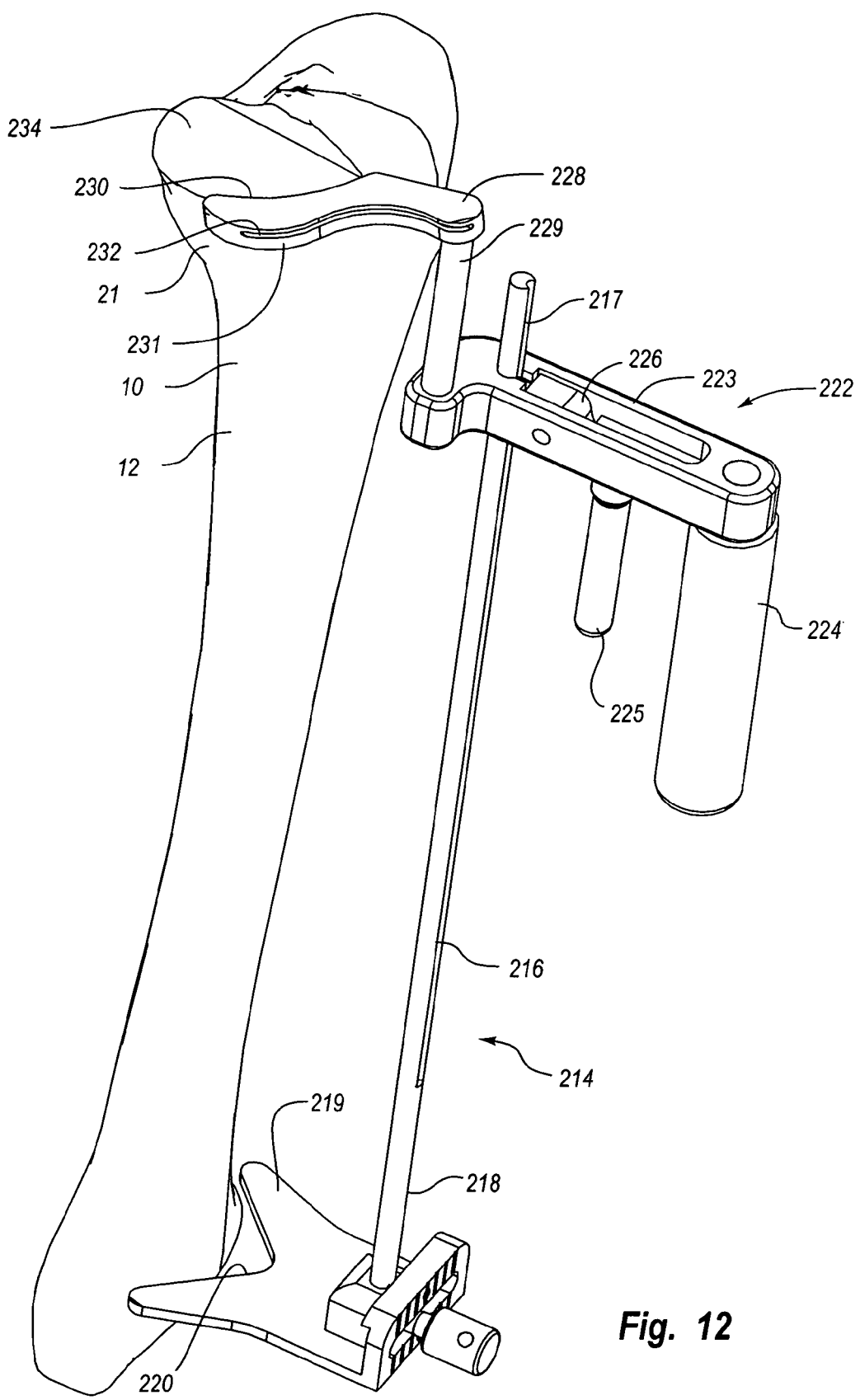
FIG. 12 is a perspective view of a tibial cutting guide positioned against a tibia.

The present invention envisions still other instruments and methods that can be used to resect medial condyle 21. For example, depicted in FIG. 12 is a guide 214. Guide 214 comprises rod 216 having an upper end 217 and an opposing lower end 218. Adjustably mounted on lower end 218 of rod 216 is a brace 219 having a v-shaped notch 220. Notch 220 is configured so that brace 219 can be securely held against the distal end of tibia 12. Adjustably mounted at the upper end of rod 216 is an adjustment mechanism 222. Adjustment mechanism 222 comprises an elongated body 223 having rod 216 slidably extending therethrough. A handle 224 and an adjacent trigger 225 are each connected to body 223. Trigger 225 is connected to a cam 226 which is spring biased against rod 216. As such, by retracting trigger 225, cam 226 is pulled back and adjustment mechanism 222 can freely slide along rod 216. Once trigger 225 is released, cam 226 is spring biased against rod 216, thereby securing adjustment mechanism 222 in place.

A cutting guide 228 is connected to body 223 by a post 229. Alternatively, cutting guide 228 can be directly connected to body 223. Cutting guide 228 has an inside face 230 and an opposing outside face 231. An elongated slot 232 extends between faces 230 and 231. Inside face 230 is contoured so as to closely fit against the anterior side of medial condyle 21.

During use, guide 214 is positioned against tibia 12 as shown in FIG. 12. An operator uses handle 224 to biases guide 214 against tibia 12 so that guide 214 is securely held in position. Once positioned, a blade on an oscillating saw (not shown) is advanced through slot 232 in cutting guide 228. Using slot 232 as a guide, the blade on the oscillating saw is advanced anterior to posterior through the medial condyle 21 so as to form resected surface 234. The saw blade also cuts through the medial side of medial condyle 21. Cutting guide 228 is positioned so that the saw blade removes the articular cartilage of medial condyle 21. Thus, in one embodiment cutting guide 228 is positioned so that slot 232 is positioned at a distance typically in a range between 1 mm to about 4 mm below medial facet 24. Other dimensions can also be used.

Once the blade from the oscillating saw is removed, guide 214 is also removed. A reciprocating sagittal saw is then used to cut from the top surface of medial facet 24 down to resected surface 234 along the lateral edge of resected surface 234. The fully separated cut bone piece can then be removed from tibia 12 as shown in FIG. 12. It is appreciated that the medial meniscus can be removed prior to resection of medial condyle 21, as previously discussed, or can simply be removed concurrently with the above discussed resection of medial condyle. In yet other embodiments, it is appreciated that resected surface 234 can be formed through the use of an electric burr, mill, bone chisel, bone chipper or the like. The above resection process can be used in combination with the rasping process previously discussed. That is, either before or after forming tunnel 90, the oscillating saw or other tool can initially be used to remove the articular cartilage before rasping. The option has the benefit of easy removal of the articular cartilage which can be difficult to remove by rasping. Furthermore, the total amount of material to be removed by rasping is reduced. In addition, the above resection process provides a planar surface on the tibia which is more convenient to work with when forming a pocket for the implant.

Figure 13:
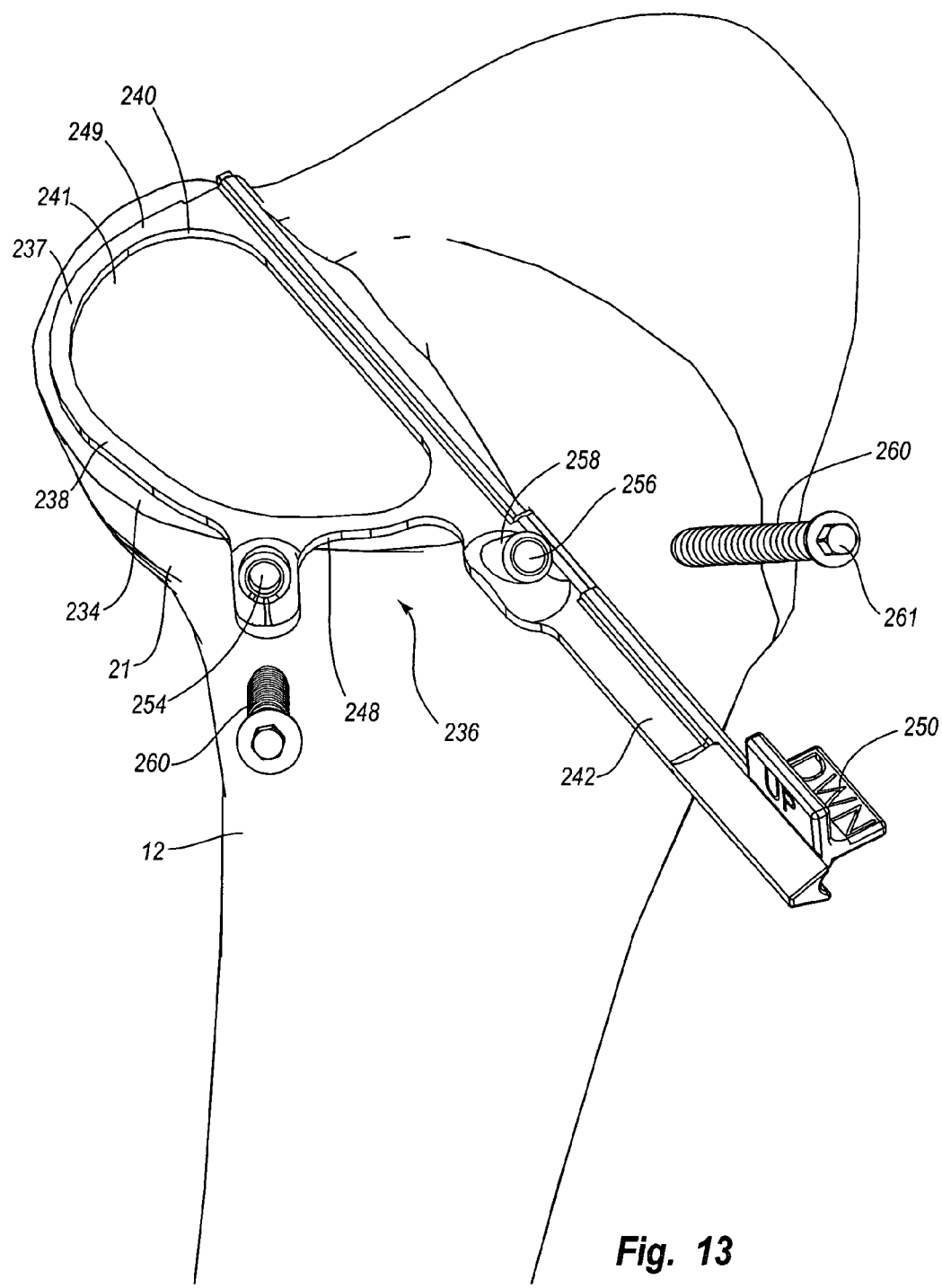
FIG. 13 is a perspective view of a guide template mounted on a resected surface of the tibia shown in FIG. 12.
Figure 14:
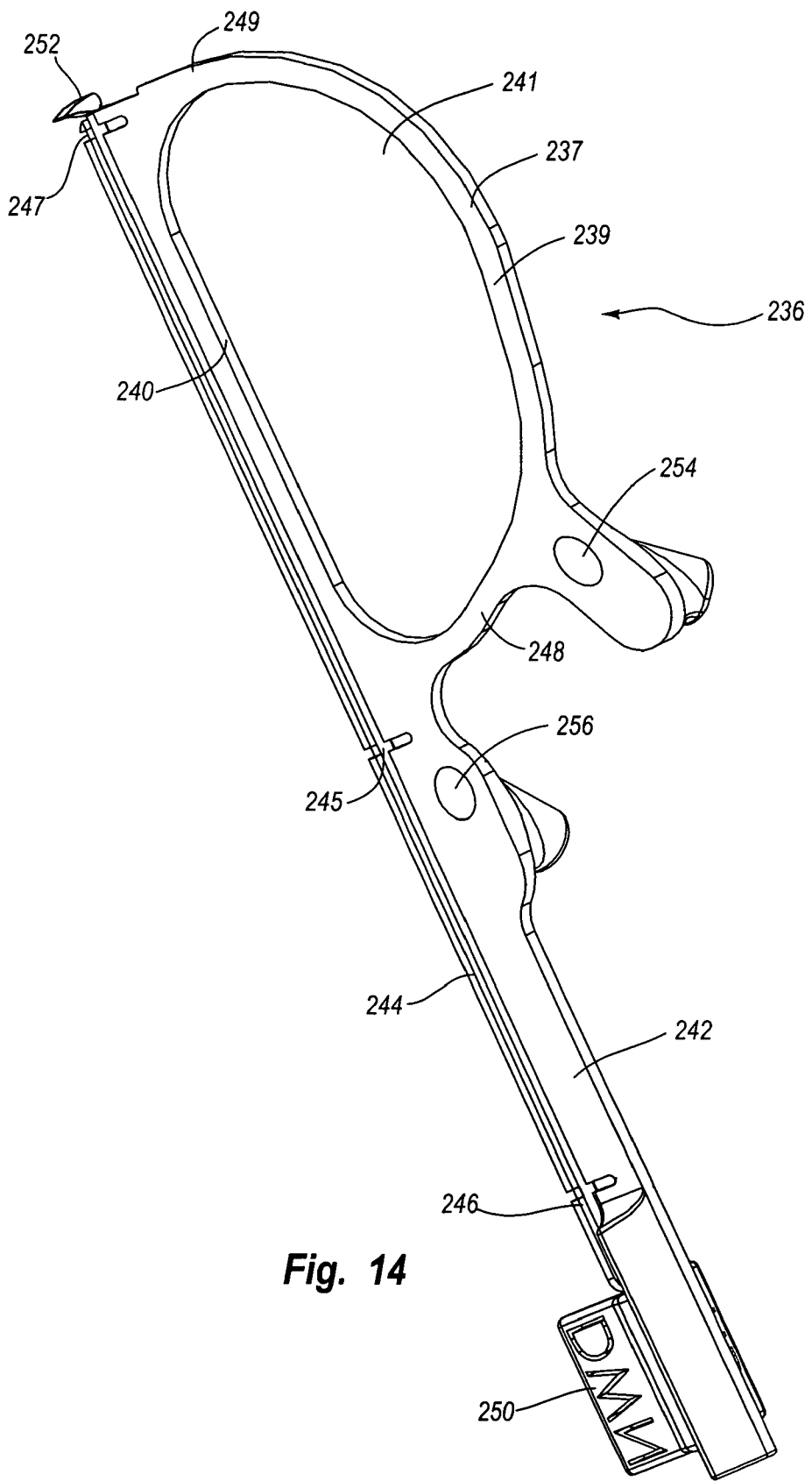
FIG. 14 is a bottom perspective view of the guide template shown in FIG. 13.

As mentioned above, in one embodiment resected surface 234 is a further resected to form a contoured pocket in which the implant can be mounted. By way of example, depicted in FIGS. 13 and 14 is a guide template 236. Guide template 236 comprises a body 237 having a top surface 238 and an opposing bottom surface 239. Although not required, in the embodiment depicted, surfaces 238 and 239 are each substantially flat and form a thickness extending therebetween which is typically in a range between about 0.5 mm to about 4 mm. Body 237 has an interior surface 240 which encircles an opening 241 extending between surfaces 238 and 239.

Opening 241 has an area that corresponds to the size of the implant. Thus, opening 241 can be any size or shape depending on the size and shape of implant to be used. In the embodiment depicted, opening 241 has an elongated configuration and typically has an area greater than about 2 cm$^2$ and more commonly greater than 3 cm$^2$. Again, other sizes and shapes can be used. Furthermore, in alternative embodiments, body 237 need not completely encircle opening 241. For example, a section of body 237 bounding opening 241 can be eliminated.

Body 237 has an anterior side 248 and an opposing posterior side 249. Projecting from anterior side 248 is an elongated handle 242. Extending along bottom a surface 239 of body 237 and handle 242 is a recessed channel 244. Rotatably disposed within channel 244 is a shaft 245. Shaft 245 has a first end 246 disposed at the free end of handle 244 and an opposing second end 247 disposed at posterior side 249 of body 237. A handle 250 is connected to first end 247 of shaft 245. Handle 250 enables the user to easily rotate shaft 245 by selective movement of handle 250. Outwardly projecting from second send 247 of shaft 245 is a catch 252. By selective rotation of shaft 245, catch 252 can be selective moved between a first position wherein catch 252 is disposed in the same plane as body 237 and a second position, as shown in FIG. 14, wherein catch 252 orthogonally projects below bottom surface 239 of body 237.

During use, catch 252 is initially oriented in the first position. Body 237 can then be easily slid anterior to posterior along resected surface 234. Catch 252 can then be rotated to the second position such that catch 252 catches on the posterior side of tibia 12. Catch 252 can thus be used to facilitate proper placement and stabilization of guide template 236 on resected surface 234. Once guide template 236 is positioned, it is checked for proper fit. That is, body 237 should extend complimentarily around the perimeter edge of resected surface 234. If not, guide template 236 is replaced with a guide template of different size and/or shape. In this regard, a plurality of guide templates 236 are provided having different sizes to fit patients of different size. It is also appreciated that guide template 236 can be configured to be adjustable in size and/or shape.

Although not required, in one embodiment means are provided for securing body 237 to tibia 12. By way of example and not by limitation, a first hole 254 and a second hole 256 are formed at two-spaced apart locations along or adjacent to anterior side 248 of body 237. The holes can also be formed on handle 242. A tubular sleeve 258 encircles and upwardly projects at an angle from each of holes 254 and 256. In part, sleeves 258 function as a guide but are not required. A pair of screws 260 are provided each having an enlarged head 261.

Once guide template 236 is appropriately positioned, screws 260 are advanced through corresponding holes 254 and 256 so as to screw into the anterior side of tibia 12. As a result of using two-spaced apart screws 260, guide template 236 is secured in place so as to prevent unwanted sliding or rotation. In alternatives embodiments, a single hole and screw can be used or three or more holes and corresponding screws can be used. Furthermore, in contrast to using screws, other types of fasteners such as barbs, spikes, expansion bolts, staples, clamps, or the like can be used to secure body 237 to tibia 12.

Figure 15:
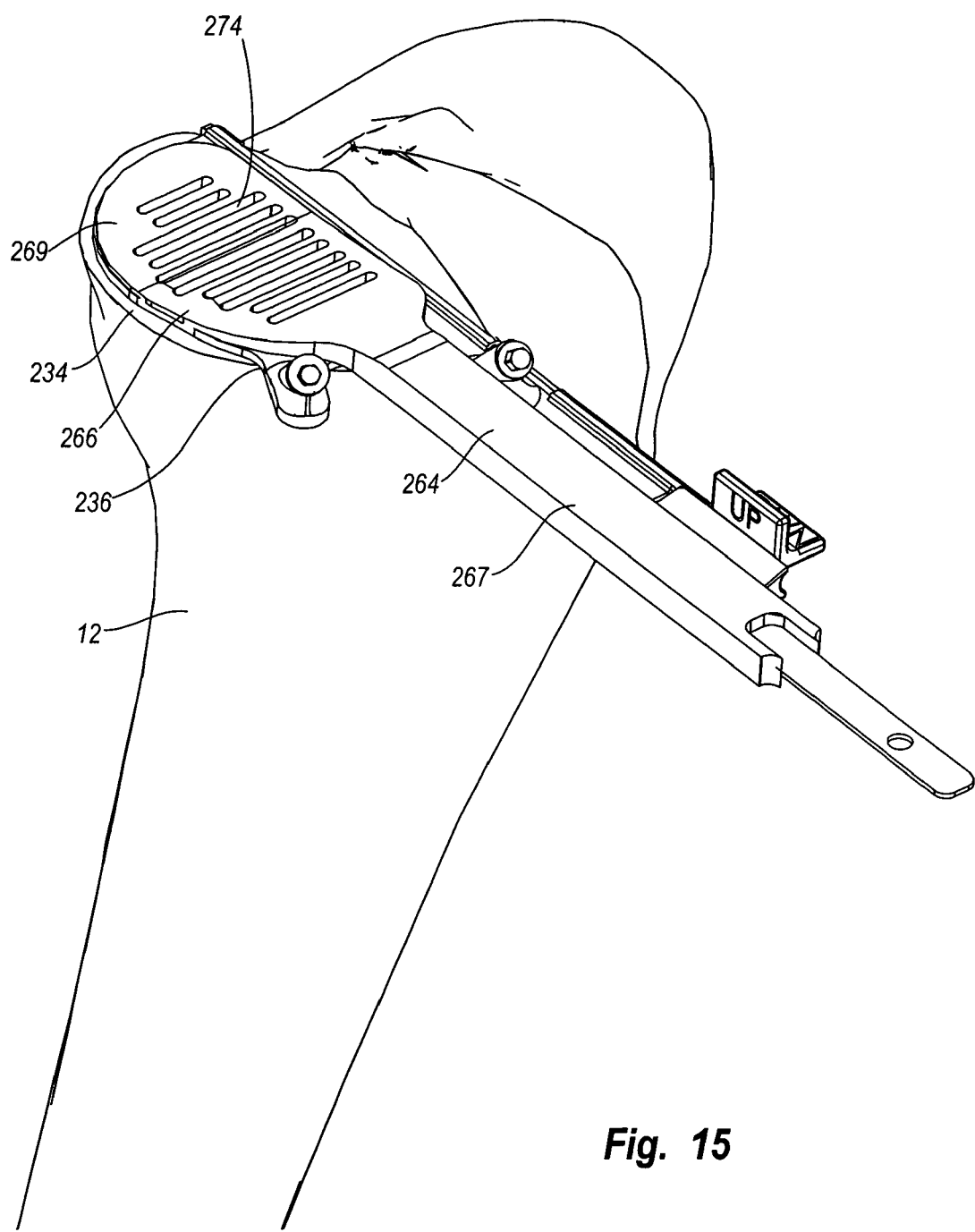
FIG. 15 is a perspective view of a rasp mounted on the guide template shown in FIG. 13.
Figure 16:
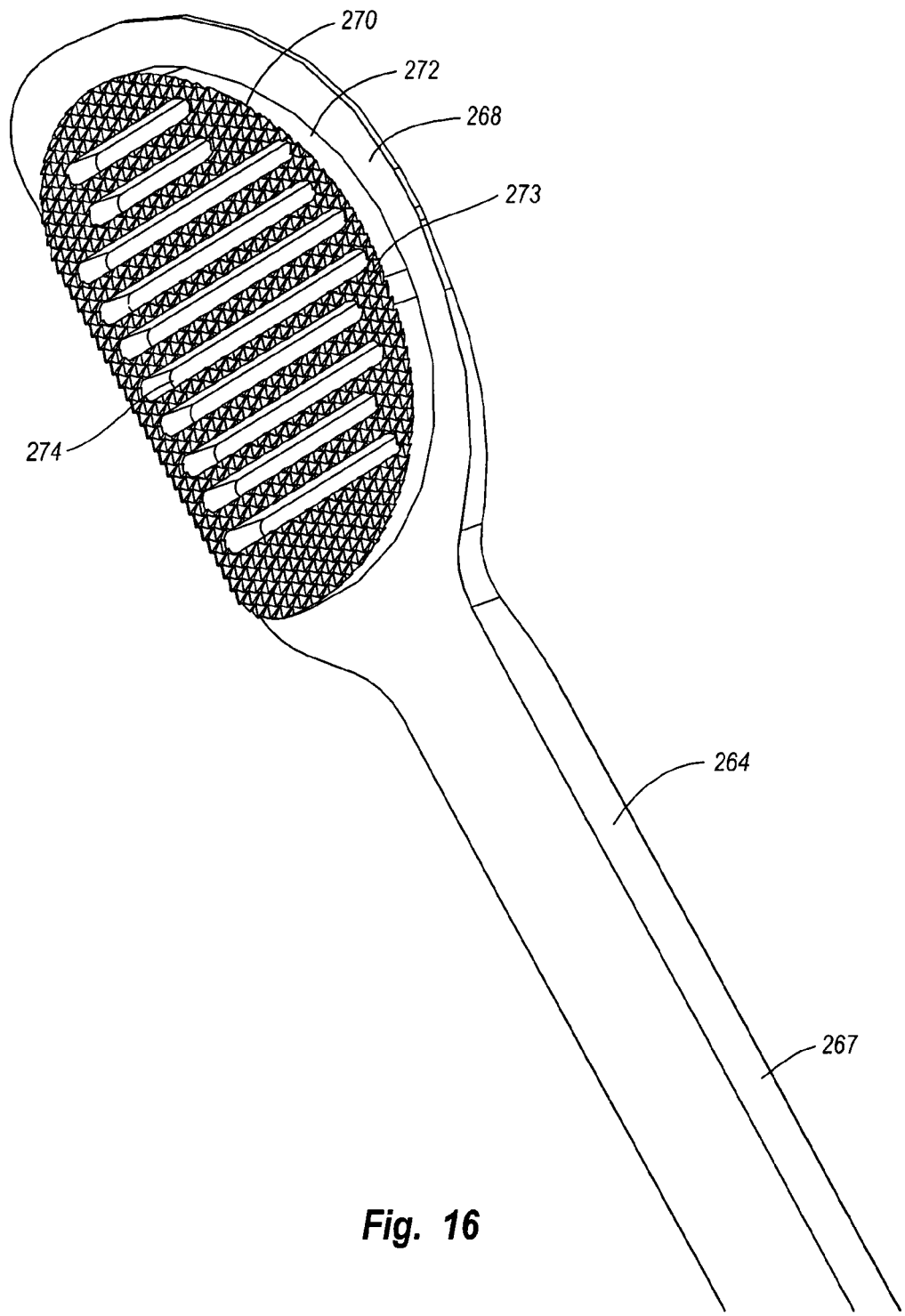
FIG. 16 is a bottom perspective view of the rasp shown in FIG. 15.

Turning to FIG. 15, once guide template 236 is secured in position, a rasp 264 is positioned on guide template 236. As depicted in FIGS. 15 and 16, rasp 264 comprises a head 266 having an elongated handle 267 projecting therefrom. Head 266 includes an inside face 268 and an opposing outside face 269. Projecting from inside face 268 is a cutting mount 270. Counting mount 270 comprises a base 272 projecting from inside face 268 and a plurality of cutting teeth formed on base 272. Cutting mount 270 has a configuration smaller than opening 241 on guide template 236 such that cutting mount 270 can be received within opening 241 as shown in FIG. 15 and can be reciprocated back and forth therein.

In one embodiment, cutting mount 270 reciprocally slides back and forth within opening 241 along a distance in a range between about 3 mm to 15 mm. Other dimensions can also be used. Cutting mount 270 also has a thickness which is greater than the thickness of body 237 of guide template 236. As a result, cutting teeth 237 ride against resected surface 234 when cutting mount 270 is received within opening 241. During the reciprocating movement, guide template 236 functions as a guide for rasp 264 so that only the bone bounded within opening 241 can be removed.

Furthermore, in the embodiment depicted cutting mount 270 is smaller than head 266 such that an openly exposed portion of inside face 268 encircles cutting mount 270. Head 266 has an outer perimeter generally corresponding to the outer perimeter of body 237 of guide plate 236 such that head 266 extends over body 237 when cutting mount 270 is received within opening 241. As such, as cutting mount 270 is reciprocated within opening 241, cutting teeth 273 cut away at the bone bounded within opening 241. The bone is continually cut away until head 266 biases against body 237, thereby precluding further advancement of cutting mount 270 into opening 241. To enable the cut bone particles to escape from opening 241, a plurality of open channels 274 extend through cutting mount 270 and head 266.

It is appreciated that rasp 264 can come in a variety of alternative configurations. For example, instead of having base 272 extend from head 266, cutting teeth 273 could be elongated so as to extend directly from head 266. Likewise, it is not necessary that head 266 outwardly project on all sides of cutting mount 270 so as to overlay guide plate 236. Rather, discrete spaced apart sections of head 266 can be adapted to overlay guide plate 236. In still other embodiments, head 266 can have the same perimeter dimensions as cutting mount 270. In this embodiment, handle 267 would still overlay guide template 236. It is likewise appreciated that the size and arrangement of channels 274 and cutting teeth 273 can be modified in a variety of different configurations.

Figure 17:
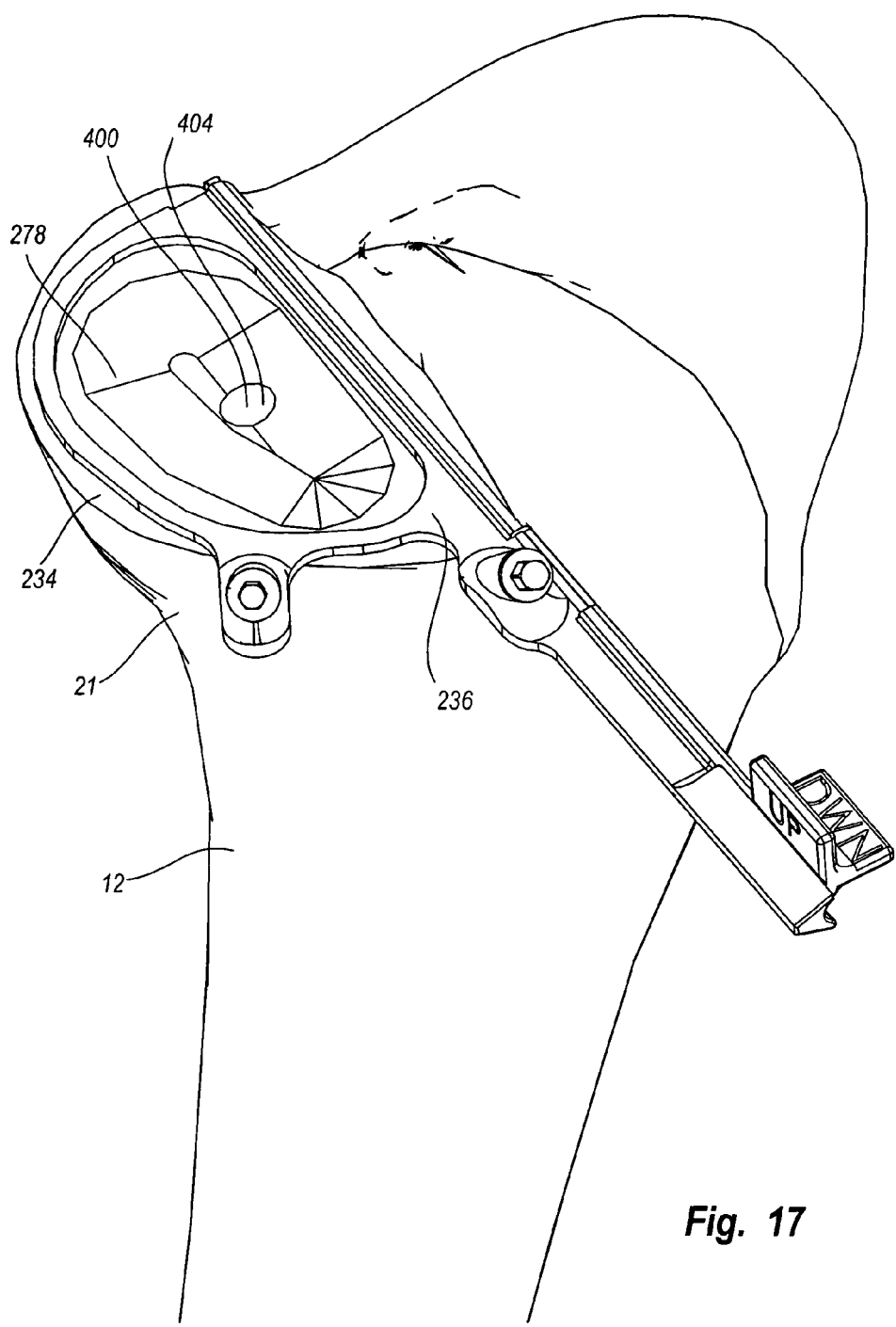
FIG. 17 is a perspective view of the tibia shown in FIG. 13 after the rasp is removed.

In one embodiment, cutting mount 270 has a rounded bottom surface that outwardly curves front to back and side to side. As a result, as depicted in FIG. 17, once rasp 264 is removed, a rounded pocket 278 is formed on resected surface 234. It is appreciated that cutting mount 270 can have a variety of different configurations so as to form pocket 278 of a corresponding shape. As will be discussed below in greater detail, pocket 278 is configured to provide a best fit for mounting the implant. In alternative embodiments where the bottom of the implant is substantially flat, rasp 264 need not be required in that resected surface 234 can be positioned at the desired level to receive the implant. Alternatively, rasp 264 can be formed so that cutting mount 270 has a substantially flat face. In yet other embodiments, cutting mount 270 can be configured to form grooves, channels, slots or the like to fit corresponding projections extending from the implant.

Once the bone surface is prepared to receive the implant, a tunnel 400 is formed intersecting with pocket 278 so that the implant can be mounted. Guide assembly 30, as previously discussed with regard to FIGS. 2 and 3, can be used to form tunnel 400 either before or after the formation of pocket 278 in the same way that tunnel 90 was formed.

Figure 18:
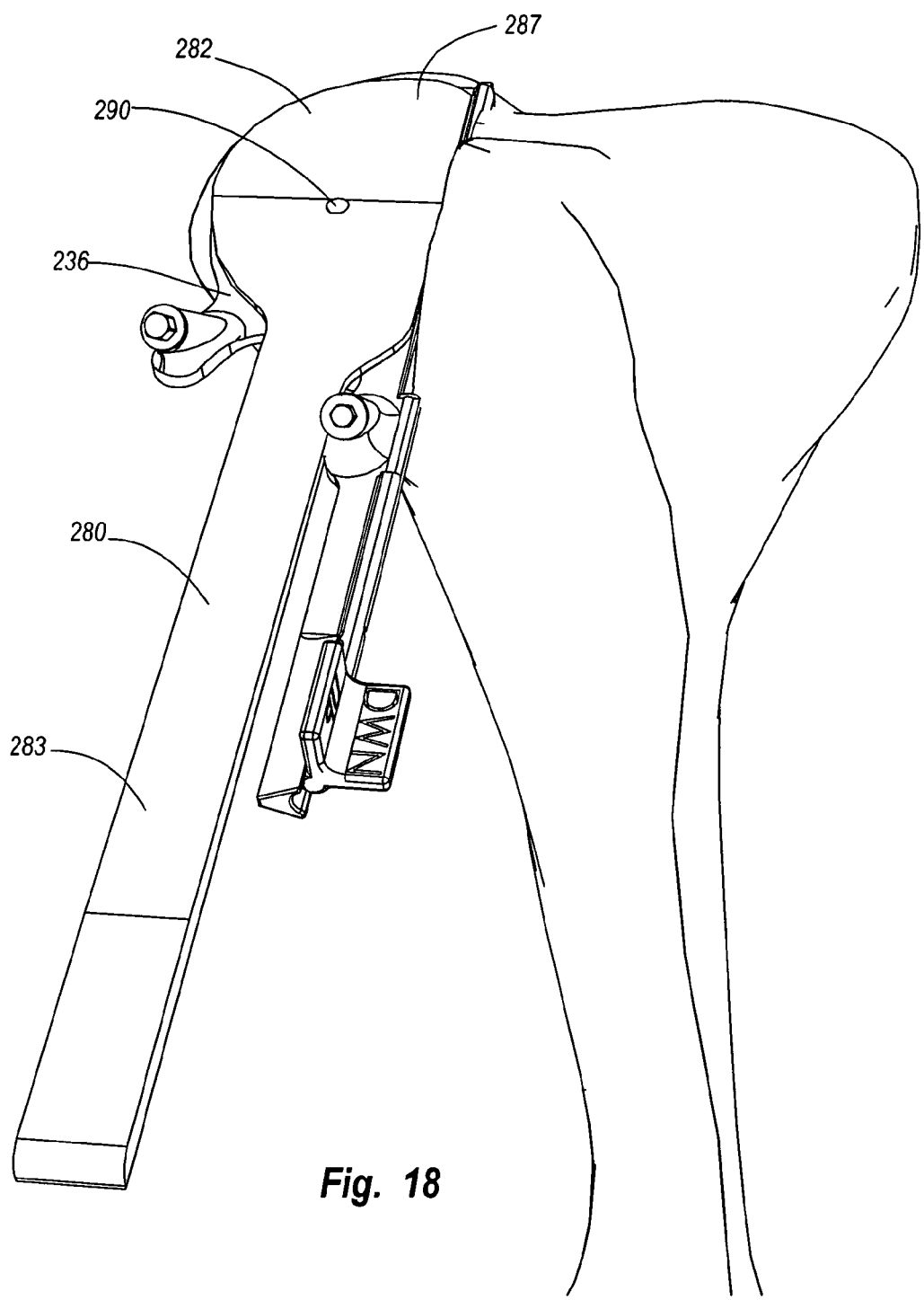
FIG. 18 is a perspective view of a centering template mounted on the guide template shown in FIG. 17.
Figure 19:
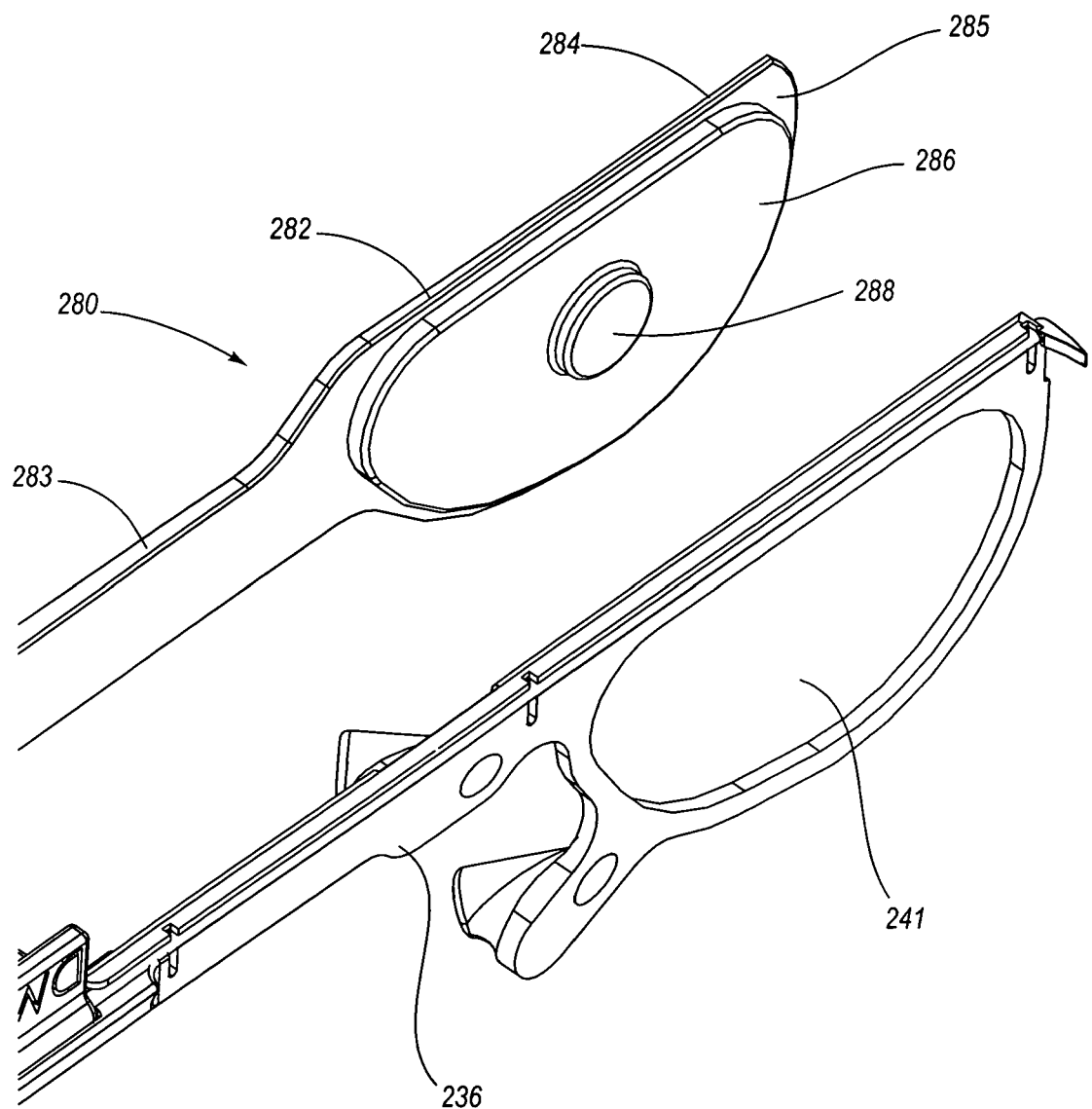
FIG. 19 is a bottom perspective view of the centering template and guide template shown in FIG. 18.

In an alternative method, a centering template 280 is mounted on guide template 236. As depicted in FIGS. 18 and 19, centering template 280 comprises a mounting plate 282 having an elongated handle 283 projecting therefrom. Mounting plate 282 comprises an upper plate 284 having an inside face 285. Projecting from inside face 285 is a boss 286. Boss 286 has a configuration complimentary to opening 241 of guide template 236. Furthermore, boss 286 is slightly smaller than inside face 285 of upper plate 284. As a result, when boss 286 is received within opening 241, as shown in FIG. 18, upper plate 284 extends over a portion of guide plate 236. This coupling provides a fixed positioning of centering template 280 relative to guide template 236. Projecting from boss 286 is a contact boss 288. Contact boss is positioned so as to be located over the intended opening for tunnel 400. This location is typically at the center of resected surface 234. Other locations, however, can also be used. As will be discussed below in greater detail, contact boss 288 acts in part as a stop for the drill forming tunnel 400 within tibia 12 so that the drill does not damage the femur.

As depicted in FIG. 18, formed on outside face 287 of upper plate 284 in vertical alignment with contact boss 288 is a centering indent 290. As discussed below in greater detail, centering indent 290 is used in association with a tunnel guide for positioning the placement of tunnel 400.

Figure 20:
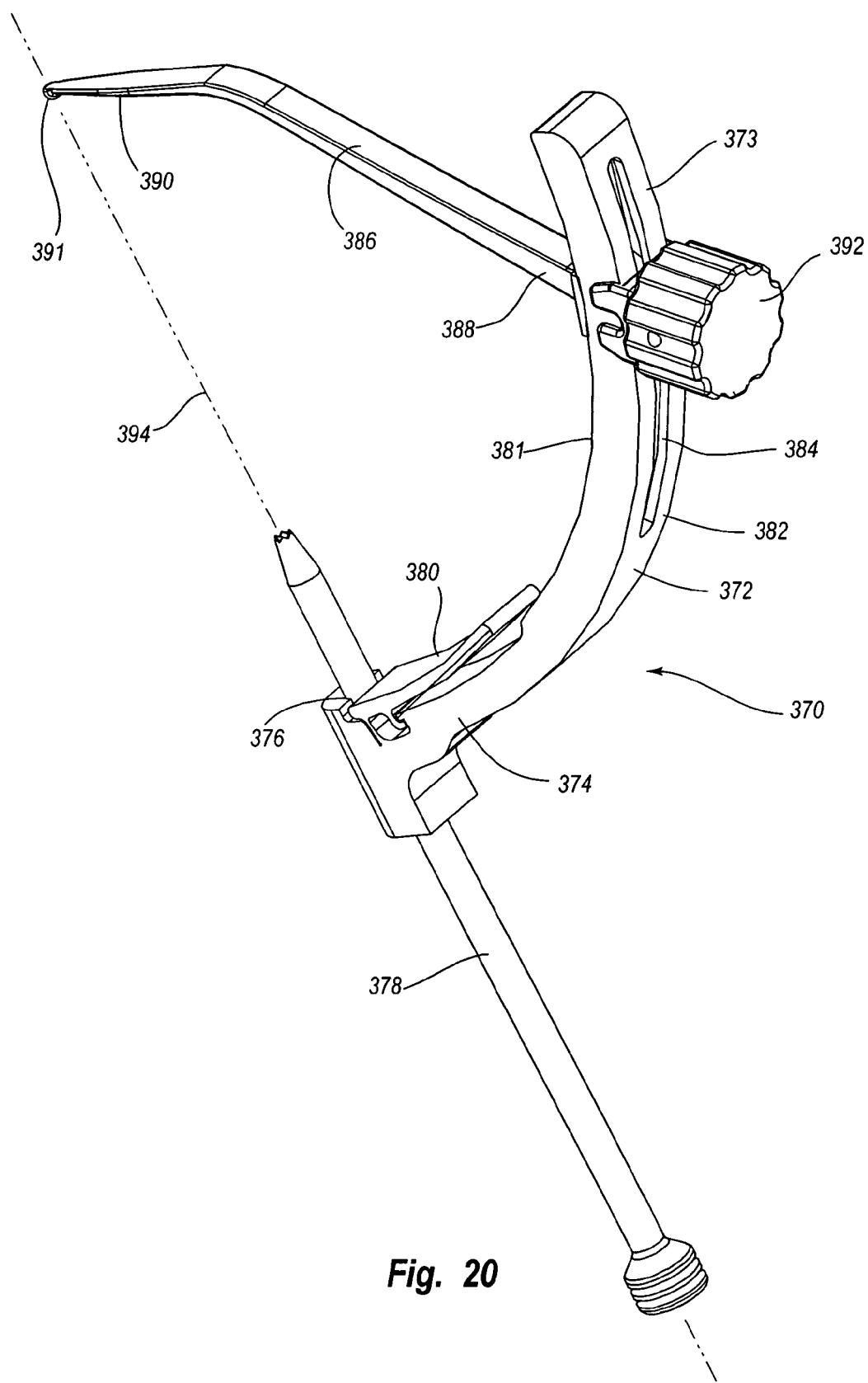
FIG. 20 is a perspective view of a tunnel guide.

Depicted in FIG. 20 is one embodiment of a tunnel guide 370 incorporating features of the present invention. Tunnel guide 370 comprises a brace 372 having an inside face 382 and an opposing outside face 383 that each extend between a first end 373 and an opposing second end 374. Second end 374 has a channel 376 extending therethrough. Sideably disposed within channel 376 is a tubular guide sleeve 378. A clamp arm 380 is coupled with brace 372 and resiliently biases against guide sleeve 378. As such, by depressing clamp arm 380, guide sleeve 378 can be selectively slide to a desired location and then secured in position by release of clamp arm 380. An elongated slot 384 extends along the length of brace 372 at first end 373 and extends between inside face 381 and outside face 382.

Tunnel guide 370 further comprises an elongated alignment arm 386 having a first end 388 slidably disposed within slot 384 and an opposing second end 390. Second end 390 terminates at a rounded tip 391. An adjustment knob 392 threadedly engages first end 388 of alignment arm to brace 372. Rotation of adjustment knob 392 in a first direction allows second end of alignment arm 386 to freely slide along slot 384. By rotating adjustment knob 392 in the opposing direction, alignment arm 386 is rigidly clamped to brace 372. It is noted that guide sleeve 378 has a central longitudinal axis 394 extending therethrough. Tunnel guide 370 is configured such that independent of the placement of alignment arm 386 along slot 384, axis 394 is always aligned with tip 391.

Figure 21:
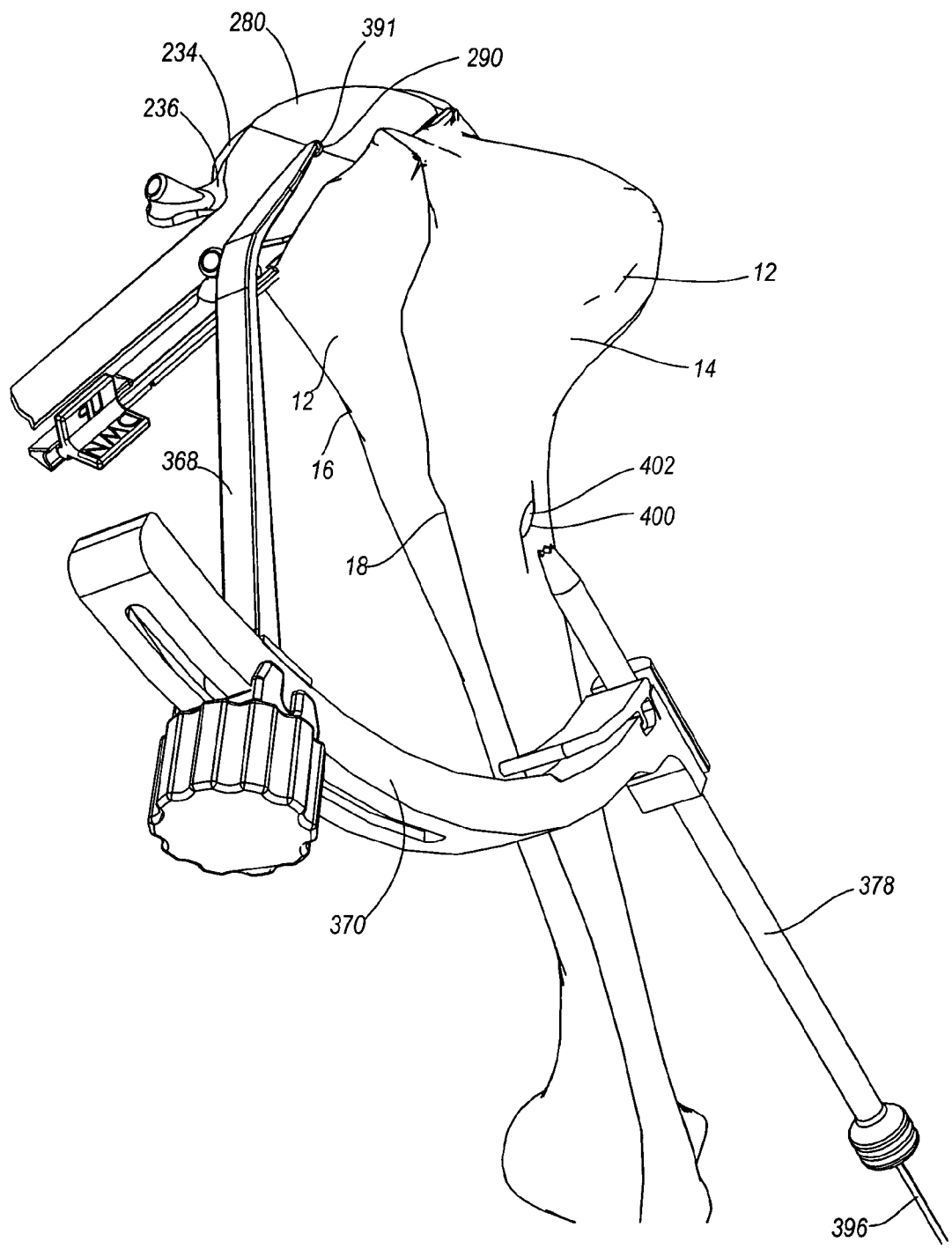
FIG. 21 is a perspective view of the tunnel guide of FIG. 20 mounted on the centering template and tibia shown in FIG. 18.

As depicted in FIG. 21, during operation tip 391 of alignment arm 386 is received within indent 290 of centering template 280. Because guide sleeve 378 is always aligned with tip 391, the surgeon is now free to bias the distal end of guide sleeve 378 at any location on tibia 12 for which tunnel guide 370 can be adjusted. It is understood that tunnel 400 will extend through tibia 12 between the location where the distal end of guide sleeve 378 is position and pocket 278 formed on resected surface 234. The surgeon is thus free to select the best location on tibia 12 for forming the tunnel. Such selection can take into consideration the area of best bone quality and the desired length and position for tunnel 400. In the present embodiment, where the implant is being mounted on the medial condyle 21, guide sleeve 378 is shown being biased against lateral side 14 of tibia 12. In alternative embodiments, it is also appreciated that guide sleeve 378 can be biased against anterior side 18 or medial side 16 of tibia 12.

Once guide sleeve 378 is biased against tibia 12, a guide wire 396 is passed through guide sleeve 378 and then drilled through tibia 12 until guide wire 396 contacts boss 288 (FIG. 19). As a result, a tunnel 400 is formed having a first end 402 located at a position spaced apart from resected surface 234 and a second end 404 (FIG. 17) which extends through pocket 278 on resected surface 234. As discussed below in greater detail, tunnel 400 receives a flexible line that is mounted to the implant. In one embodiment, passing the flexible line through tunnel 400 requires tunnel 400 to have a diameter typically in a range between 1 mm to about 3 mm. Of course, larger diameters can also be used. Accordingly, depending on the desired size for tunnel 400, guide wire 396 can be used to independently form tunnel 400. Alternatively, a tubular drill sleeve can be positioned over guide wire 396 to enlarge tunnel 400. Alternatively, guide wire 396 can be removed and a larger drill can be passed through the preliminary tunnel formed by the guide wire 396 to form the final tunnel 400.

As will be discussed below in greater detail, a bone anchor is secured within first end 402 of tunnel 400. The bone anchor requires a larger opening than what is necessarily needed for the line to pass through tunnel 400. Accordingly, where the tunnel 400 is minimized to limit bone removal, first end 402 of tunnel 400 is counter bored with a larger drill so as to enable proper placement of the bone anchor. In one embodiment, tunnel 400 can be counter sunk so as to have a diameter in a range between about 4 mm to 8 mm. Again, other dimensions can also be used.

Once tunnel 400 is formed, tunnel guide 370, centering template 280, and guide template 236 are removed from tibia 12. Accordingly, by using any of the aforementioned methods and/or combinations thereof, a resected medial condyle having a tunnel coupled therewith, is now ready to receive an implant.

Figure 22A:
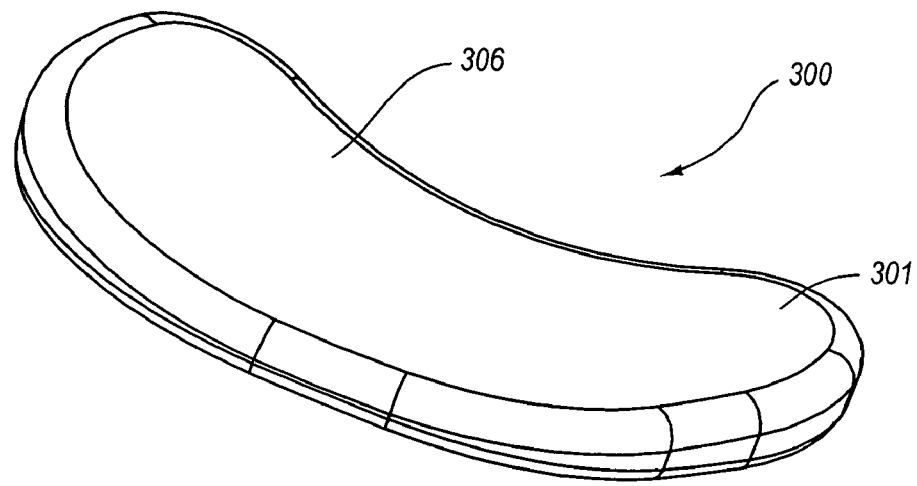
FIG. 22A is a top perspective view of a condylar implant.
Figure 22B:
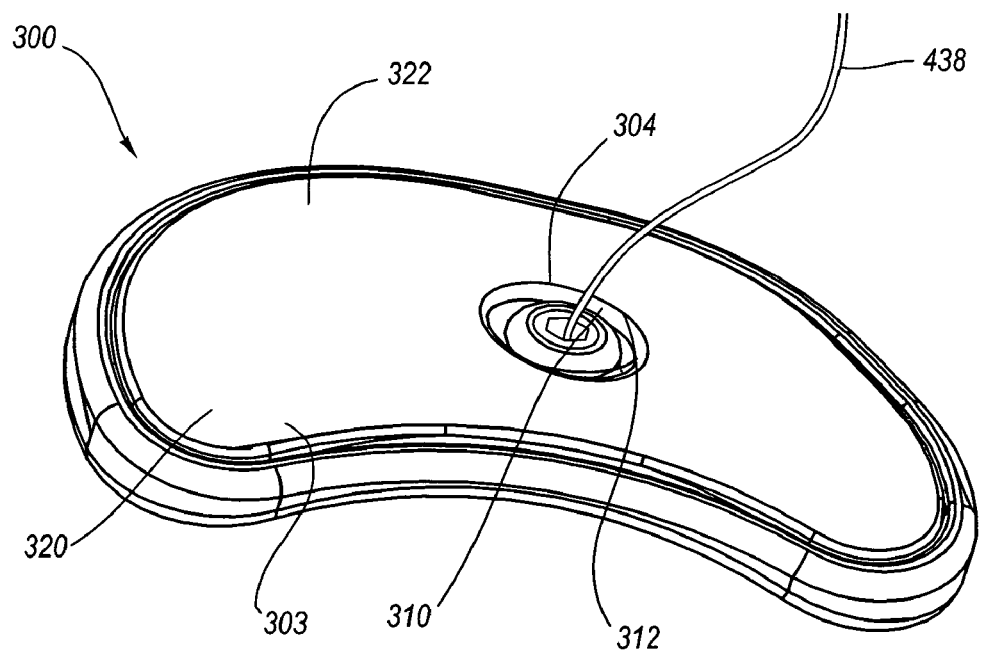
FIG. 22B is a bottom perspective view of the condylar implant shown in FIG. 22A.
Figure 22C:
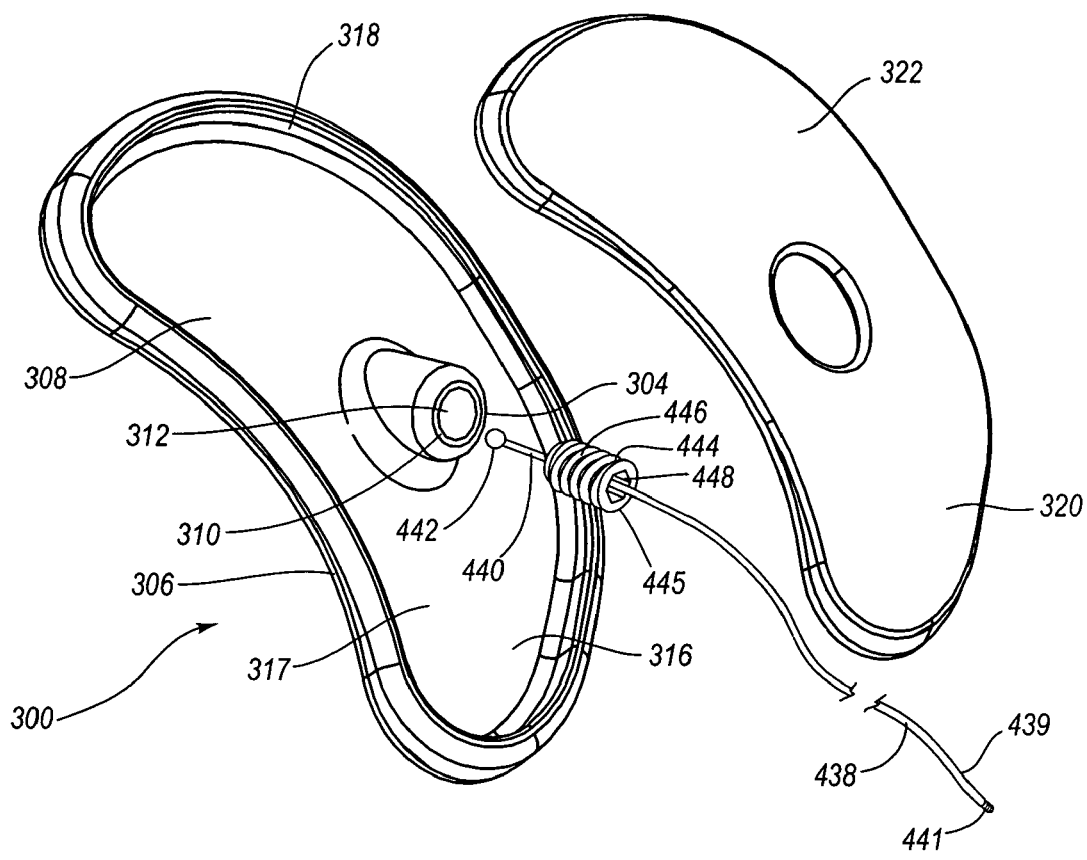
FIG. 22C is an exploded perspective view of the condylar implant shown in FIG. 22B.

Depicted in FIGS. 22A-22C is one embodiment of a condylar implant 300 incorporating features of the present invention. The term "condylar implant" is broadly intended to include implants that can replace all or a portion of a condyle of a tibia. The condylar implant can also replace all or a portion of the articulation surface of the condyle. Accordingly, while the depicted embodiments show one conventional size and configuration for a condylar implant, in alternative embodiments the condylar implant can be larger to replace more of the tibia or can be smaller to replace only a section of a condyle of a tibia. In such alternatives, the condylar implant can have a variety of different configurations.

In general, condylar implant 300 has a top articular surface 306 and an opposing bone apposition surface 303. In one embodiment, top articular surface 306 has a generally concave contour so as to mate with a corresponding femoral condyle. Alternatively, articular surface 306 can be substantially flat. Bone apposition surface 303 has a generally convex contour that curves front to back and side to side and that is configured to mate with pocket 278 on resected surface 234 (FIG. 17). As a result of contouring bone apposition surface 303, implant 300 can be formed having a low profile configuration with a generally uniform thickness along the length thereof. This uniform thickness provides uniform strength for implant 300. Furthermore, by contouring implant 300 to fit within pocket 278, the stability of mounted implant 300 is increased so as to prevent unwanted movement of implant relative to tibia 12.

In alternative embodiments, bone apposition surface 303 can be substantially flat. As a result, implant 300 can be mounted directly on flat resected surface 234. In this embodiment, however, contouring of articular surface 306 would result in the opposing ends of implant 300 being thicker than the middle. Again, however, depending on the size of the patient and the portion of the bone being replaced, implant 300 can have an array of different sizes and configurations.

As depicted in FIG. 22C, implant 300 comprises a body 301 and an inlay 320. Body 301 has top articular surface 306 and an opposing bottom surface 308. A pocket 316 is recess on bottom surface 308. Pocket 316 is bounded by a floor 317 and a sidewall 318 upstanding around the perimeter thereof. A stem 304 projects from floor 317 and is completely encircled by pocket 316. Body 301 is typically comprised of a metal such as chromium, cobalt, titanium, or the like and alloys thereof but can also be made of ceramics, plastics, or other materials. Body 301 can also be comprised of layers or sections of different materials. In one embodiment, body 301 has a maximum thickness typically in a range between about 2 mm to about 10 mm. Other dimensions can also be used depending on the amount that the tibial condyle is resected or worn away.

Inlay 320 is secured within pocket 316 of body 301 so as to encircle stem 304. Inlay 320 is comprised of a porous bone ingrowth material such as porous tantalum. Other conventional porous bone ingrowth materials can also be used. Inlay 320 is secured within pocket 316 using conventional techniques such as press fit, welding, adhesive, sintering, and the like. Inlay 320 can also be mechanically connected to body 301 such as by screws, fasteners, rivets, or the like. In alternative embodiments, pocket 316 can be eliminated and inlay 320 can be secured to the bottom surface of body 301 using various techniques. Inlay 320 has an exposed bottom surface 322 that, as discussed above, can be arched, substantially flat, or can have any other desired configuration. In this embodiment, bottom surface 322 of inlay 320 comprises substantially all of bone apposition surface 303 of base plate 301.

Figure 23A:
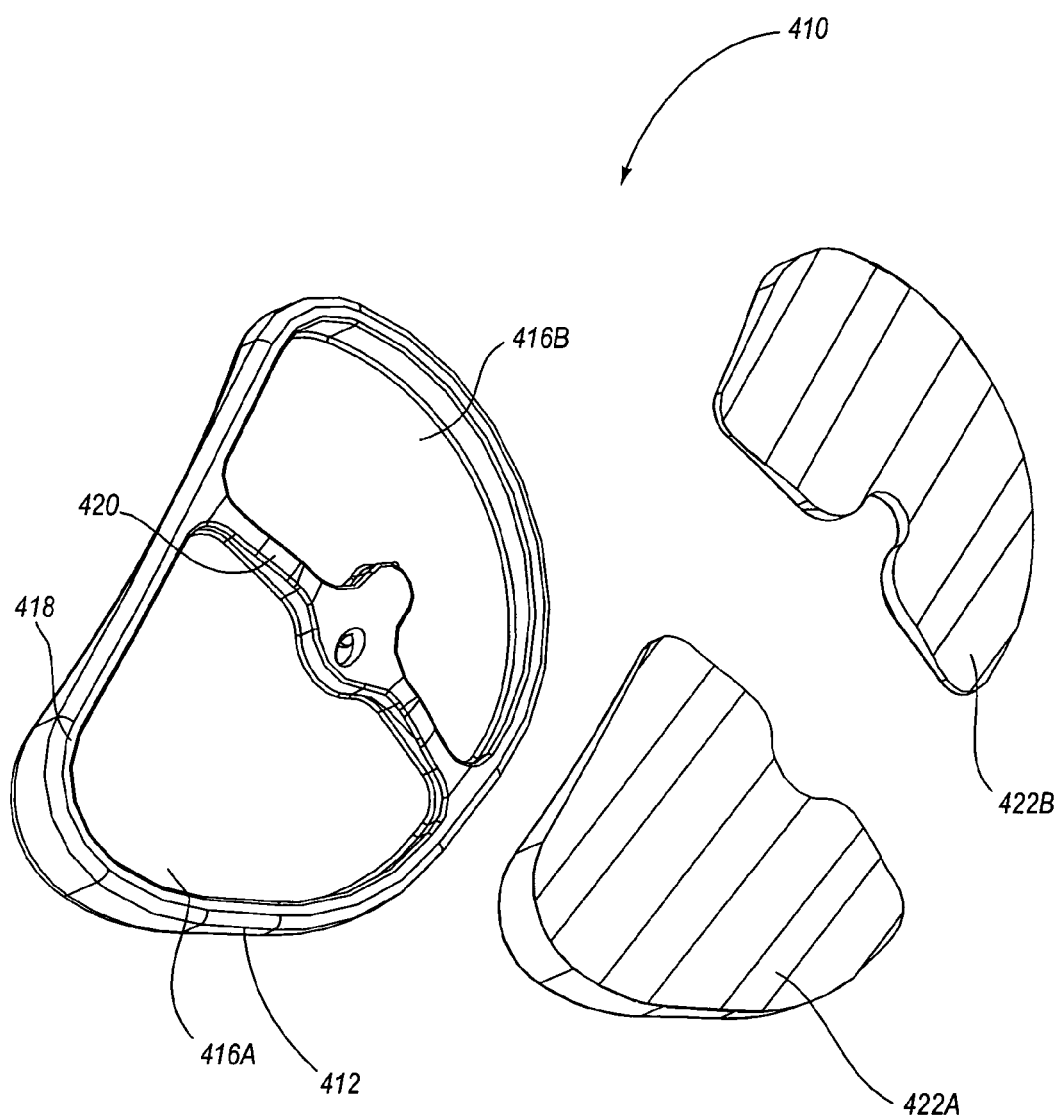
FIG. 23A is an exploded perspective view of an alternative embodiment of a condylar implant having two pockets.

In contrast to having a single pocket 316 in which a single inlay 320 is positioned, it is appreciated that body 301 can be formed having a plurality of pockets each adapted to receive a separate inlay. For example, depicted in FIGS. 23A and B is an alternative embodiment of an implant 410 comprising a body 412 having a bottom surface 414. Bottom surface 414 is formed with two pockets 416A and B which are partially bounded by a perimeter sidewall 418 and are separated by a central bridge 420. Each pocket 416A and B is adapted to receive a corresponding inlay 422A and B. In this embodiment, the bone apposition surface includes not only the bottom surface of inlays 422A and B but also the bottom surface of bridge 420 and perimeter sidewall 418.

Figure 24:
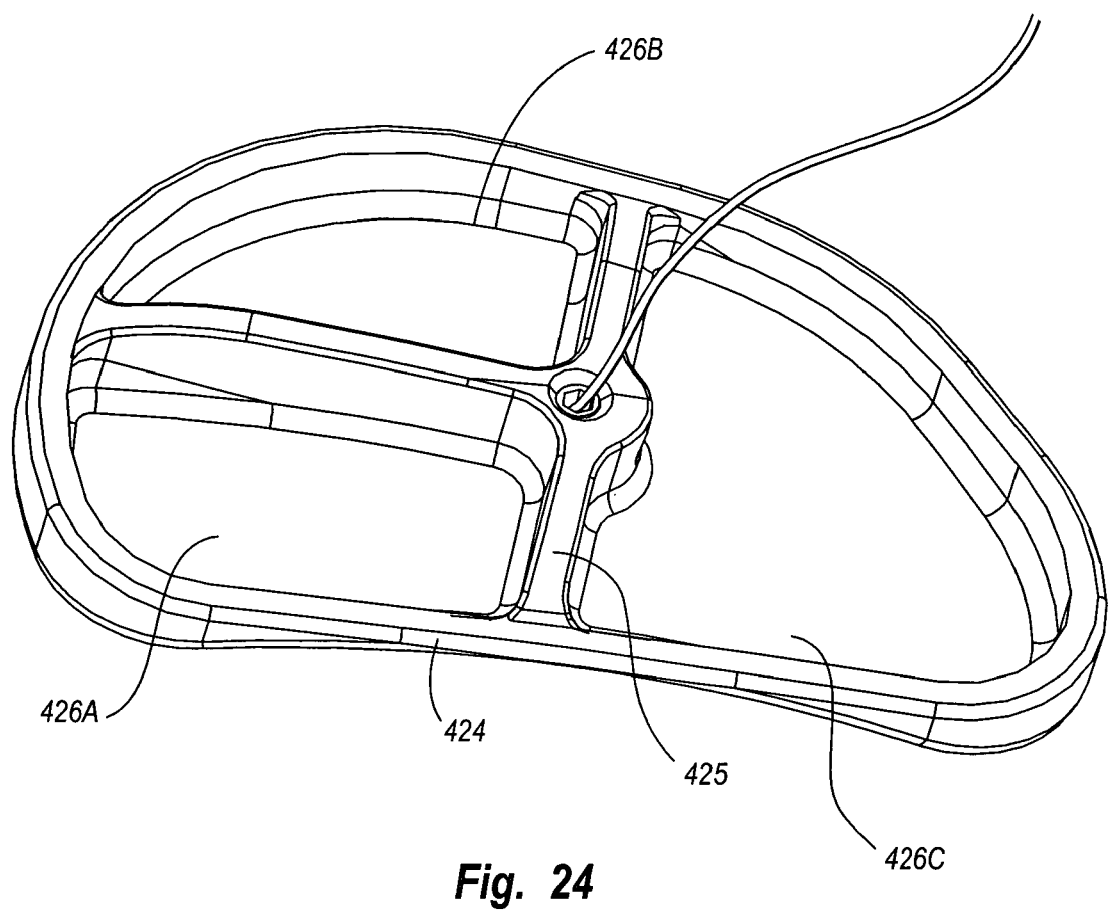
FIG. 24 is a bottom perspective view of another alternative embodiment of a condylar implant having three pockets.

Similarly, depicted in FIG. 24 is an alternative embodiment of a body 424 for an implant. Body has a bottom surface 424 with three separate pockets 426A, B, and C. Each of the pockets 426 is adapted to receive a separate inlay. The bridges formed between the separate pockets provide increased structural support for the implant and, as will be discussed below in greater detail, provide a structure on which the flexible line can be attached.

Figure 25:
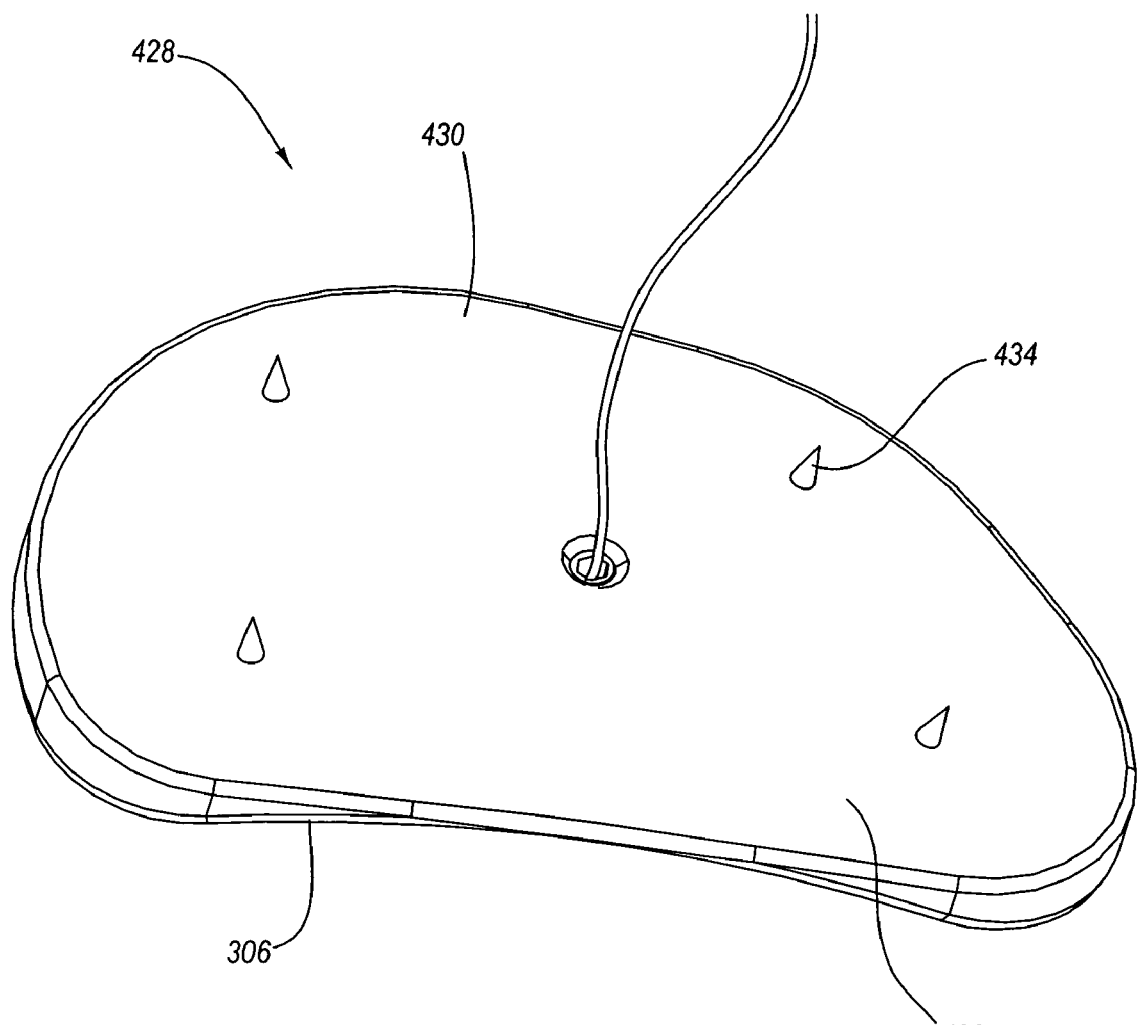
FIG. 25 is a perspective view of a unitary condylar implant having spikes formed thereon.

In still other embodiments, it is appreciated that the inlay of porous bone ingrowth material can be eliminated. In this embodiment, the condylar implant can comprise a single integral member. For example, depicted in FIG. 25 is an alternative embodiment of a condylar implant 428. Implant 428 is formed as a single integral body 430 having top articular surface 306 and an opposing bottom surface 430 which also functions as the bone apposition surface. To facilitate secure attachment of implant 428 to tibia 12, a plurality of spikes 434 are formed on bottom surface 430. It is appreciated that in all of the embodiments herein that spikes, fins, or other forms of projections can also be formed projecting from bottom surface of the implant. Such projections can be separated from or encircled by the porous bone ingrowth inlay. The projections can also be formed on the porous bone ingrowth inlay. Such projections can penetrate into the tibia or be received within slots formed on the tibia to help prevent unwanted movement of the implant.

As previously mentioned, flexible line is used to secure the implants to tibia 12. As used in the specification and append claims, the term "line" is broadly intended to include wire, cable, cord, suture, braded line, combinations thereof or any other type of flexible filament. The line can be made of metal, alloys, synthetics, composites, or any other desired material. In one embodiment of the present invention the line comprises braded filaments of a cobalt chrome alloy having a diameter in a range between about 0.25 mm to about 5 mm with about 0.5 mm to about 3 mm being more common and about 0.5 mm to about 2 mm being most common. Other dimensions can also be used. The line can be of any desired length.

In one embodiment, the line can also be defined in that for an unsupported length of line of 4 cm, the line has substantially no compressive strength. In yet other embodiments, for an unsupported length of line of 4 cm, the line fails under buckling when an axial compressive load of 0.25 N, 1 N, 2 N, 5 N, 20 N, or 50 N is applied. That is, different lines can be used that fail under different loads. Stiffer lines can also be used.

It is also appreciated that the line can be static or resiliently stretchable. In one embodiment where the line is resiliently stretchable, the line can be comprised of a material have shape memory of pseudo elastic properties. One example of such a material is a nickel titanium alloy sold under the name Nitinol. In yet other embodiment, it is appreciated that sections of the line could be replaced with a spring member such as a coiled spring or rubber or bungee type member.

Returning to FIGS. 22B and C, an elongated line 438 is provided having a first end 439 and an opposing second end 440. First end 439 terminates at a tip 441 that is sealed so as to have and maintain a smooth uniformed diameter. Second end 440 terminates at an enlarged rounded head 442. In alternative embodiments, second end 440 can have the same configuration as first end 439 or can have an enlarged head of any desired configuration.

In one embodiment of the present invention, means are provided for connecting flexible line 438 to implant 300. By way of example and not by limitation, stem 304 is provided with a threaded socket 312. Slidably disposed on line 438 is a tubular retainer 444. Retainer 444 comprises a body 445 having one or more helical threads 446 mounted on the exterior surface thereof. Threads 446 are configured to engage with threaded socket 312. A channel 448 longitudinally extends through body 445. Channel 448 constricts toward the distal end of body 445 so that the channel 448 thereat is larger than the diameter of line 438 but smaller than the diameter of head 442. The proximal end of channel 448 is enlarged and has a polygonal transverse cross section. As a result, first end 439 of line 438 can be passed through channel 448 of body 445 distal to proximal. Line 438 can then be pulled through retainer 444 until head 442 is stopped by the constricted section of channel 448. The first end of line 438 can then be advanced through a central channel in a tubular driver (not shown) having a free end adapted to fit within channel 448 of retainer 444 at the proximal end thereof. The driver can thus be used to screw retainer 444 into threaded socket 312, thereby securing line 438 to implant 300.

Figure 23B:
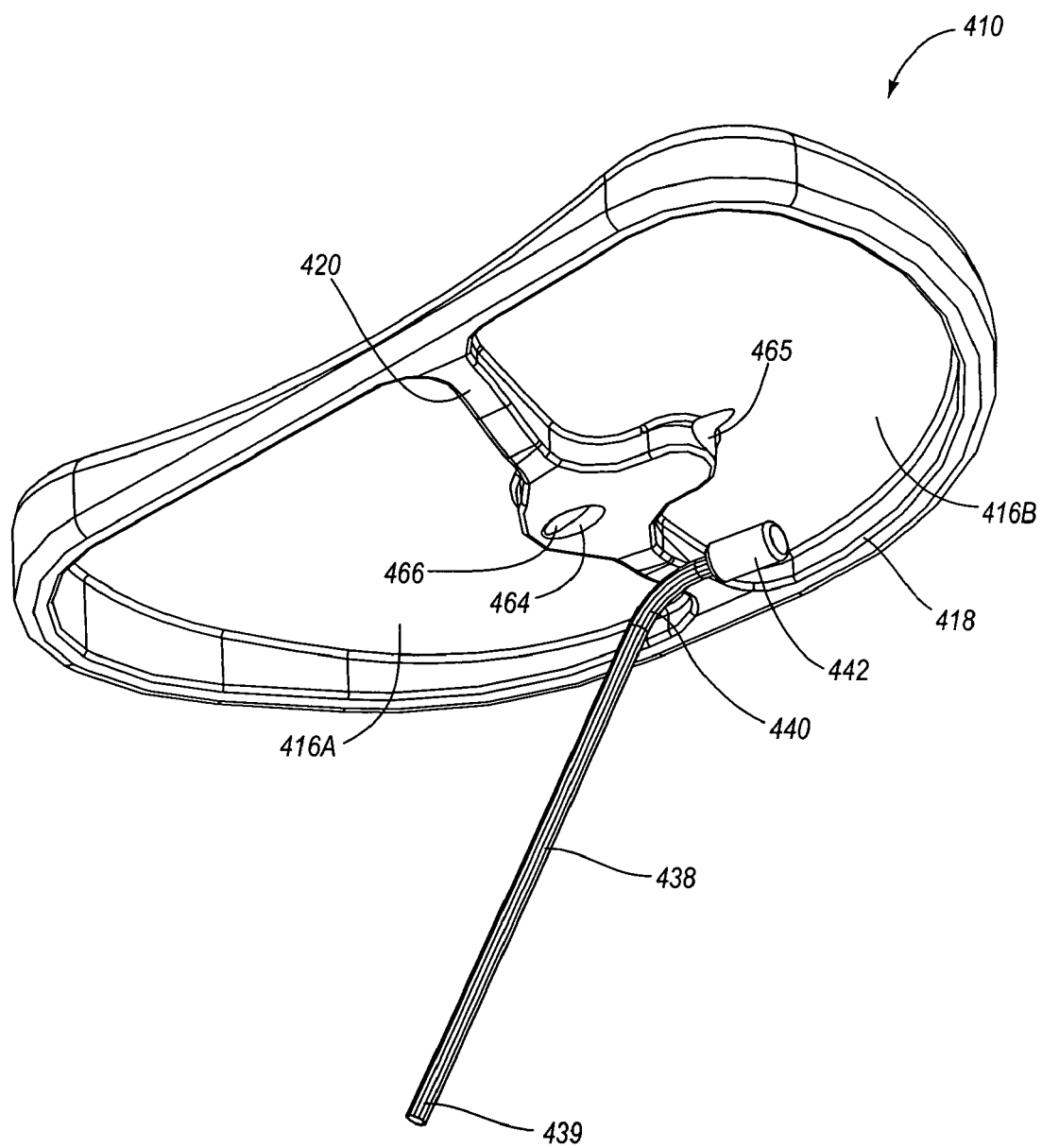
FIG. 23B is a bottom perspective view of the implant shown in FIG. 23A with a line for connecting thereto.

Depicted in FIG. 23B is another embodiment of the means for connecting a line to an implant. In this embodiment a passage 464 extends through bridge 420. Passage 464 has an entrance 465 formed on a side wall of bridge 420 and an exit 466 formed on a bottom surface of bridge 420. Again, passage 464 constricts as it extends from entrance 465 to exit 466. Line 438 is shown having an enlarged substantially cylindrical head 442 formed on second end 440. Head 442 is larger than the constricted portion of passage 464. Head 442 can be crimped, welded, or otherwise formed on line 438. Head 442 can also be integrally formed with line 438. During assembly, first end 439 of line 438 is passed through passage 464 from entrance 465 to exit 466. Line 438 is advanced through passage 464 until head 442 is captured and securely retained within constricted passage 464. Inlays 422A and B can then be positioned within pockets 416A and B. In yet other embodiments, rather than constricting passage 464, it is appreciated that head 442 can be wedge shaped so that head 442 is captured within passage 464.

Figure 26:
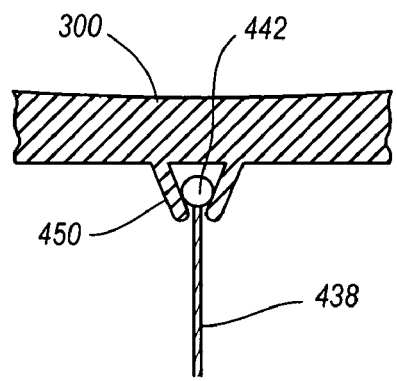
FIG. 26 is a cross sectional side view showing a wire attached to an implant by crimping.
Figure 27:
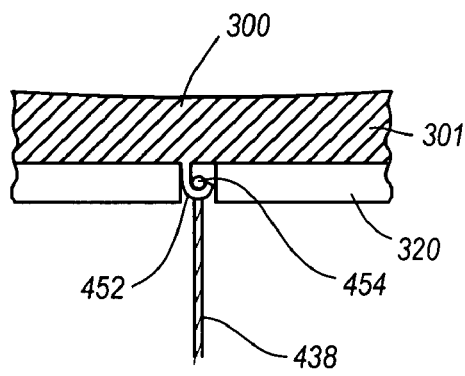
FIG. 27 is a cross sectional side view showing a wire attached to an implant by looping around a hook.

Depicted in FIGS. 26-31 are a variety of still other embodiments of the means for connecting a line to an implant. Specifically, depicted in FIG. 26 is a stem 450 mounted to implant 300 which can be selectively crimped so as to catch head 442 within stem 450. In one embodiment this can be accomplished by forming slots along stem 450. Depicted in FIG. 27, a hook 452 is formed projecting from the bottom surface of body 301 of implant 300. In contrast to having head 442, a loop 454 is formed at the second end of line 438. Loop 454 is looped around hook 452. Inlay 320 is then mounted on the bottom surface of body 301 so as to prevent loop 454 from accidentally sliding off of hook 452.

Figure 28:
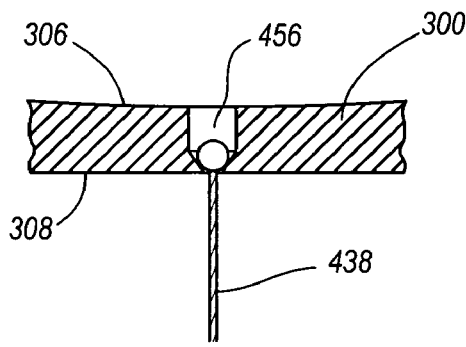
FIG. 28 is a cross sectional side view showing a wire attached to an implant by passing through a constricted opening in the implant.

Depicted in FIG. 28, a channel 456 can be formed extending through implant 300 from top surface 306 to bottom surface 308. Channel 456 is enlarged at top surface 306 so as to receive head 442 of line 438 but constricts toward bottom surface 308 so as to capture head 442 within channel 456. The opening to channel 456 on top surface 306 can be rounded to prevent unwanted wear on the femoral condyle. In other embodiments, a plug can be inserted within channel 456 so as to occlude the opening to channel 456. In still another alternative, instead of forming the opening to channel 456 on top surface 306, a constricted slot can be formed that inwardly extends from the side of implant 300.

Figure 29:
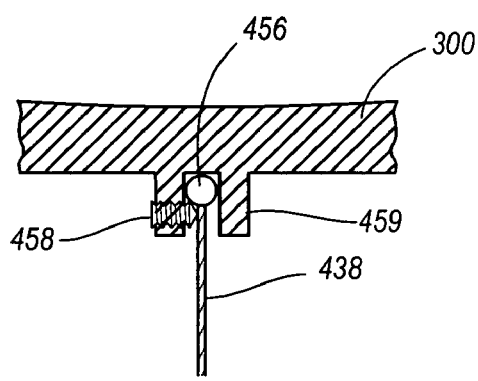
FIG. 29 is a cross sectional side view showing a wire attached to an implant by a set screw.
Figure 30:
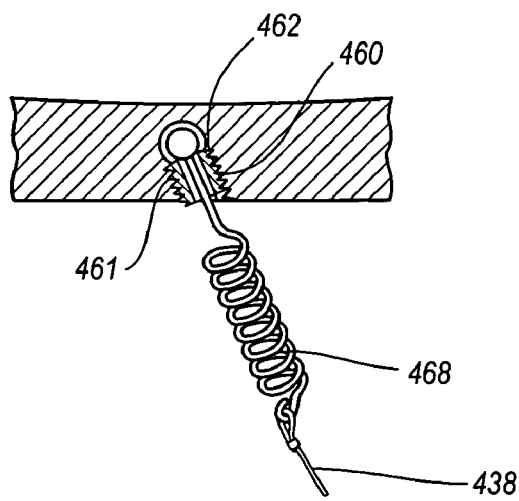
FIG. 30 is a cross sectional side view showing a wire attached to an implant by a barbed retainer.

Depicted in FIG. 29, a set screw 458 is screwed into the side of a tubular stem 459 to capture head 456 therein. Finally, depicted in FIG. 30, rather than having a threaded retainer 444 as discussed above, a tubular retainer 460 can be provided with outwardly projecting barbs 461. Retainer 460 can simply be pushed into a socket 462 having threads or barbs thereon so that retainer 460 is captured therein. It is also noted that in FIG. 30 line 438 is shown comprising a resiliently stretchable spring 468. It is appreciated the spring 468 can be directly connected to the implant or disposed along line 438. Spring 468 can also come a variety of different shapes and sizes and be made from different materials. As will be discussed below in greater detail, spring 468 helps maintain the desired tension force on line 438 so that the implant is securely held in position.

Figure 31:
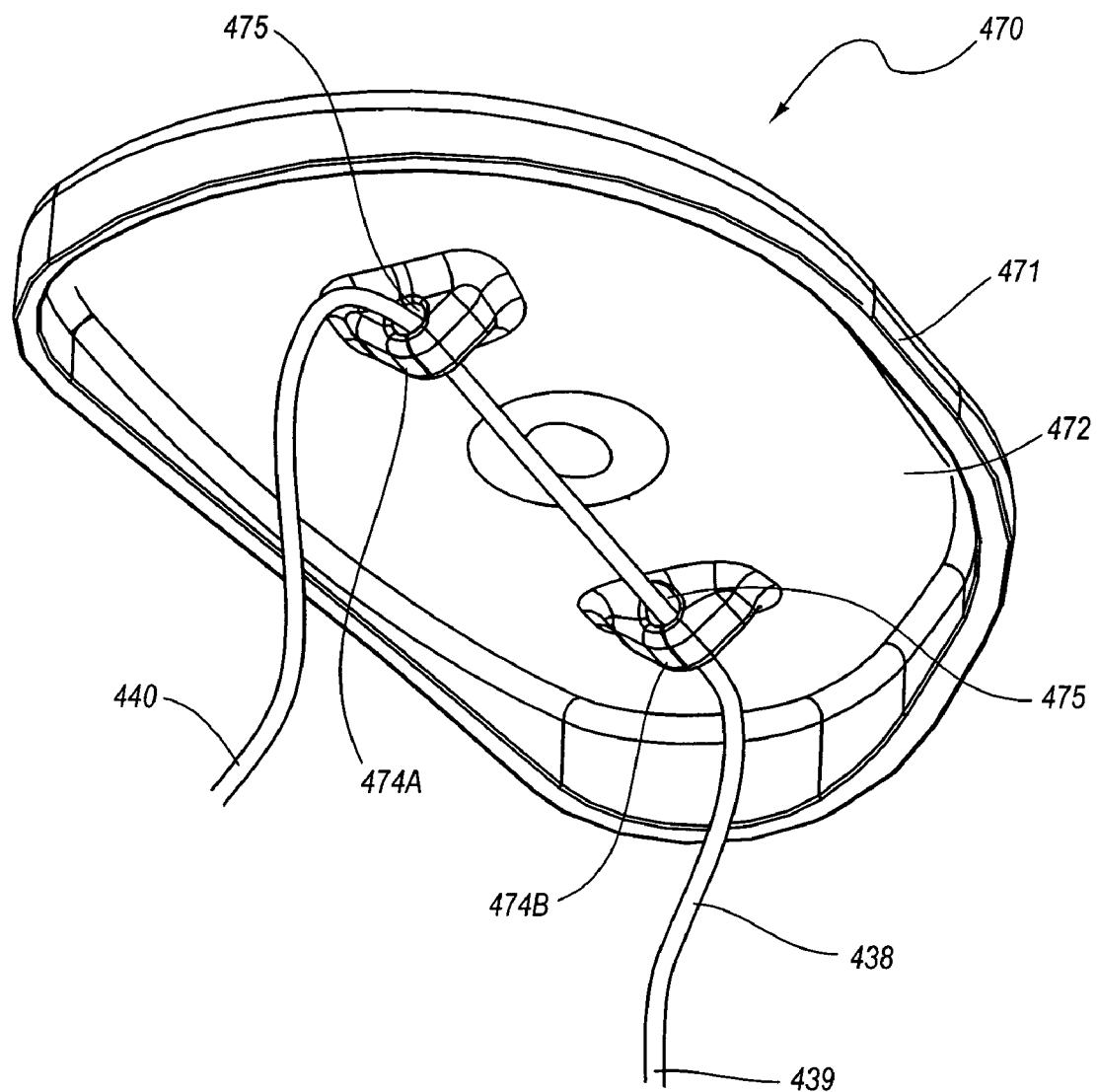
FIG. 31 is a bottom perspective view of an alternative embodiment of an implant having a line slidably connected thereto.

In the embodiment depicted in FIG. 31, an implant 470 has a body 471 with a bottom surface 472. A pair of spaced apart projections 474A and B project from bottom surface 472. A passage 475 extends through each projection 474A and B. Line 438 is passed through each passage 475 so that line 438 is slidably connected to implant 470 with both ends 439 and 440 of line 438 being freely disposed. As will be discussed below in greater detail, in this embodiment both ends 439 and 440 of line 438 are separately connected to the bone. Since line 438 is slidably connected to implant 470, this embodiment functions like a pulley in that a tensioning force applied to one end of line 438 is magnified as is passes through the passages 474. As such, greater force can be used to secure the implant without increasing the load on line 438.

Furthermore, by connecting line 438 to implant 470 at two spaced apart locations, the implant is secured in a more stable configuration that prevents unwanted sliding or rotation on the bone. In other embodiments, it is appreciated that line 438 can be connected to only a single projection 474. It is also appreciated that a first line can be connected to projection 474A while a second line is connected to projection 474B. In like manner, it is appreciated that in all embodiment disclosed herein, two or more discrete lines can be connected two each of the implants using any of the methods disclosed herein. It is also appreciated that there are still a large number of other ways in which line 438 can be secured to an implant. For example, the line can be welded, press fit, or attached by a variety of different types of fasteners such as bolts, rivets, or clamps.

Figure 32A:
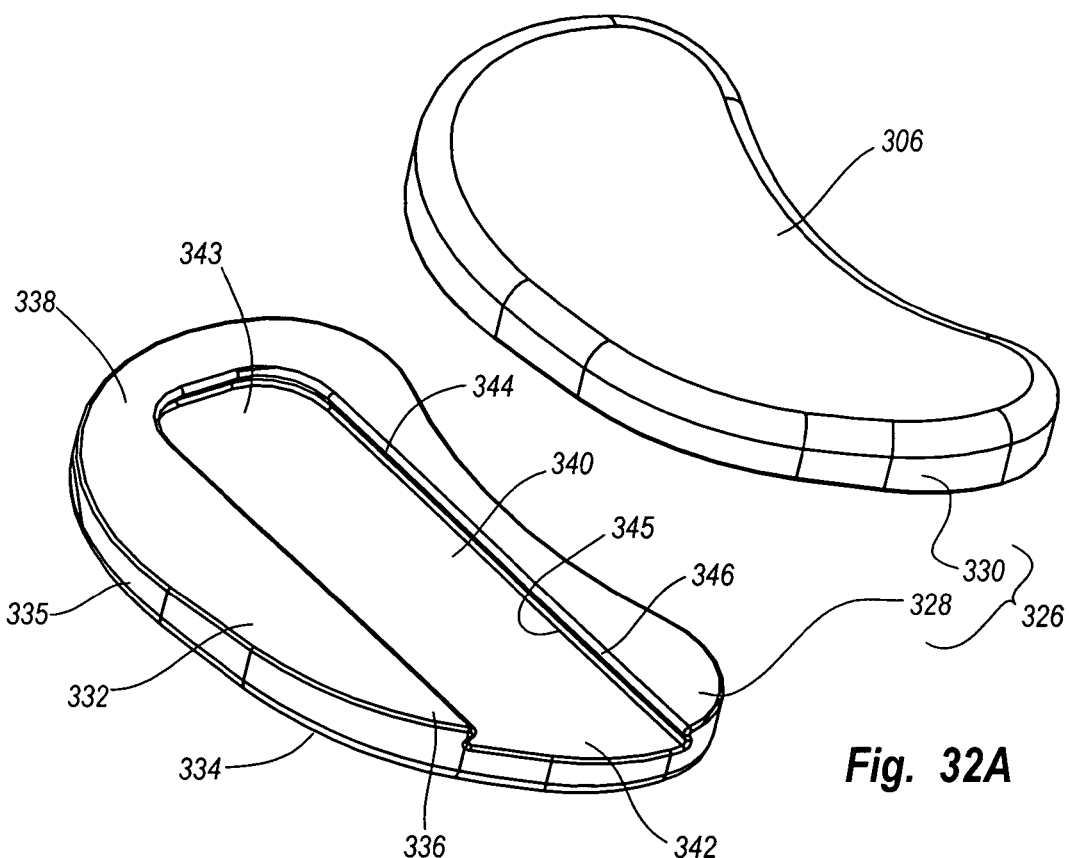
FIG. 32A is a top exploded perspective view of a two piece condylar implant having a linear track.
Figure 32B:
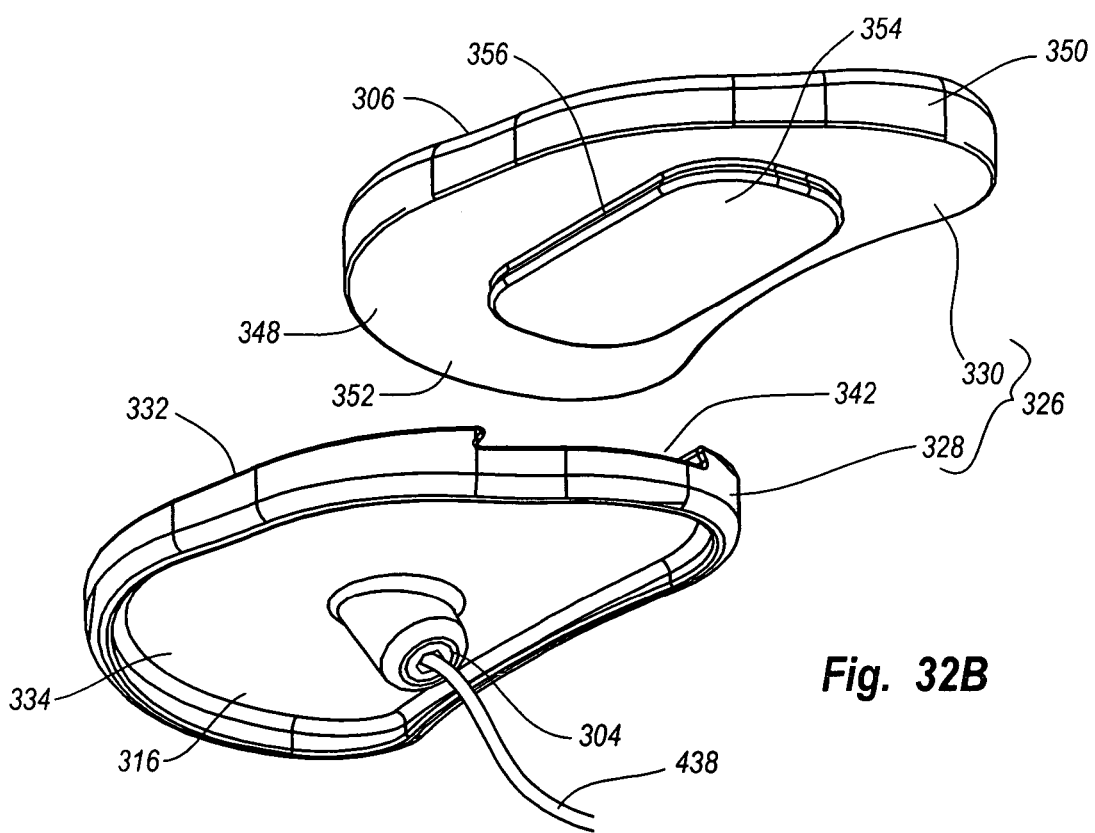
FIG. 32B is bottom exploded perspective view of the condylar implant shown in FIG. 32A.

Depicted in FIGS. 32A and B is another alternative embodiment of a condylar implant 326. Like elements between condylar implants 300 and 326 are identified by like reference characters. In contrast to condylar implant 300 which is fixed and rigid, condylar implant 326 is mobile. Specifically, in condylar implant 326 the body comprises a lower bearing plate 328 from which the flexible line projects and an upper bearing plate 330 that is slidably mounted on lower bearing plate 328.

Lower bearing plate 328 has a top surface 332 and an opposing bottom surface 334 with a perimeter edge 335 extending therebetween. Pocket 316 is formed on bottom surface 334 to receive inlay 320. In this embodiment, stem 304 is shown elongated and at an angle. If desired, stem 304 can be formed long enough so that it extends directly into the tunnel formed on the tibia. Likewise, stem 304 can be oriented at any angle to correspond with the tunnel. Top surface 332 is substantially flat or inwardly arched and extends between an anterior end 336 and a posterior end 338. A track 340 is recessed on top surface 332. Track 340 has an open mouth extending through perimeter edge 335 at anterior end 336 and longitudinally extends toward posterior end 338. Track 340 is bounded by a substantially flat floor 343 having a sidewall 344 upstanding therefrom. Sidewall 344 comprises a recess groove 345 which extends along floor 343 and an outwardly projecting lip 346 which projects along top surface 332. As such, the opposing sidewalls 344 of track 340 form a mortis.

Upper bearing plate 330 comprises top articular surface 306 and a bottom surface 348 which each extend between an anterior end 350 and an opposing posterior end 352. Bottom surface 348 has a configuration substantially congruent to top surface 332 of lower bearing plate 328. Projecting from bottom surface 348 is an elongated key 354 which extends from toward anterior end 350 to toward posterior end 352. Key 354 has a sidewall 356 that is substantially complementary to sidewall 344 of tack 340 such that key 354 forms a tenon that can slide into track 340 from mouth 342. In this position key 354 can freely slide along track 340 but is prevented from vertically separating from track 340.

During use, upper bearing plate 330 can slide posterior-anterior on lower bearing plate 328 as the femoral condyle rotates on top articular surface 306. This ability of upper bearing plate 330 to slide minimizes high stress points between the femoral condyle and upper bearing plate, thereby minimizing wear. Furthermore, because bearing plates 328 and 330 slide against each other on congruent surfaces, both of bearing plates 328 and 330 can be comprised of metal without producing undue wear. In other embodiments, bearing plates 328 and 330 can be comprised of plastics, ceramics, or composites of different materials. In addition, bearing plates 328 and 330 can be made of the same or different materials.

Figure 33A:
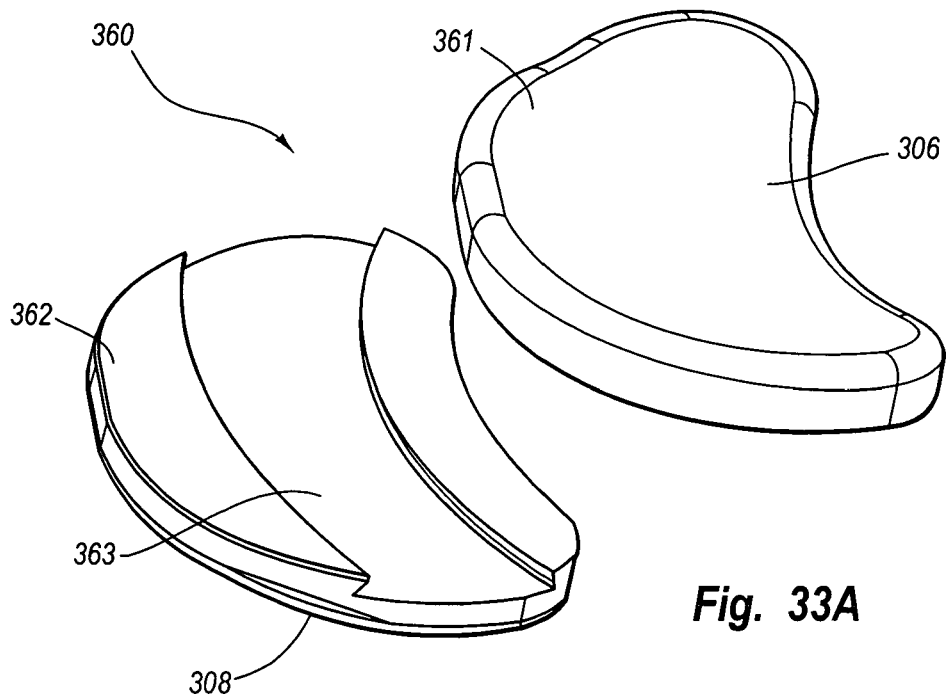
FIG. 33A is a top exploded perspective view of a two piece condylar implant having a curved track.
Figure 33B:
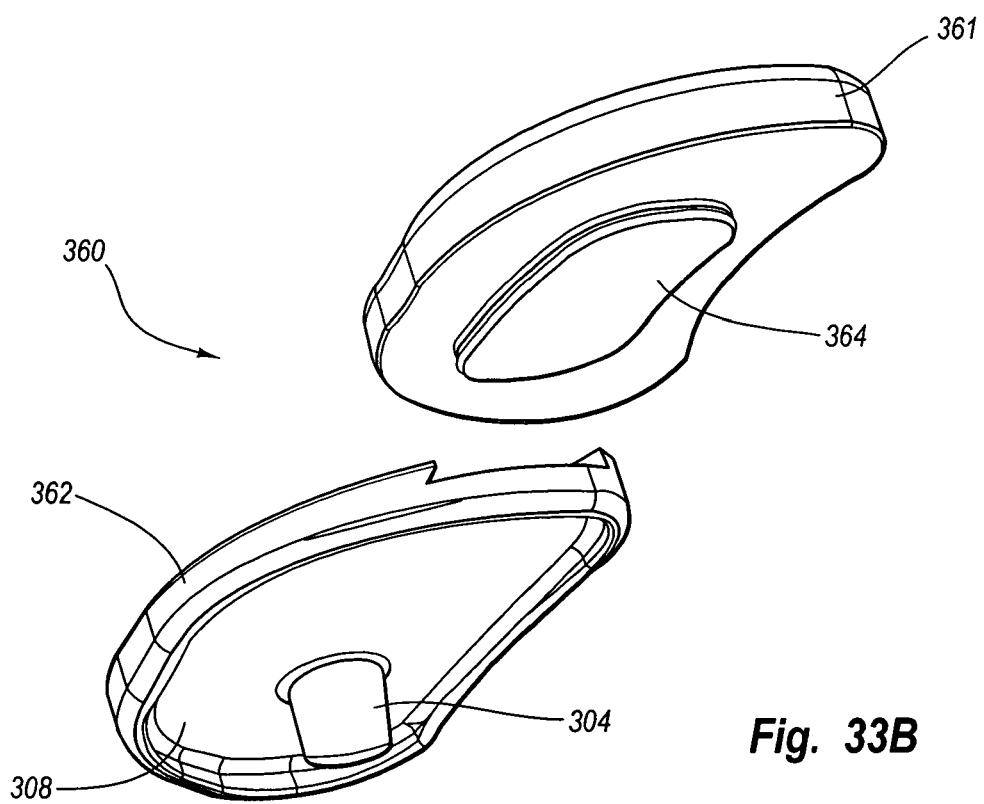
FIG. 33B is bottom exploded perspective view of the condylar implant shown in FIG. 33A.

Although key 354 and track 340 are shown as being linear, in alternative embodiments they can be congruently curved to more naturally correspond to the bending movement of the knee. For example, depicted in FIGS. 33A and B is another alternative embodiment of a condylar implant 360 which includes an upper bearing plate 361 and a lower bearing plate 362. In this embodiment, lower bearing plate 362 includes a track 363 that is curved along the length thereof. Upper bearing plate 361 includes an elongated key 364 having a curve complementary to track 363 such that key 364 can freely slide within track 363. As previously discussed, key 364 and track 363 can also be arched or curved in a vertical plane.

Figure 34:
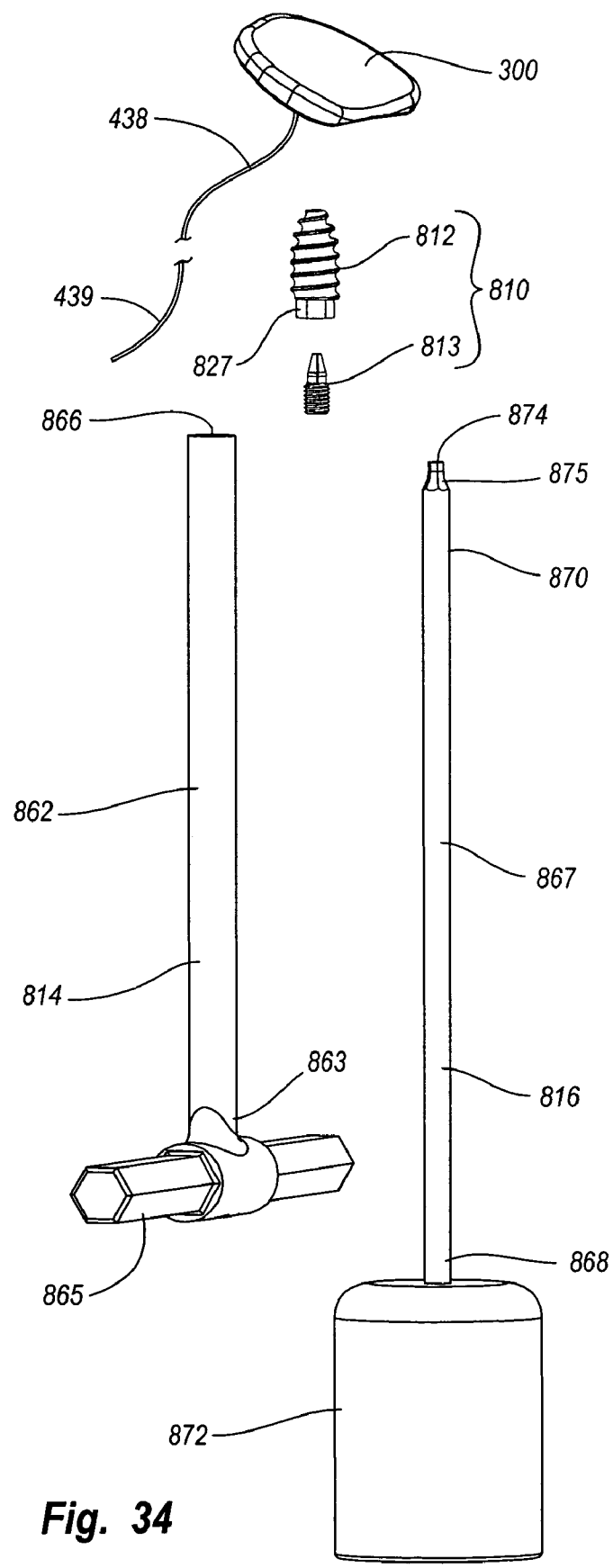
FIG. 34 is an exploded view of an anchor assembly for securing a condylar implant to a tibia.

Depicted in FIG. 34 is one embodiment of an anchor assembly 810 used to secure condylar implant 300 to tibia 12. Anchor assembly 810 comprises a bone anchor 812 that operably connects with a lock 813. As discussed below in greater detail, bone anchor 812 is selectively placed by a first drive driver 814 while lock 813 is selectively placed by a second driver 816.

Figure 35:
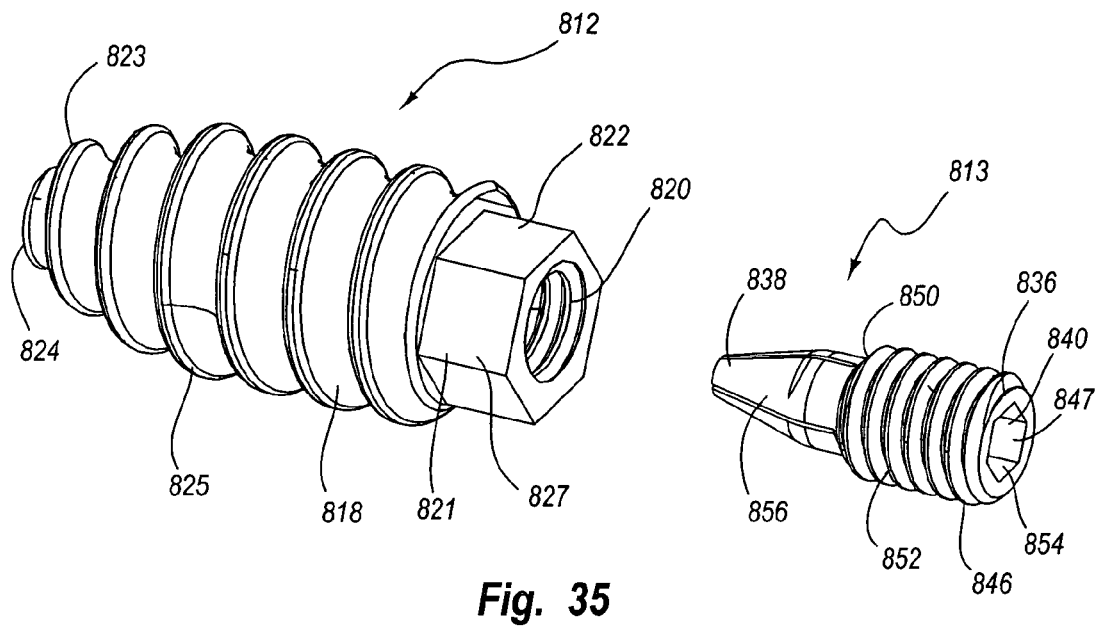
FIG. 35 is an enlarged perspective view of the anchor assembly shown in FIG. 34 including a bone anchor and a lock.

Turning to FIG. 35, bone anchor 812 comprises a tubular body 818 having a substantially cylindrical configuration. Body 818 includes an interior surface 820 and an exterior surface 821 that each extend between a proximal end 822 and an opposing distal end 823. Distal end 823 tapers to a reduced nose 824. Formed at proximal end 822 is an engaging head 827 having an exterior surface with a transverse cross section that is polygonal or any other non-round configuration. As a result, first driver 814 can connect with engaging head 827 to selectively rotate bone anchor 812. Encircling and radially outwardly projecting from exterior surface 821 are one or more helical threads 825. Threads 825 can be conventional or self-tapping and extend radially outward beyond the outer perimeter of engaging head 827. In alternative embodiments, threads 825 can be replaced by ridges, barbs, or other bone engaging structures used in conventional bone anchors. Bone anchor 825 can be formed of a biocompatible metal, a bioabsorbable polymer, a bioactive ceramic, or any other desired material.

Figure 36:
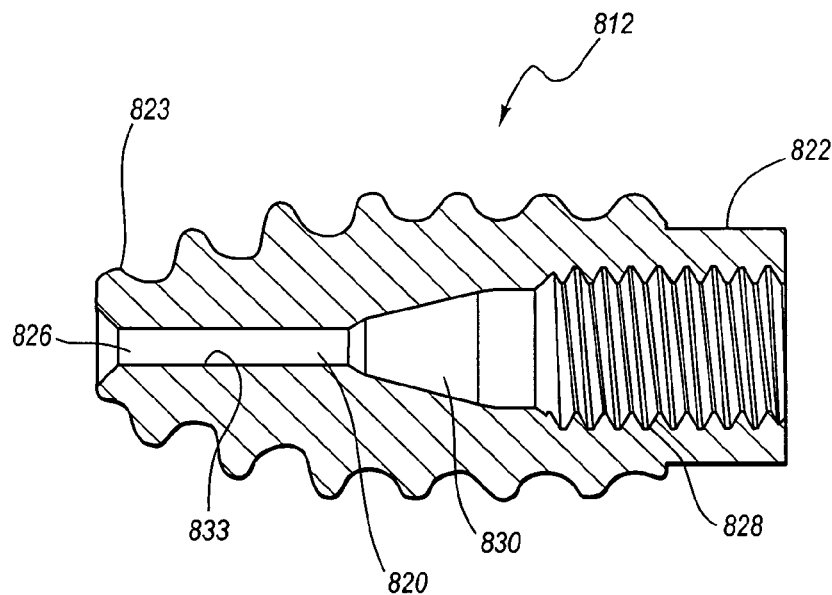
FIG. 36 is a cross sectional side view of the bone anchor shown in FIG. 35.

As depicted in FIG. 36, interior surface 820 bounds a channel 826 longitudinally extending through bone anchor 812. Extending proximal to distal, interior surface 820 comprises a threaded portion 828, a frustoconical tapered portion 830, and a constricted cylindrical portion 833.

Returning to FIG. 35, in the embodiment depicted, lock 813 comprises a collet. In general, lock 813 has a proximal end 836, an opposing distal end 838, and a channel 840 extending therebetween. More specifically, lock 813 comprises a tubular body 846 extending from proximal end 836 to a second end 850. Encircling and radially, outwardly projecting from body 846 are one or more helical threads 854. Threads 854 are configured to engage with threaded portion 828 of bone anchor 812. At least a portion of channel 840 extending through body 846 is bounded by an interior surface 847 having a polygonal or other non-circular transverse cross section so that second driver 816 (FIG. 34) can be secured therein for selective rotation of lock 813.

Figure 37:
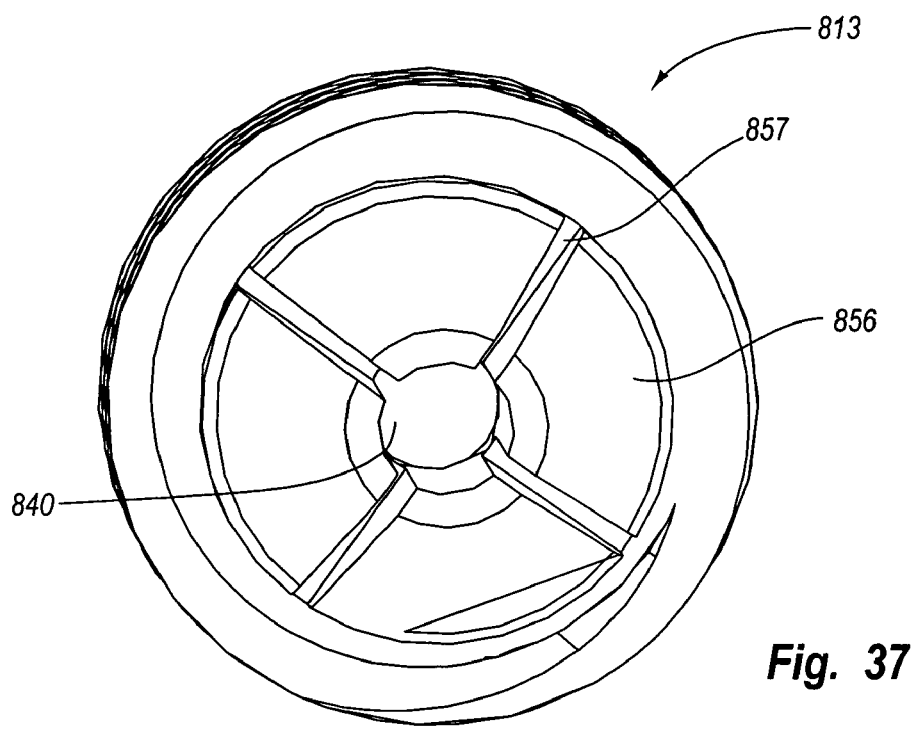
FIG. 37 is an elevated front view of the lock shown in FIG. 35.

Projecting from second end 850 of body 846 are a plurality of flexible fingers 856. As depicted in FIG. 37, four fingers 856 are provided with each finger 856 being separated by a slot 857 extending along the length of fingers 856. In alternative embodiments, two or more fingers 856 can be used. The distal end of each finger 856 is radially, inwardly tapered.

Figure 38:
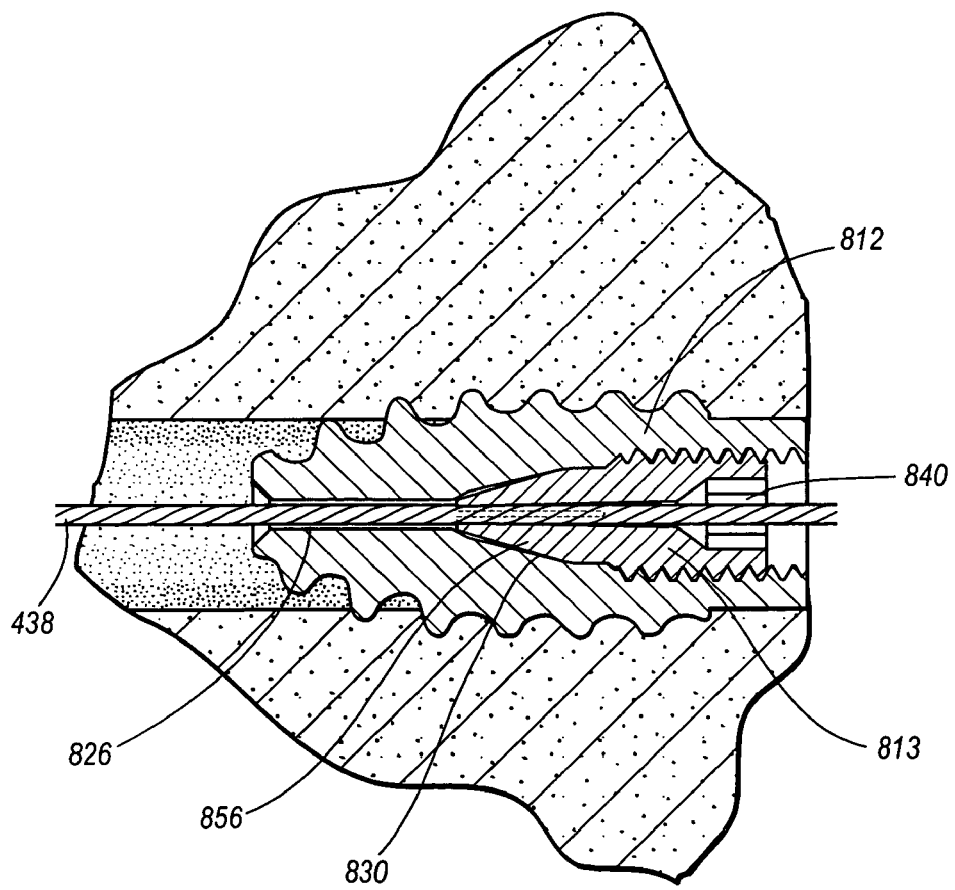
FIG. 38 is a cross sectional side view of the assembled anchor assembly shown in FIG. 35 having a line extending therethrough.

As depicted in FIG. 38, during operation lock 813 is partially screwed into proximal end 822 of bone anchor 812. In this position, with fingers 856 unflexed, line 438 is passed through channels 826 and 840. As discussed below in greater detail, when it is desired to secure line 438 relative to bone anchor, lock 813 is advanced further into bone anchor 812 until tightly secured therein. In so doing, fingers 856 of lock 813 bias against tapered portion 830 of bone anchor 812 which causes fingers 856 to radially, inwardly constrict and securely engage line 438. In this position, line 438 is prevented from being pulled in either direction. However, line 438 can again be freely moved by simply unscrewing lock 813 from within bone anchor 812 so that fingers 856 are able to freely, outwardly flex.

Returning to FIG. 34, first driver 814 comprises a tubular shaft 862 having a proximal end 863 and an opposing distal end 864. A handle 865 is formed at proximal end 863. A passage 866 extends through shaft 862 and handle 865 so that line 438 can pass completely through first driver 814. Passage 866 at distal end 864 has an interior surface that is complementary to the exterior surface of engaging head 827 of bone anchor 812. As such, first driver 814 can be selectively coupled with bone anchor 812 for selective rotation of bone anchor 812.

Second driver 816 also comprises a tubular shaft 867 having a proximal end, 868 and an opposing distal end 870. A tubular handle 872 is mounted proximal end 868. As such, a passage 874 extends the length of second driver 816 so that line 438 can extend completely therethrough. Distal end 870 of shaft 867 terminates at a tip 875. Tip 875 has a configuration complementary to channel 840 at proximal end 836 of lock 813. As such, second driver 816 can be selectively coupled with lock 813 for selective rotation of lock 813.

Figure 39:
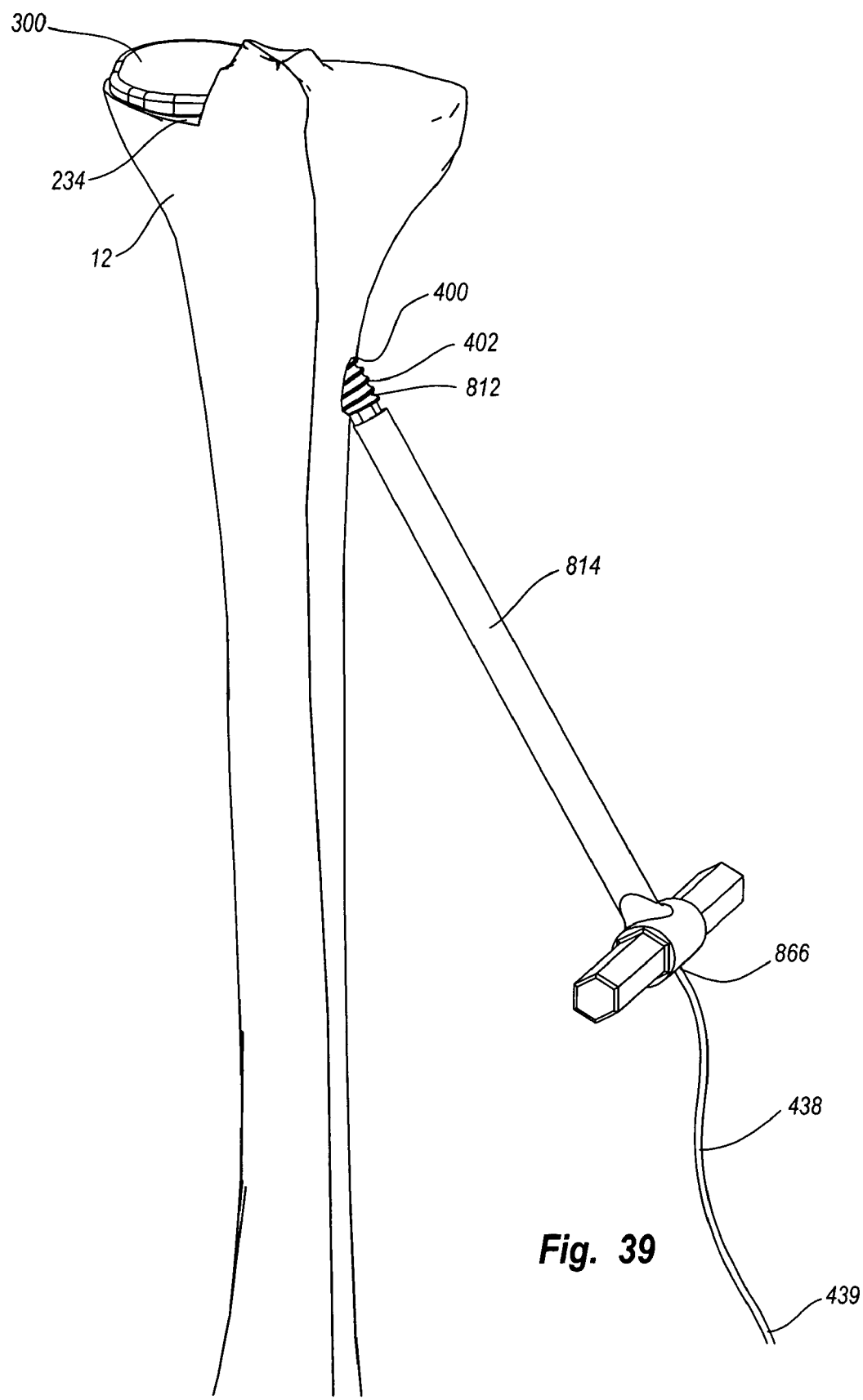
FIG. 39 is a perspective view of an implant mounted on a tibia with the anchor assembly of FIG. 38 being mounted to the tibia.

Turning to FIG. 39, to facilitate mounting of condylar implant 300, with the second end of line 438 connected to implant 300, first end 439 of line 438 is passed through tunnel 400 from second end 404 (FIG. 17) to first end 402. In one embodiment this is accomplished by passing an instrument up through tunnel 400 from first end 402 to second end 404. The instrument is then used to grab first end 439 of line 438 and pull it down through tunnel 400. Other techniques can also be used.

Line 438 is continually pulled through tunnel 400 to remove all slack. With the slack removed, condylar implant 300 is slid onto resected surface 234 so as to fit within pocket 278. Here it is noted that because condylar implant 300 has a relatively low profile, condylar implant 300 can be easily passed through the relatively small incision that was originally formed over the medial meniscus. This is in contrast to other conventional procedures where larger incisions must be made to either allow placement of an implant having a large stem that is embedded within the bone for securing or to provide access room to enable securing the implant by passing screws down through the top of at least a portion of the implant.

Once implant 300 is positioned, bone anchor 812 is fed onto line 438. Specifically, with lock 813 partially inserted into bone anchor 812, as discussed above with reference to FIG. 38, first end 439 of line 438 is passed distal to proximal through channels 826 and 840 of bone anchor 812 and lock 813. First end 439 of line 438 then is passed distal to proximal through passage 866 of first driver 814 so that first driver 814 can removably couple with bone anchor 812. It is appreciated that the above steps can be performed in a variety of different sequences. For example, line 428 can be passed through bone anchor 812 and lock 813 separately before they are connected together.

First driver 814 is then used to screw bone anchor 812, having lock 813 therein, into first end 402 of tunnel 400. Bone anchor 812 is advanced until proximal end 822 passes into tibia 12. In one embodiment, a tap, not shown, is used to initially thread the interior surface of tunnel 400 at first end 402. Alternatively, bone anchor 812 can be self-tapping.

Figure 40:
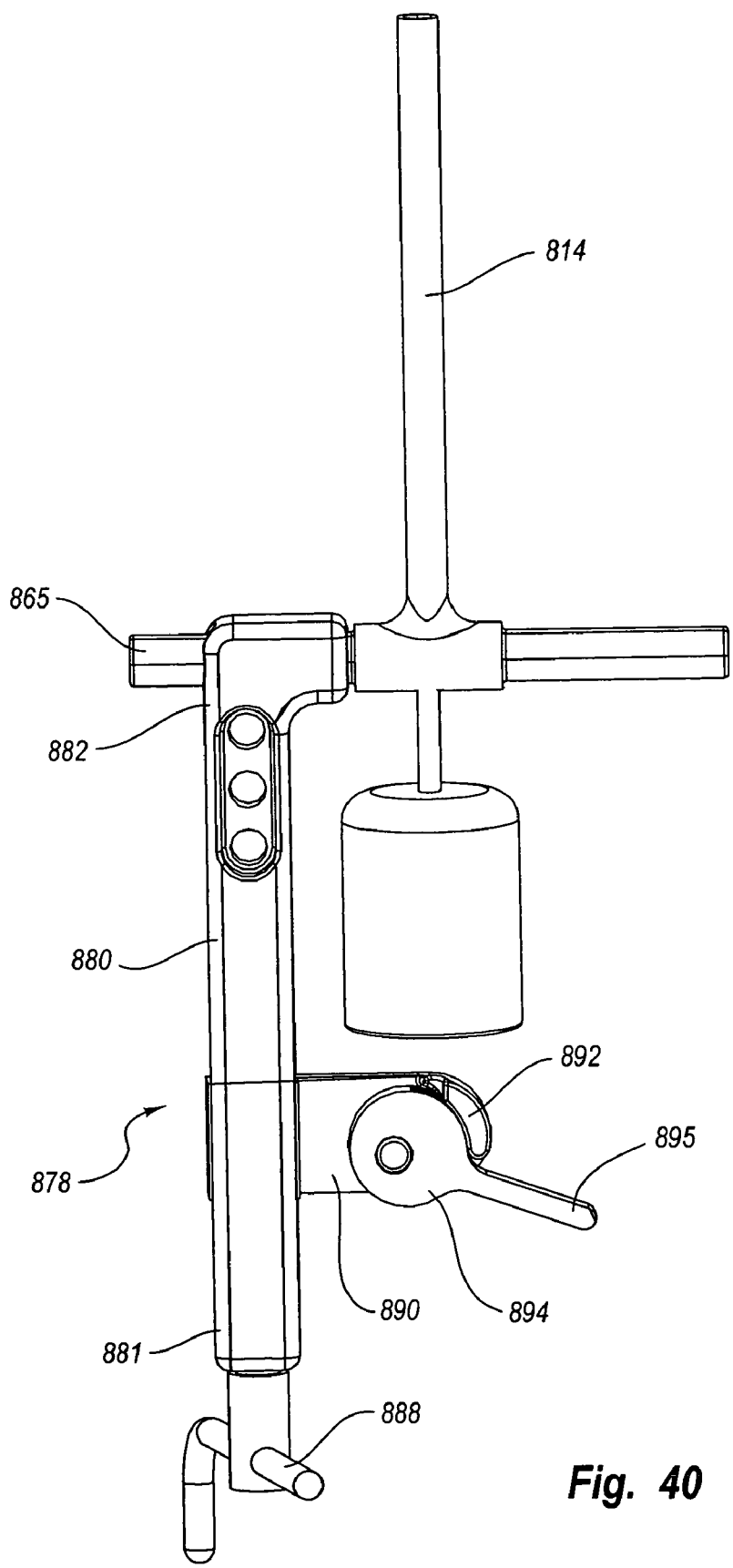
FIG. 40 is an elevated front view of a tensioner.
Figure 41:
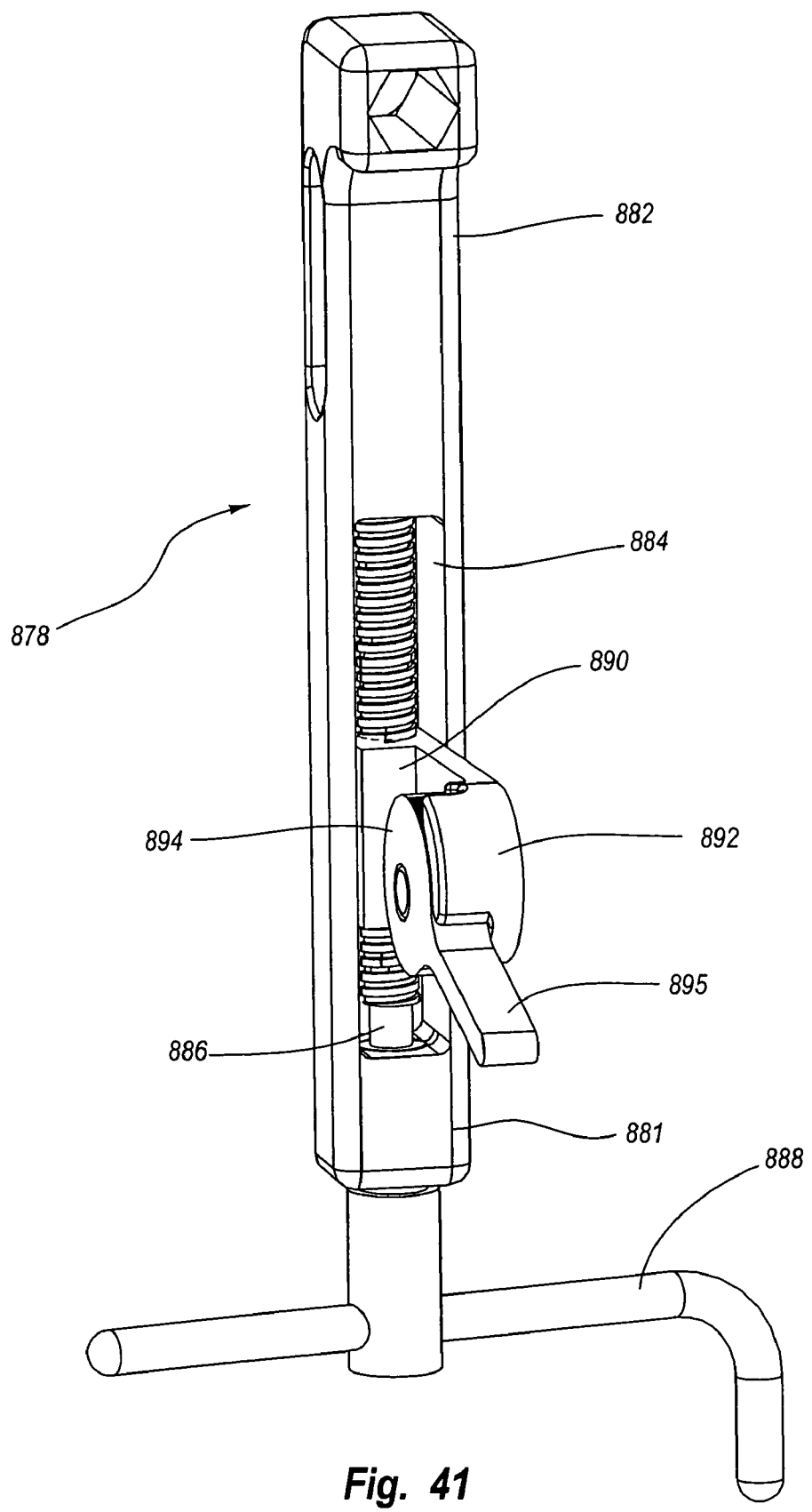
FIG. 41 is an elevated side view of the tensioner shown in FIG. 40.

Next, a tensioner 878 is used to tension line 438. As depicted in FIGS. 40 and 41, tensioner 878 comprises a frame 880 having a proximal end 881 and an opposing distal end 882. Distal end 882 removably connects to handle 865 of fist driver 814. A channel 884 is formed within a portion of frame 880. Rotatably disposed within channel 884 is a threaded shaft 886. A portion of shaft 886 extends beyond proximal end 881 and has a handle 888 connected thereto. Mounted on threaded shaft 886 within channel 884 is a clamp arm 890. Clamp arm 890 is mounted such that rotation of shaft 886 by rotation of handle 888 causes clamp arm 890 to selectively advance along shaft 886 depending on the direction of rotation.

Positioned on clamp arm 890 is a stop plate 892. An eccentrically mounted cam 894 is rotatably mounted to clamp arm 890 and is spring biased against stop plate 892. A handle 895 projects from cam 894. Depressing handle 895 causes cam 894 to rotate away from stop plate 892. Line 438 can then be placed between cam 894 and stop plate 892. When handle 895 is released, cam 894 spring biases against stop plate 892 causing line 438 to be secured therebetween. Because cam 894 is eccentrically mounted, the more tension on line 438 toward first driver 814, the greater the force applied by cam 894 to secure line 438 in place.

Figure 42:
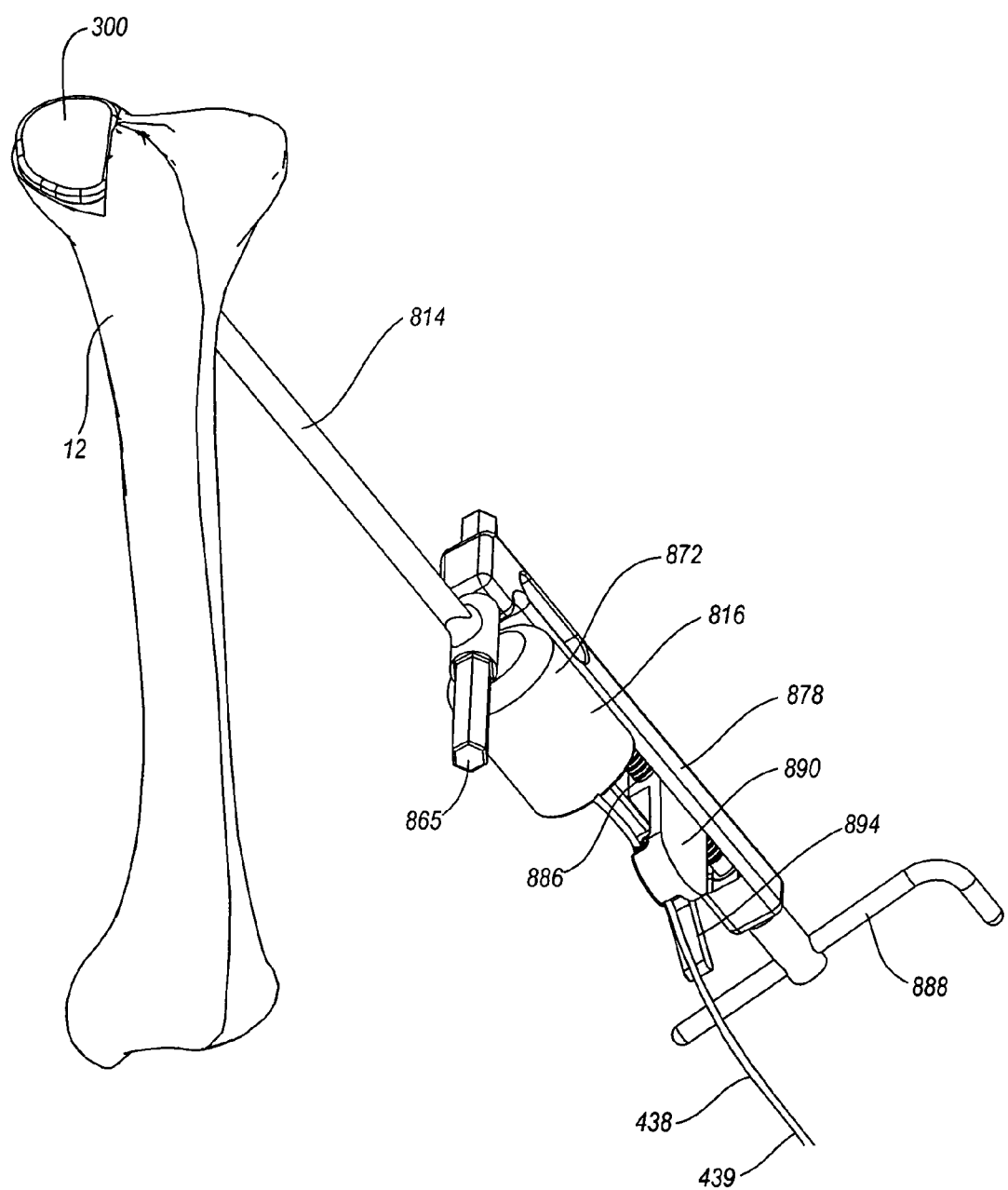
FIG. 42 is a perspective view of the tensioner shown in FIGS. 40 and 41 coupled with the mounted anchor assembly shown in FIG. 39.

Turning to FIG. 42, once bone anchor 812 has been mounted to tibia 12, first end 439 of line 438 is passed distal to proximal through passage 874 in second driver 816. Proximal end 870 of second driver 816 is then advanced proximal to distal through passage 866 of first driver 814. Second driver 816 is advanced until distal tip 875 couples with lock 813. Next, tensioner 878 is connected with handle 865 of first driver 814. Line 438 extending from second driver 816 is then connected to clamp arm 890 by cam 894 as discussed above. Handle 888 of tensioner 878 is then rotated so that clamp arm 890 is moved along threaded shaft 886 away from second driver 816. In so doing, a tension force is applied to line 438. A force measuring device, such as a transducer, can be coupled with tensioner 878 for measuring the tension force applied to line 438. In turn, the tension force on line 438 is the same force used to bias implant 300 against tibia 12. When a sufficient tension force is applied to line 438, handle 872 of second driver 872 is rotated, thereby causing lock 813 to secure line 438 within bone anchor 812. In one embodiment, the tension force applied to line 438 is in a range between about 25 pounds (110 N) to about 300 pounds (1,335 N) with about 150 pounds (670 N) to about 250 pounds (1,110 N) being more common. Other forces can also be applied.

Once lock 813 is secured in place, tensioner 878, second driver 816 and first driver 814 are removed. One of the unique features of this embodiment of the present invention is that should the surgeon wish to make some modification to the implant or related anchor system, lock 813 can simply be loosened using second driver 816 to allow the desired movement or adjustment. The above process can then be repeated to resecure implant 300 in place. Once properly position and secured, line 438 is severed just proximal of lock 813. Even after line 438 is severed, however, further tension can be applied to line 438 by backing bone anchor 812 back toward first end 402 of tunnel 400 using first driver 814. Closing procedures for the tissue are then performed.

It is appreciated that the same above process can be used for securing implant 300 to tibia 12 using tunnel 90 as shown in FIG. 10. Furthermore, a first tunnel 90 can be formed for use in resecting tibia 12 following which a second tunnel 400 can be formed for placement of line 438 and anchor assembly 810. It is likewise appreciated that many of the mounting steps can be modified or performed in an alternative order. For example, in one method condylar implant can be positioned on resected surface 234 prior to having line 438 connected thereto. As previously discussed with regard to FIG. 22, a driver can then be used to secure line 438 to implant 300 by passing retainer 444 through tunnel 400 from first end 402 to second end 404 where retainer is then screwed into implant 300, thereby securing line 438 to implant 300.

In one embodiment of the present invention means are also provided for securing line 438 to bone anchor 812. One example of such means comprises lock 813. In alternative embodiments lock 813 can have a variety of different configurations or be replaced with a variety of different structures. For example, any number of different wedges, cleats, or cams can be placed in bone anchor 812 so that line 438 can be pulled one way through bone anchor 812 but is prevented from being pulled back. In yet other embodiments, once line 438 is tensioned, a lock can be crimped or otherwise secured to line 438. The lock would then bias against bone anchor 812 to prevent line 438 from being pulling back through bone anchor 812. Examples of various locks which can be used are disclosed in U.S. Pat. No. 5,702,397, issued Dec. 30, 1997 and U.S. patent application Ser. No. 09/970,559, filed Oct. 3, 2001. The bone anchors with related line locking structures disclosed in U.S. Pat. No. 5,702,397 and application Ser. No. 09/970,559 are incorporated herein by specific reference.

Figure 43:
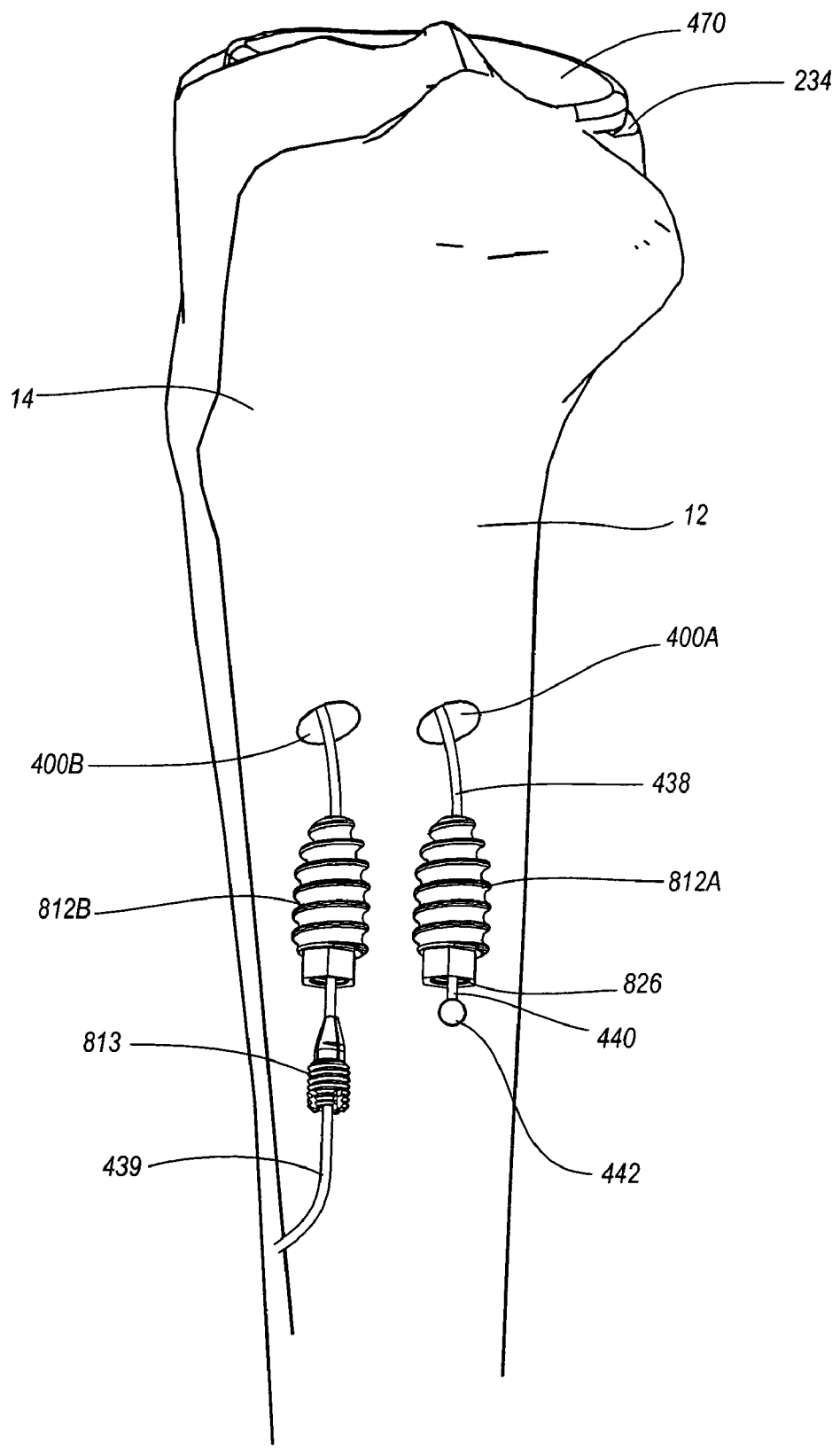
FIG. 43 is a perspective view of a system used to secure the implant shown in FIG. 31 to the tibia.

Depicted in FIG. 43 is one embodiment of a system used for mounting implant 470 as previously discussed with regard to FIG. 31. In this embodiment, two tunnels 400A and 400B extend from lateral side 14 of tibia 12 to resected surface 234. Tunnels 400A and B can be formed having parallel alignment or any desired angle. Furthermore, tunnels 400A and B can be formed by moving tunnel guide 370 (FIGS. 20 and 21) to two locations at which the tunnels are drilled or tunnel guide 370 can be formed having two adjacent guide sleeves 378 mounted on the brace 372. Each tunnel guide 370 can then be used for forming corresponding tunnels 400A and B.

To secure implant 470 to tibia 12, first end 439 of line 438 is passed proximal to distal through channel 826 in first bone anchor 812A. First end 439 is then passed up through first tunnel 400A, though passages 475 on implant 470 (FIG. 31), down through second tunnel 400B, and finally through second bone anchor 812B and lock 813. First driver 814 is used to drive bone anchors 812A and B into corresponding tunnels 400A and B. Line 438 is pulled down through second tunnel 400B so as to remove the slack therefrom. In so doing, enlarged head 442 on second end 440 of line 438 is advanced into first bone anchor 812A where head 442 is securely wedged within tapered portion 830 of channel 826 (FIG. 36). With second end 440 of line 438 secured to bone anchor 812A, the same process previously discussed with regard to FIG. 42 is used tension line 438 and secure line 438 to second bone anchor 812 using lock 813.

It is appreciated that first bone anchor 812A can be replaced with a variety of alternative structures that prevent second end 440 of line 438 from being pulled through first tunnel 400A. For example, the first bone anchor can simply comprise an enlarged washer that captures enlarged head 442 but is too big to pass through tunnel 400A. In yet other embodiments, the first bone anchor can simply comprise an enlarged tubular wedge that wedges into tunnel 400A but cannot pass therethrough. In still other embodiments, line 438 can be formed without enlarged head 442. In this embodiment, lock 813 or other wedging or locking type structure can be used to secure second end 440 of line 438 to the first bone anchor. Where two separate lines 438 are connected to an implant, each line is extended through a corresponding tunnel. The process discussed with regard to FIG. 42 is then separately performed for each separate line.

By using the above discussed implants and anchor assemblies with the corresponding methods and instruments, it is appreciated that the implants can be securely mounted to tibia 12 using procedures that are minimally invasive. Furthermore, because the implants are only secured in place after they are positioned on the proximal end of the tibia, the surgeon can easily switch out different sizes of implants when trying to determine an appropriate fit. Likewise, because the anchoring assemblies are operated through the first end of the tunnel which is remote from the implant, the inventive anchoring assemblies enable the surgeon to easily adjust the placement of the implant during initial positioning and to subsequently remove the implant should a replacement be required at a later date.

Furthermore, as a result of using a flexible line to secure the implants, the surgeon can select the best location for forming the tunnel and mounting the bone anchor at the time of the operation. That is, the surgeon is not limited to forming the tunnel at a predefined location based on structural limitations imposed by the implant. In addition, because the line can be relatively small, the size of the required tunnel can be minimized, thereby minimizing the amount of bone that needs to be removed when forming the tunnel. Replacement of a worn or damaged implant is also relatively easily achieved by cutting the line.

Because the inventive implants, anchor assemblies, tissue preparation instruments, and corresponding methods each produce independently unique benefits, it is appreciated that theses various features can be used independently with other conventional apparatus and techniques. For example, in one embodiment a larger incisions can be made at the knee of a patient and the proximal end of tibia 12 resected using conventional resection techniques. In this embodiment, tunnel 90 and/or 400 can be formed either before or after the resection of tibia 12. Once the tibia is resected and the tunnel formed, the above procedure can then be used to secure condylar implant 300. In another alternative, tunnel 90 can be formed and tibia 12 resected as discussed above. However, once tibia 12 is resected, a conventional implant can be mounted on tibia 12 using conventional techniques.

Figure 44:
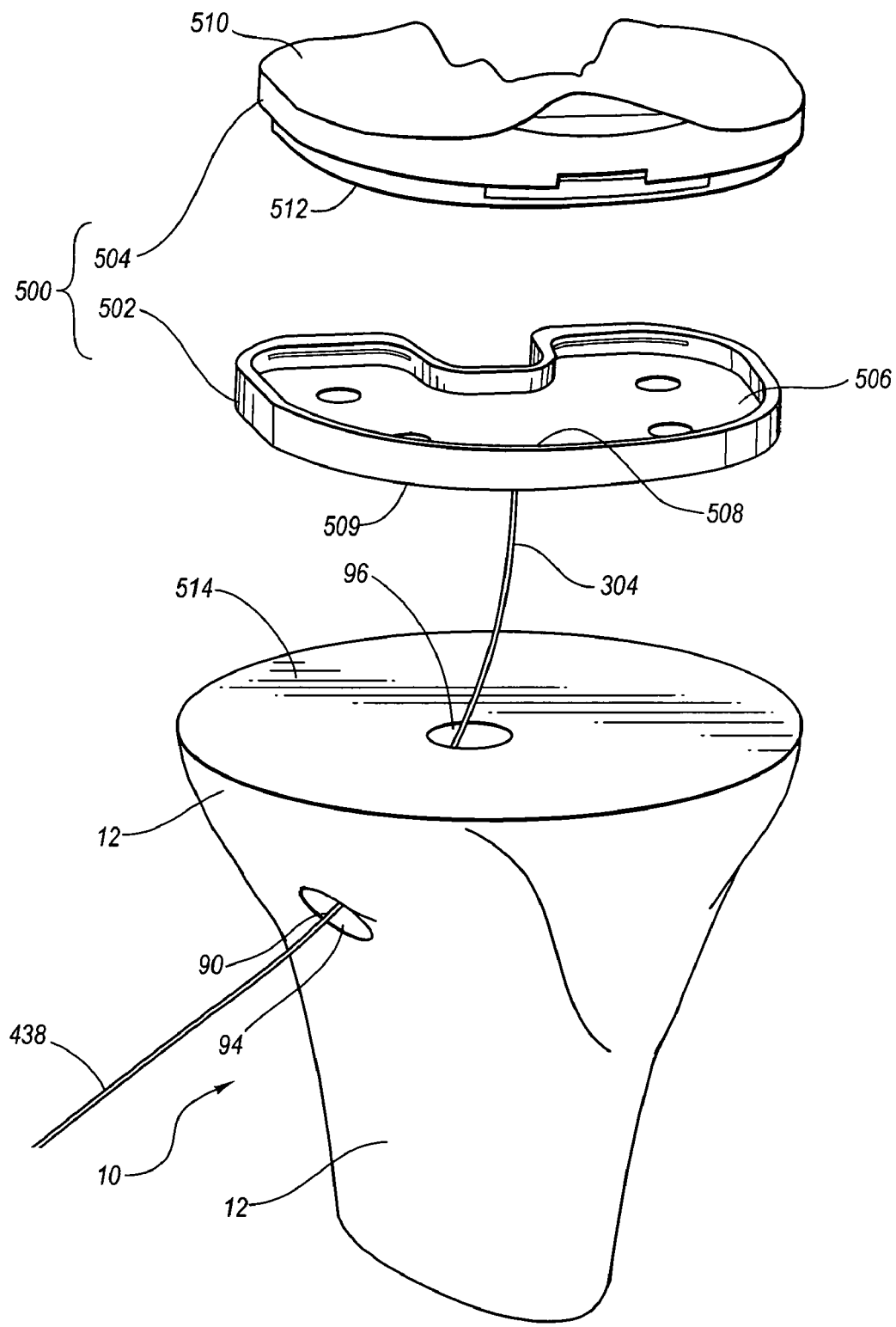
FIG. 44 is an exploded perspective view of an inventive full tibia implant for mounting on the proximal end of a tibia.
Figure 45:
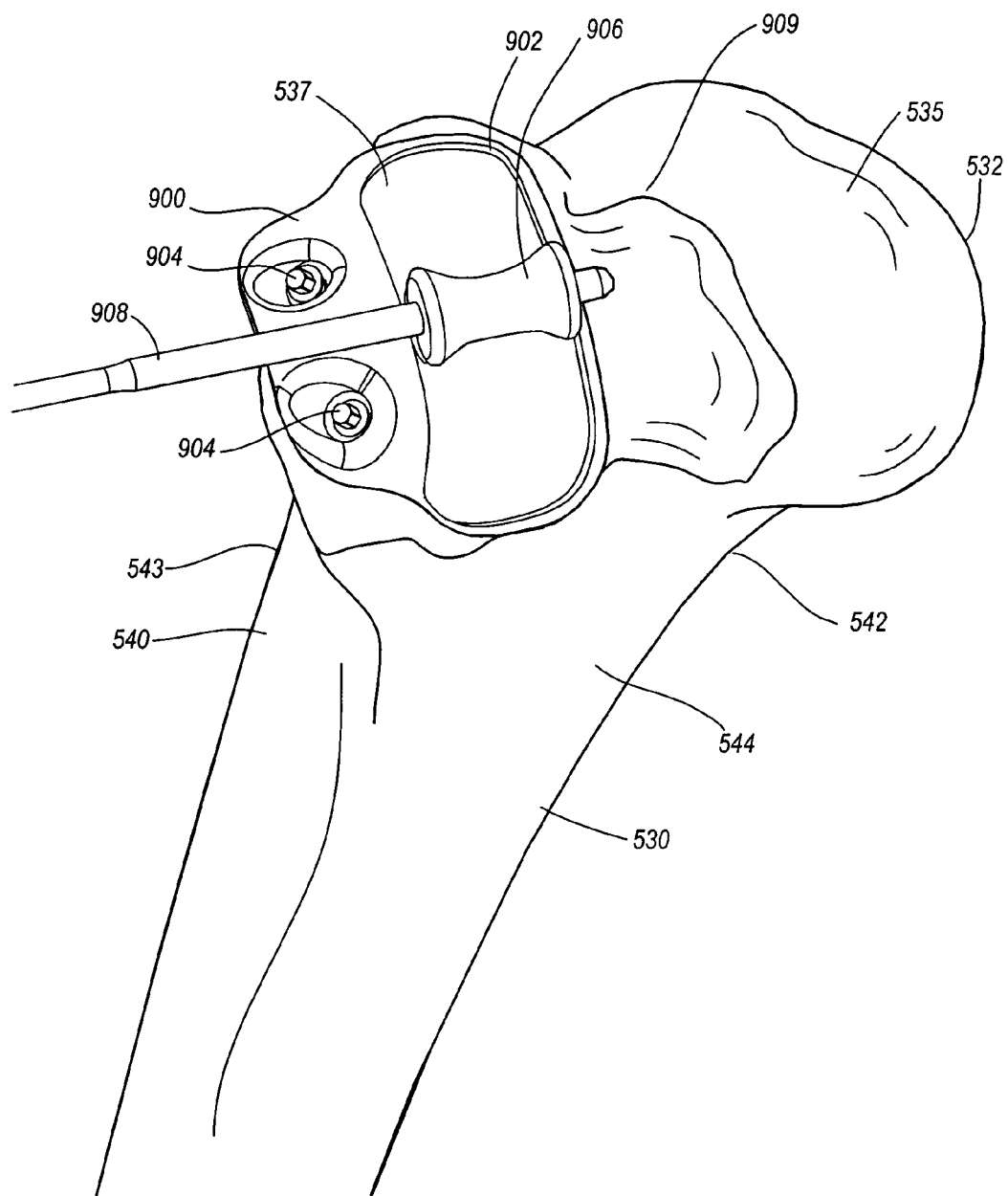
FIG. 45 is a perspective view of a guide template mounted on a medial condyle of a femur and a milling head disposed within an opening of the guide template.

The above discussed embodiments relate to mounting a condylar implant on tibia 12. As previously mentioned, however, the present invention can also be used to mount other types of implants on other articulation surface so as to achieve one or more of the same benefits. For example, depicted in FIG. 44 is a full tibial implant 500. Tibial implant 500 comprises a tray 502 and a bearing plate 504. Tray 502 has a top surface 506 and an opposing bone apposition surface 509. Top surface 506 bounds a pocket 508 which is configured to receive and lock bearing plate 504. Bearing plate 504 has a top articular surface 510 and a bottom surface 512 which is selectively snap fit within pocket 508 of tray 502.

In one embodiment, tray 502 is comprised of metal while bearing plate 504 is comprised of a polymeric material. It is noted that bearing plate 504 and tray 502, as discussed above, are well known in the art and can be replaced with a variety of other conventional bearing plates 504 and trays 502 used in full tibial implants. The distinction over the prior art, however, is that tray 502 has been modified so that line 438, as previously discussed, is connected to tray 502 so as to project from bone apposition surface 509.

As also depicted in FIG. 44, proximal end 10 of tibia 12 has been uniformly resected so as to form a resected articulation surface in the form of a tibial plateau 514. Tunnel 90 includes second end 96 formed on tibial plateau 514 and first end 94 spaced apart from tibial plateau 514. Tibia 12 can be resected to form tibial plateau 514 by using any of the methods or combination of methods disclosed herein or by using other conventional techniques. For example, tunnel 90 can be formed using the method disclosed for forming tunnel 400. Depending on the method used, tunnel 90 can be formed before or after resection of tibia 12.

Once tibia 12 is resected, line 438 is passed through tunnel 90 and tray 502 is positioned on tibial plateau 514 so that the location where line 438 connects with tray 502 aligns with second end 96 of tunnel 90. One of the above discussed anchor assemblies is then used to secure tray 502 to tibia 12. Bearing plate 504 can be secured to tray 502 either before or after securing tray 502 to tibia 12.

It is appreciated that the various alternatives discussed above with regard to how line 438 can be mounted to tray 502 and the number and position of inlays are also applicable to tray 502. Furthermore, to help prevent unwanted movement of tray 502, resected surface 514 can be contoured with a pocket of which bone apposition surface 509 has a complementary configuration. Likewise, any number of spikes, fins, or projections can be formed so as to project from bone apposition surface 509.

Features of the present invention can also be used for mounting a femoral implant on the distal end of a femur. Like elements between different embodiments are identified by like reference characters. For example, depicted in FIG. 43 is a distal end 532 of a femur 530 having a medial side 540 and a lateral side 542 that extend between an anterior side 538 and a posterior side 536. Distal end 532 of femur 530 terminates at a lateral condyle 535 and a medial condyle 537.

Mounted on medial condyle 537 is a guide template 900. Guide template bounds an elongated opening 902 that extends therethrough and which is configured to closely fit over a predefined portion of an articulation surface of medial condyle 537. Opening 902 bounds the area where the bone is to be resected and a condylar implant mounted. Guide template is curved and comes in a variety of different sizes and shapes so that a proper fit can be made on medial condyle 537. Once a proper sized and fitting guide template 900 is positioned, guide template 900 is secured in place by spaced apart screws 904 that are screwed through screw holes in guide template 900 and into the medial side of femur 530. It is appreciated that the various alternatives as discussed above with regard to guide template 236 are also applicable to guide template 900.

In one embodiment, a milling head 906 is used to facilitate resection of medial condyle 537 bounded by guide template. Milling head 906 has a substantially hour-glass configuration and has an elongated handle 908 projecting from one side and a stem 909 projecting from the other. Milling head 906 is positioned within opening 902 in a medial-lateral orientation with handle 908 projecting from medial side 540 of femur 530. In this orientation, milling head 906 is rapidly rotated and then selectively moved within opening 902 anterior-posterior. This movement is guided by the sides of guide template 900 bounding opening 902. Milling head 906 grinds away the bone bounded within opening 902 until handle 908 and stem 909 rest against guide template 900, thereby preventing milling head 906 from descending further into the bone.

Because guide template 900 is curved anterior-posterior, the milled pocket formed by milling head 906 is outwardly arched anterior-posterior. Likewise, because milling head 906 is curved lateral-medial, the milled pocket is also outwardly arched lateral-medial. As such, the recessed pocket produced by milling head 906 is arched anterior-posterior and lateral-medial. Again, this pocket configuration enables the formation of a low profile implant having substantially uniform thickness and strength. Furthermore, the pocket formation produces a stable platform for the implant having a complementary configuration. In alternative embodiments, it is again appreciated that milling head 906 can have a variety of different configurations.

Figure 46:
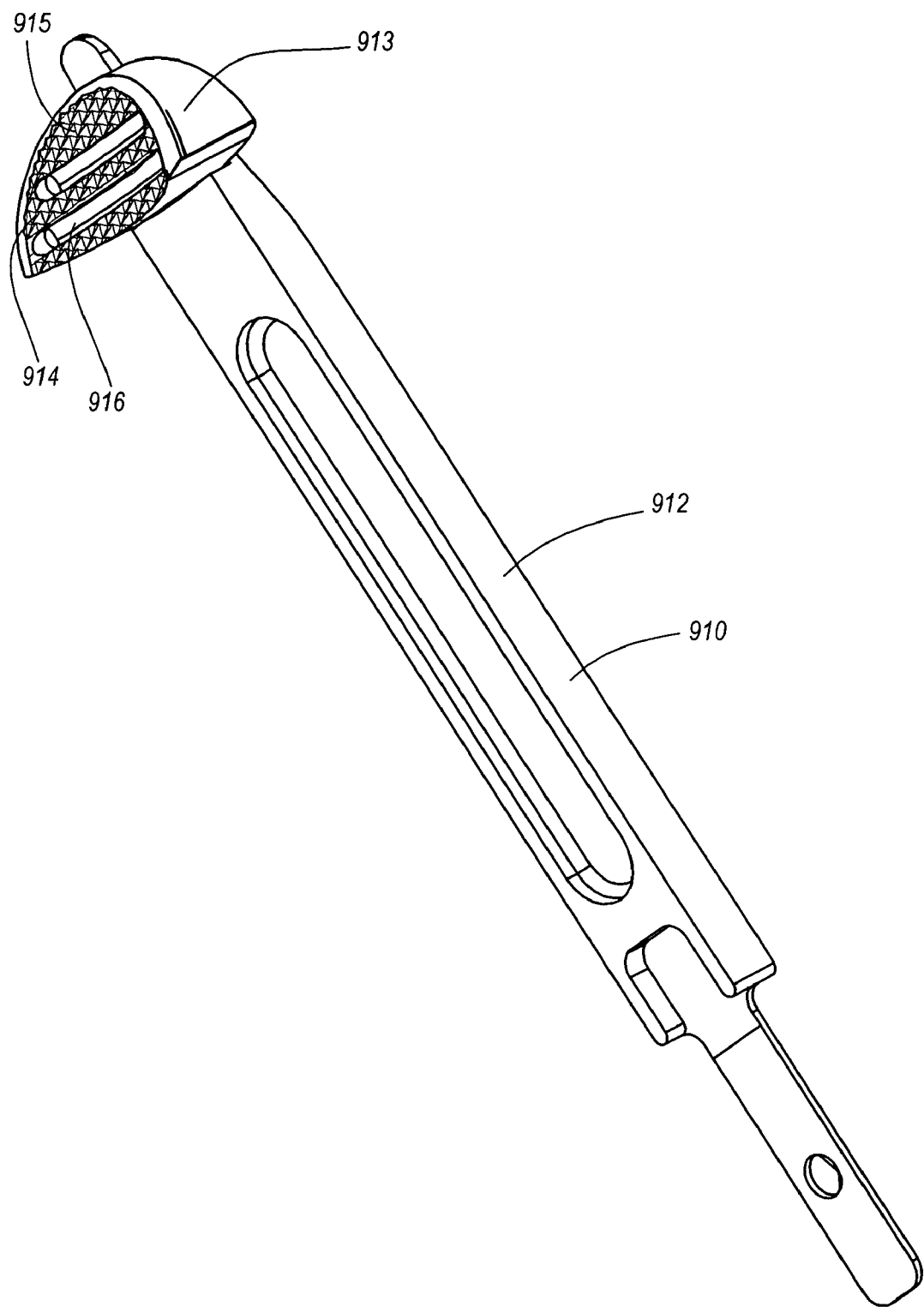
FIG. 46 is a perspective view of a rasp that is selectively used with the guide template shown in FIG. 45.
Figure 47:
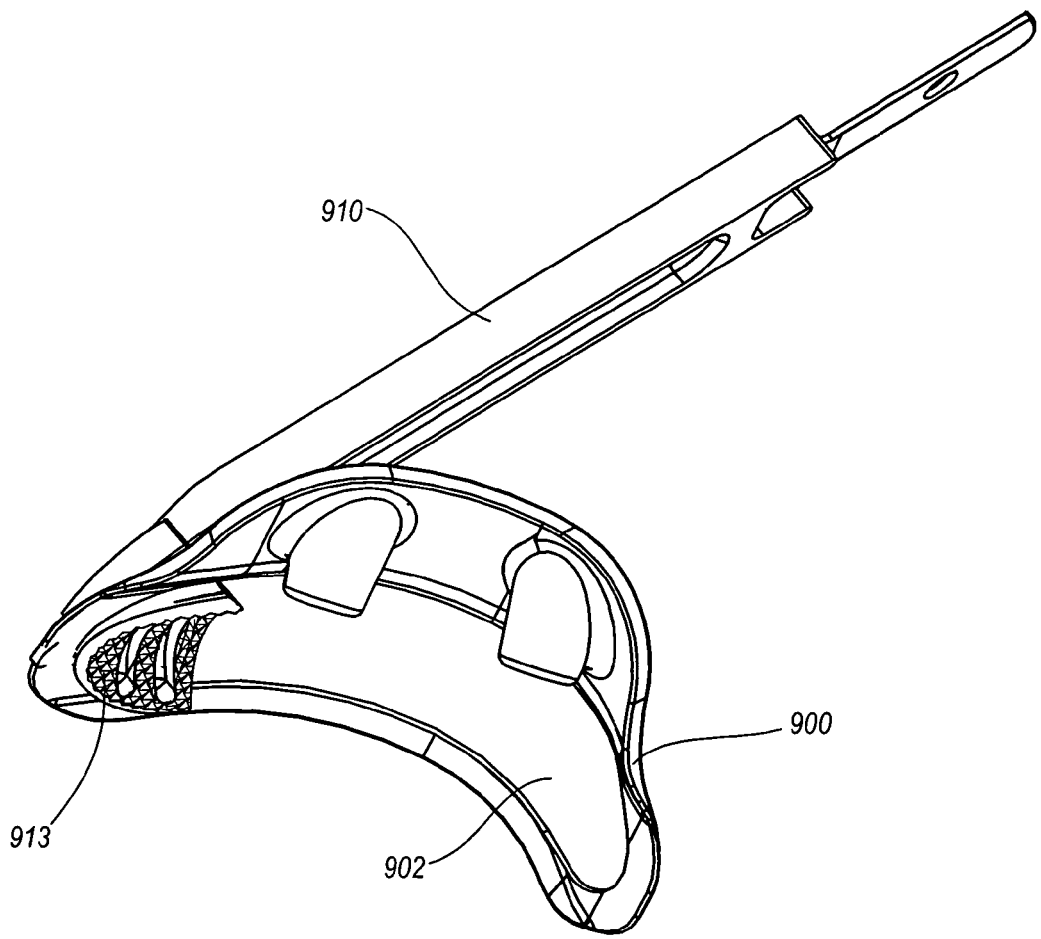
FIG. 47 is a perspective view of the rasp shown in FIG. 46 being used with the guide template of FIG. 45.

As depicted in FIGS. 46 and 47, a rasp 910 can be used to form rounded ends for the recessed pocket. Rasp 910 comprises an elongated handle 912 having a cutting mount 913 mounted on the end thereof. Cutting mount 913 has a generally semi-circular transverse cross section with a concave bearing face 914. Formed on bearing face 914 are a plurality of cutting teeth 915. Extending through cutting mount are a plurality of slots through which bone fragments can be removed. Cutting mount 913 is configured to be reciprocally moved within the opposing ends of opening 902 of guide template 900 so as to form rounded ends on the pocket formed to receive the implant.

Figure 48:
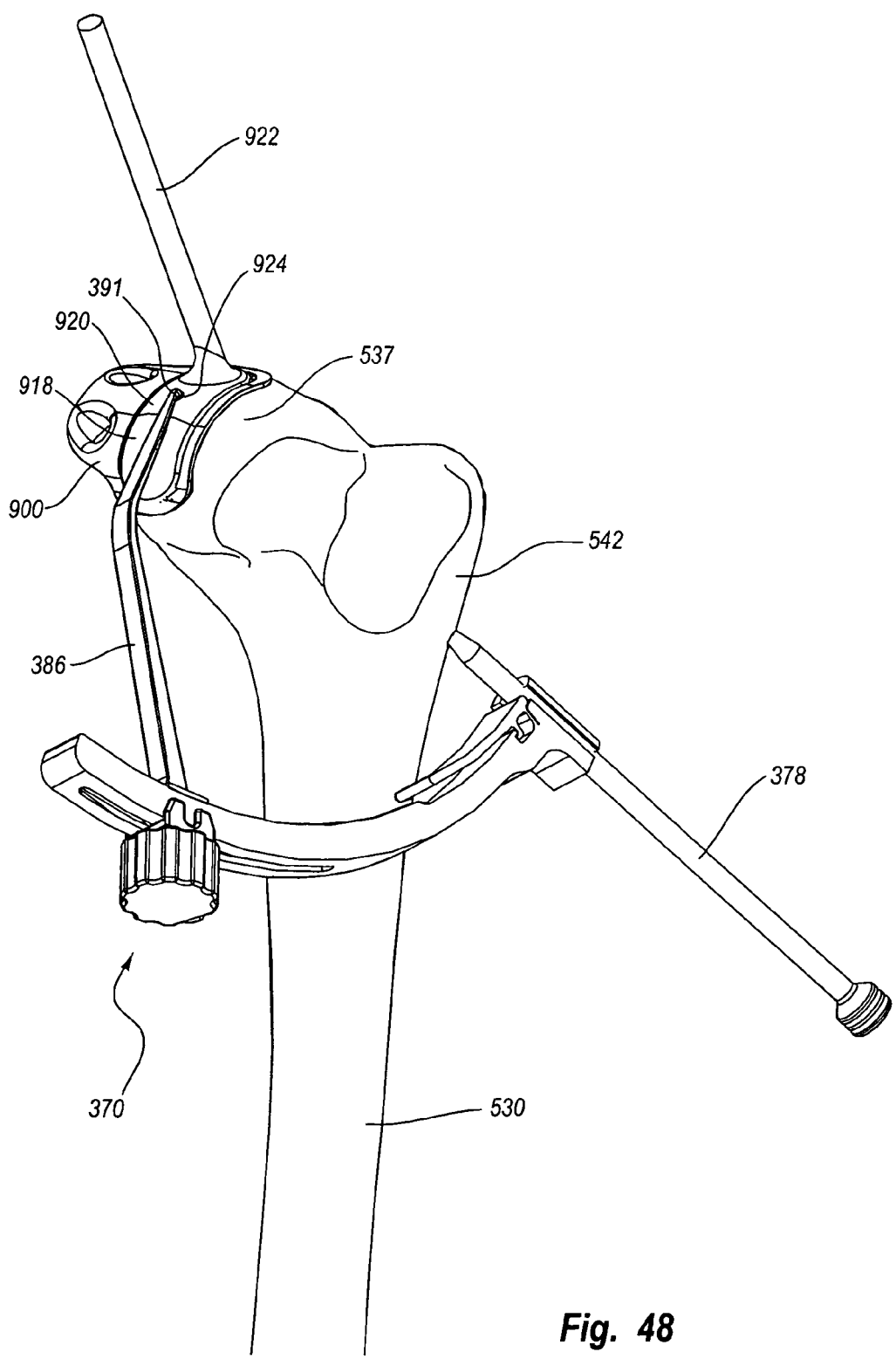
FIG. 48 is a perspective view of the femur shown in FIG. 45 with a centering template mounted on the guide template and a tunneling guide seated on the centering template.

Once the recessed pocket is finished, a centering template 918 is mounted within the recessed pocket that is still bounded by guide template 900. As depicted in FIG. 48, centering template 918 comprises a mounting plate 920 having a handle 922 projecting therefrom. Mounting plate 920 has substantially the same size and contouring as opening 902 of guide template 900. As such, mounting plate 920 is substantially fixed when received within opening 902. Formed on an upper surface of mounting plate 920 is a centering indent 924. When mounting plate 920 is positioned within opening 902, indent 924 is located above the location where tunnel 400 is to enter the recessed pocket formed on medial condyle 547.

Once centering template 918 is positioned, tunnel guide 370 (as previously discussed with regard to FIGS. 20 and 21) is mounted on femur 530 to facilitate the formation of tunnel 400. Specifically, tip 391 of alignment arm 386 is positioned on indent 924 of centering template 918 while guide sleeve 378 is biased against lateral side 542 of femur 530. Again, guide sleeve 378 can be positioned at any optimal location on femur 530 for the formation of tunnel 400. After the tunnel guide 370 is positioned, a guide wire and/or other drilling structures used to form tunnel 400 through femur 530 using guide sleeve 378 as a guide. This is substantially the same process as previously discussed with regard to FIG. 21.

In one alternative embodiment, centering template 918 and tunnel guide 370 can be eliminated. That is, tunnel 400 can be drilled starting at the recessed pocket and extending to the lateral or medial side of the femur. Because it is less critical where tunnel exits on the lateral or medial side, tunnel guide 370 is not required but could, if desired, still be used. This process could also be used on the tibial side.

Figure 49:
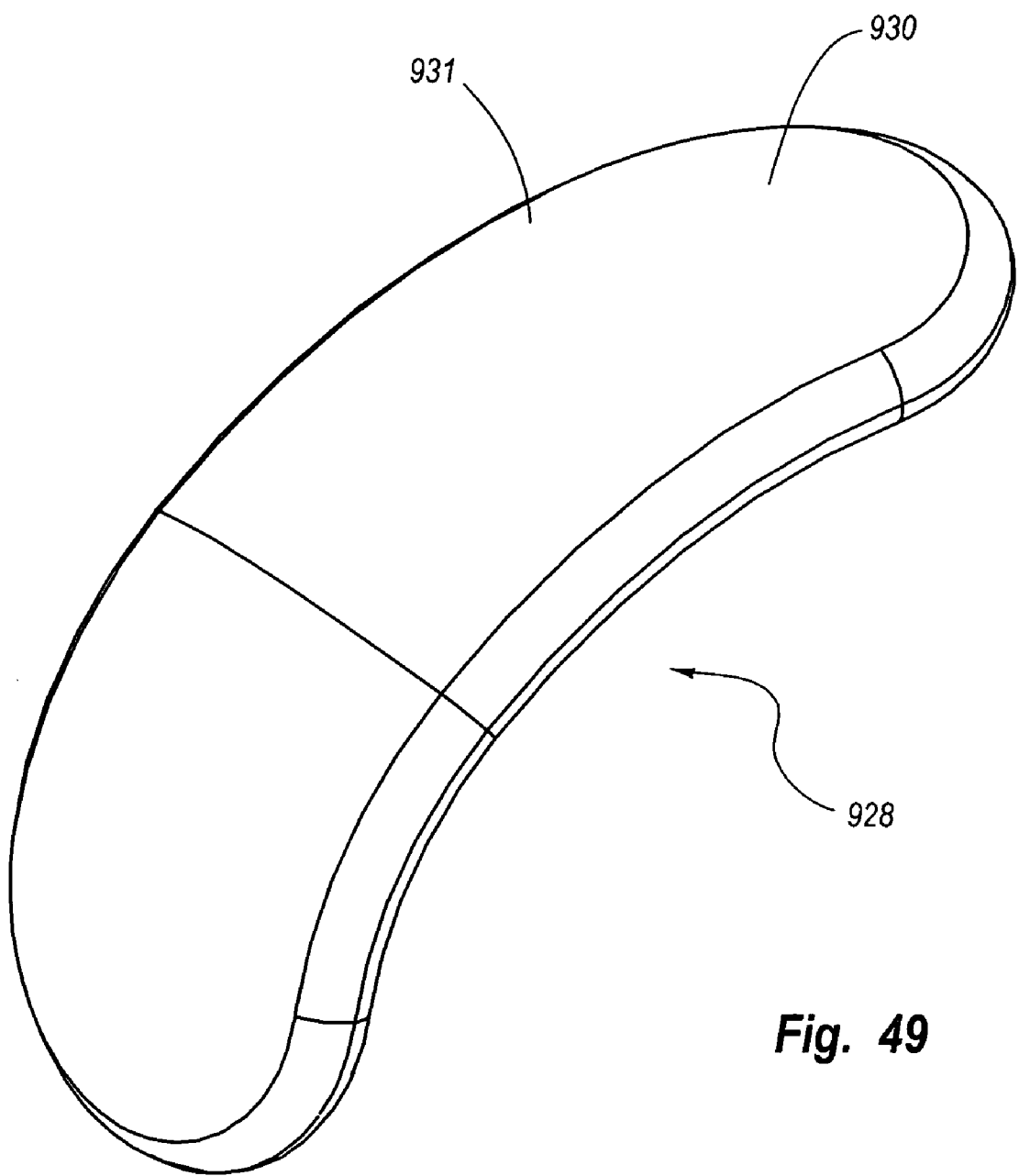
FIG. 49 is a top perspective view of a femoral condylar implant.
Figure 50:
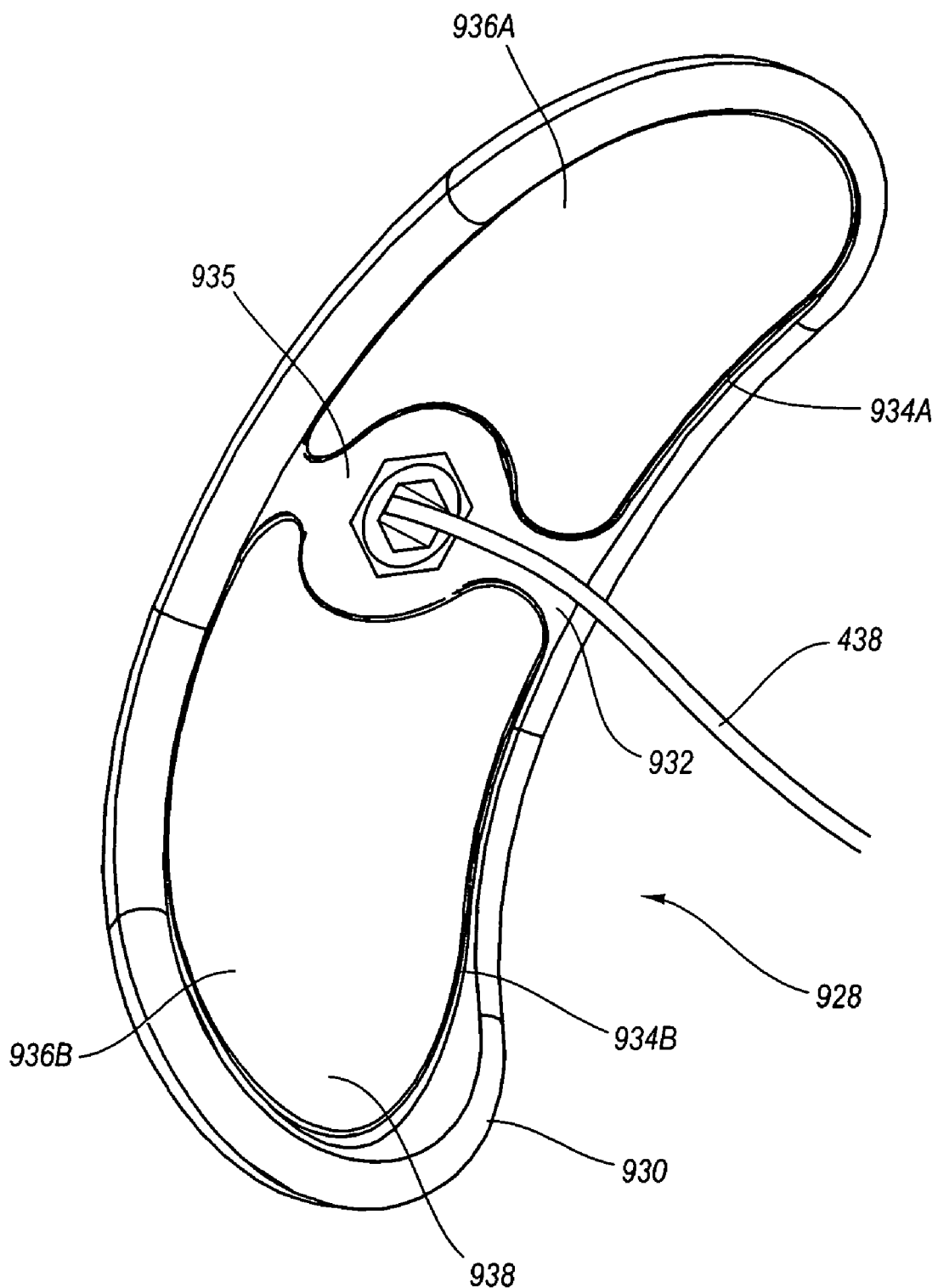
FIG. 50 is a bottom perspective view of the femoral condylar implant shown in FIG. 49 having a line connected thereto.

Once tunnel 400 is formed, tunnel guide 370, centering template 918, and guide template 900 are removed from femur 530. A femoral condylar implant 928 is then positioned within the recessed pocket. As depicted in FIGS. 49 and 50, in one embodiment femoral condylar implant 928 comprises a body 930 having a curved aticular surface 931 and an opposing bottom surface 932. A pair of pockets 934 A and are formed on bottom surface 932 and are separated by a bridge 935. Disposed within each pocket 934A and B is an inlay 936A and B of porous bone ingrowth material. Bridge 935 and inlays 936A and B substantially comprise a bone apposition surface 938. Bone apposition surface has a configuration complementary to the formation of the recessed pocket formed on medial condyle 537. Connected to bridge 935 is line 438. It is appreciated that the various alternatives as previously discussed with regard to the tibial condylar implants and the methods for connecting line 438 thereto are also applicable to femoral condylar implant 928.

Figure 51:
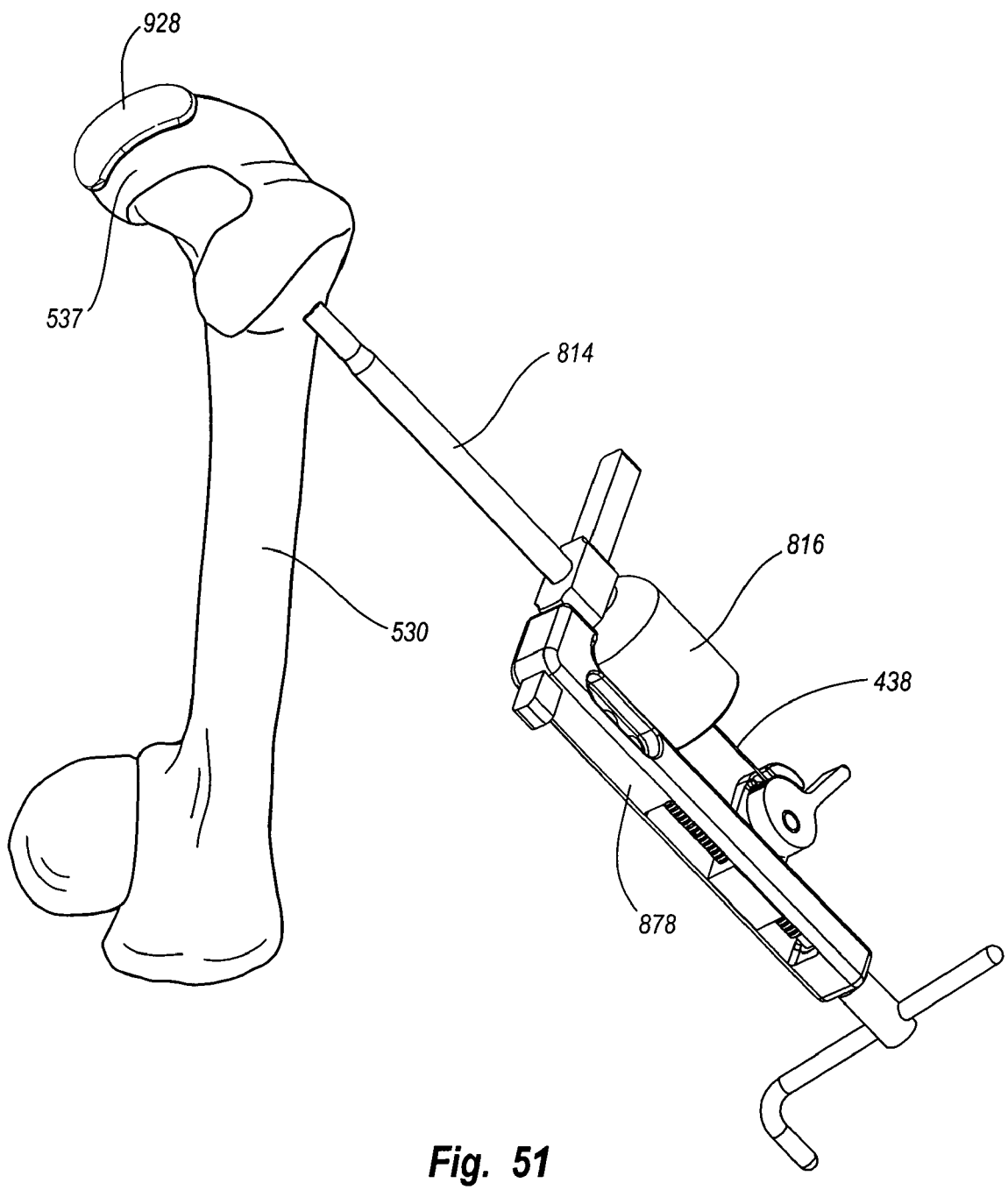
FIG. 51 is a perspective view of the system shown in FIG. 42 being used to secure the femoral condylar implant of FIG. 49 to the femur.

Finally, turning to FIG. 51, femoral condylar implant 928 is secured to femur 530 using anchor assembly 810 (FIG. 35) and the instruments and techniques as previously discussed with regard to FIGS. 34-43. The same alternatives as previously discussed with regard to FIGS. 34-43 are also applicable to the attachment of femoral condylar implant 928. For example, two separate tunnels can be formed on femur 530 that intersect with the recessed pocket on medial condyle 537. Opposing ends of a single line 438 slidably connected to implant 928 can be passed through the separate tunnels and secured with corresponding bone anchors. Alternatively, two separate and discrete lines 438 can be connected to femoral condylar implant 928, each line being disposed in a separate tunnel.

The present invention can also be used in mounting a total femoral implant. For example, depicted in FIG. 52, the articulation surface at distal end 532 of femur 530, notably the femoral medial condyle and lateral condyle, have been resected so as to form a resected articulation surface 534. Tunnel 90 is formed on femur 530. Second end 96 of tunnel 90 extends through resected articulation surface 534 while first end 94 of tunnel 90 is formed on medial side 540 at a location spaced apart from resected articulation surface 534. Tunnel 90 can be bored through femur 530 at an oblique angle α, as reflected in FIG. 30. In one embodiment the angle α is in a range between about 15° to about 50° with about 20° to about 40° being more common. Other angles can also be used. Tunnel 90 can be bored by making an incision in the skin adjacent femur 530, properly orienting a tubular alignment guide, then boring tunnel 90 with a drill through the alignment guide. In one embodiment tunnel 90 can be formed using a modified guide assembly similar to guide assembly 30 as previously discussed. Tunnel 90 can also be formed using the same types of methods and tools used to form tunnel 400.

Figure 53:
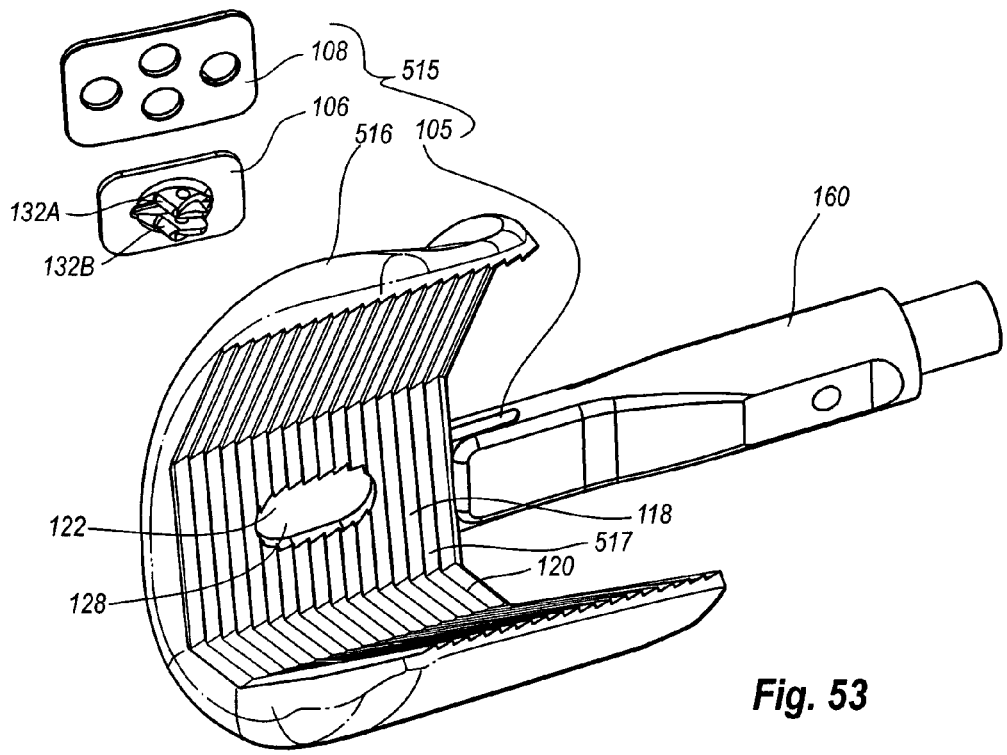
FIG. 53 is a perspective view of a femoral rasp assembly for resecting the distal end of a femur.

Resected articulation surface 534 can be formed using the present invention or other conventional resecting techniques. For example, depicted in FIG. 53 is a femoral rasp assembly 515 which has components similar to rasp assembly 100 previously discussed with regard to FIGS. 6-9. Femoral rasp assembly 515 comprises a substantially U-shaped rasp body 516, pivot arm 105, rasp guide 106, and cover plate 108.

Insertion handle 160 is show removably disposed over pivot arm 105 and, if desired, can be used to initially place rasp assembly 515 on femur 530. Rasp body 516 has a substantially concave cutting surface 517 having a plurality of ridges 118 formed thereon. Ridges 118 each terminate at sharpened cutting edge 120. It is appreciated that ridges 118 and cutting edges 120 can be at any desired orientation or combination of different orientations that facilitate cutting.

As with rasp assembly 100, extending through rasp body 516 is guide slot 122 and opening 128. Rasp guide 106 is received within guide slot 122 so that forks 132A-B pass through opening 128. Cover plate 108 secures rasp guide 106 within guide slot 122.

During operation, rasp assembly 515 is mounted on the distal end of femur 530 such that forks 132A and B of rasp guide 106 are aligned with second end 96 of tunnel 90. Once rasp assembly 515 is positioned, retention rod 102 (FIGS. 8 and 9) is advance within tunnel 90 from first end 94 and connected to rasp guide 106 as previously discussed.

Once retention rod 102 is secured to rasp assembly 515, insertion handle 160 is removed and a reciprocal driver, such as a reciprocal saw, is connected pivot arm 105. While holding rasp guide 106 substantially stationary by holding onto retention rod 102, the reciprocal driver rapidly reciprocates rasp body 516 so that cutting edges 120 resects the distal end of femur 530. In the embodiment depicted, rasp body 516 is only designed to resect the medial side of the distal end of femur 530. A complementary rasp assembly can then be used to resect the lateral side of the distal end of femur 530 using a second tunnel 90 extending through lateral side 542 of femur 530, thereby forming resected articulation surface 534.

Figure 54:
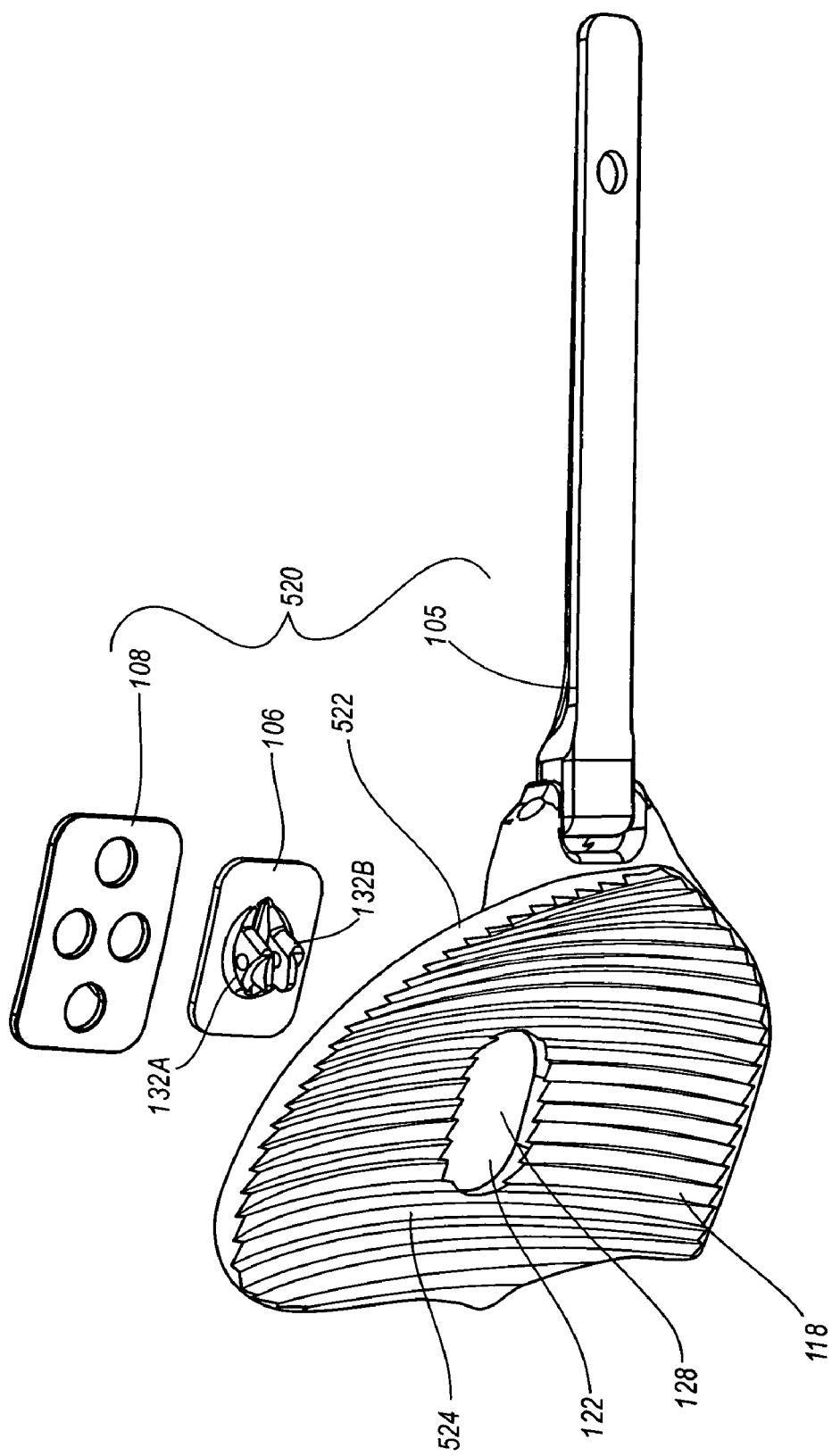
FIG. 54 is a perspective view of an alternative embodiment of a femoral rasp assembly for resecting the distal end of a femur.

In yet other embodiments, it is appreciated that multiple different rasp assemblies with one or more different tunnels can be used to resect femur 530 or a single rasp assembly can be configured to simultaneously resect the entire distal end of femur 530. For example, depicted in FIG. 54 is another embodiment of a femoral rasp assembly 520. Rasp assembly 520 comprises an arched rasp body 522, pivot arm 105, rasp guide 106, and cover plate 108. Rasp body 522 has a substantially concave cutting surface 524 having a plurality of ridges 118 formed thereon. As with rasp body 516, extending through rasp body 522 is guide slot 122 and opening 128. Rasp guide 106 is received within guide slot 122 so that forks 132A-B pass through opening 128. Cover plate 108 secures rasp guide 106 within guide slot 122.

Rasp body 522 is configured to primarily resect the anterior surface at the distal end of femur 530. As such, a corresponding tunnel 90 can be used on femur 530 to ensure proper placement of rasp body 522 during resection. A complementary rasp body is then be used to resect the remainder of the distal end of femur 530. For example, depicted in FIGS. 58-64 are alternative embodiments of two piece femoral implants. Corresponding two piece rasp bodies can be formed to resect the corresponding surfaces that receive the pieces of the femoral implants.

Furthermore, it is also appreciated that although resected articulation surface 534 is shown having a plurality of planar faces, in alternative embodiments the one or more rasp assemblies can be configured so as to produce resected articulation surface 534 having a continuous smooth arched surface or combinations of different surfaces.

In other embodiments, it is appreciated that the various rasps can be used without the formation of tunnels or the use of retention rods. That is, the rasps can simply be biased against the bone. Likewise, by using guides similar to guide 214 depicted in FIG. 12, an oscillating or reciprocating saw can be used to form the resected surfaces depicted in FIG. 52. In yet other embodiments, a combination of sawing and rasping can be used to form the desired resected surface.

Figure 52:
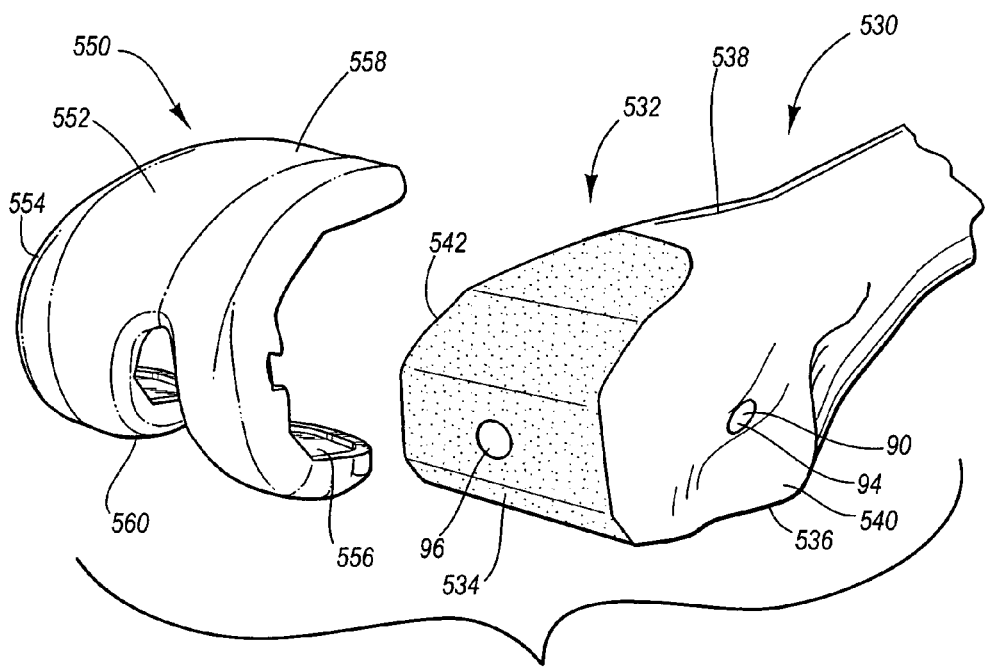
FIG. 52 is a perspective view of an inventive femoral implant for mounting on the distal end of a resected femur.
Figure 55:
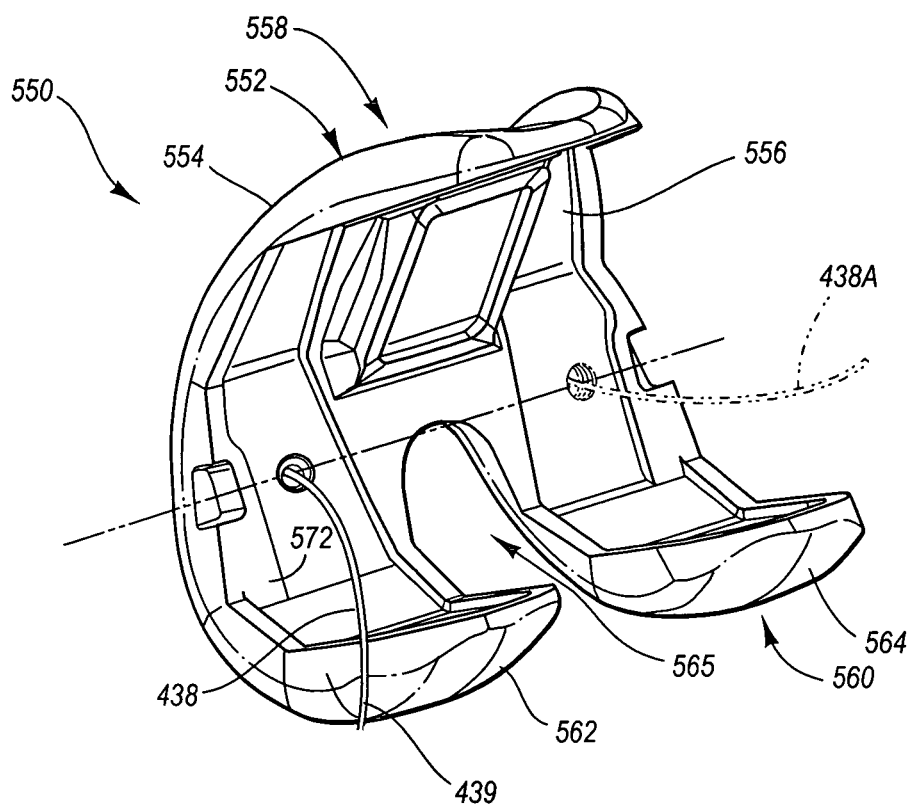
FIG. 55 is an inside perspective view of the femoral implant shown in FIG. 52.

In one embodiment of the present invention, a femoral implant 550 is provided incorporating features of the present invention. As depicted in FIGS. 52 and 55, femoral implant 550 comprises a substantially U-shaped body 552 having an articular surface 554 and an opposing bone apposition surface 556 which each extend between an anterior end 558 and a posterior end 560. Articular surface 554 is configured to mate with a tibia or tibial implant while bone apposition surface 556 is configured to mate with resected articulation surface 534 of femur 530.

Figure 56:
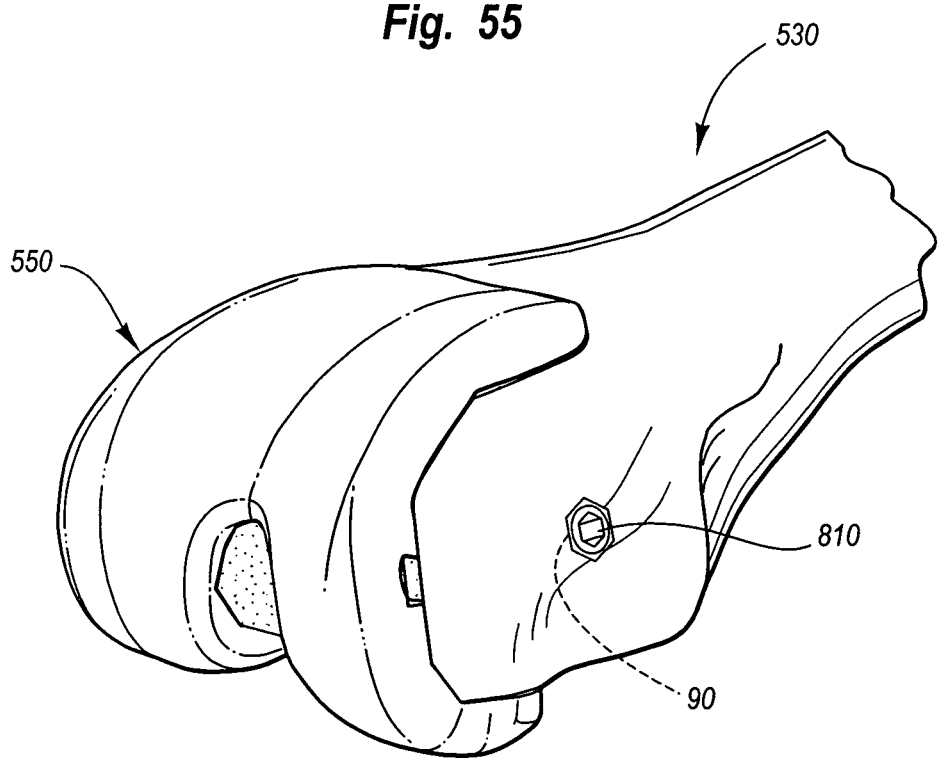
FIG. 56 is a perspective view of the femoral implant shown in FIG. 55 mounted to the femur shown in FIG. 52.

More specifically, body 552 of femoral implant 550 comprises a substantially U-shaped medial condyle 562 and a substantially U-shaped lateral condyle 564. Condyles 562 and 564 are connected together at anterior end 558 but are spaced apart at posterior end 560 so that an elongated slot 565 is formed thereat. Mounted to femoral implant 550 so as to project from bone apposition surface 556 of medial condyle 562 is line 438. During use, first end 439 of line 438 is passed through tunnel 90 from second end 96 to first end 94. Femoral implant 550 is then positioned on resected articulation surface 534 so that the position where line 438 connects with femoral implant 550 is aligned with second end 96 of tunnel 90. Here it is appreciated that because there are no posts projecting from bone apposition surface 556, femoral implant 550 can be slide on to resected articulation surface 534 lateral to medial or medial to lateral through a medial or lateral incision on the knee of the patent. As a result, it is not necessary to openly expose distal end 532 of femur 530 during placement of femoral implant 550. As depicted in FIG. 56, once femoral implant 550 is positioned, anchor assembly 810 or alternatives thereto, is used to secure femoral implant 550 to femur 530.

In one alternative embodiment depicted in FIG. 55, a second line 438A can connected to femoral implant 550 so as to project from bone apposition surface 556 of lateral condyle 564. By passing second line 438A through a second tunnel on the lateral side of femur 530, a second anchor assembly can be used to further secure femoral implant 550 to femur 530. Alternatively, second line 438A and the second anchor assembly may be used instead of the first line 438 and corresponding anchor assembly 810. In yet another alternative, a single line 438 can be slidably mounted to femoral implant 550 with opposing ends of the line being secured within separate tunnels.

Figure 57:
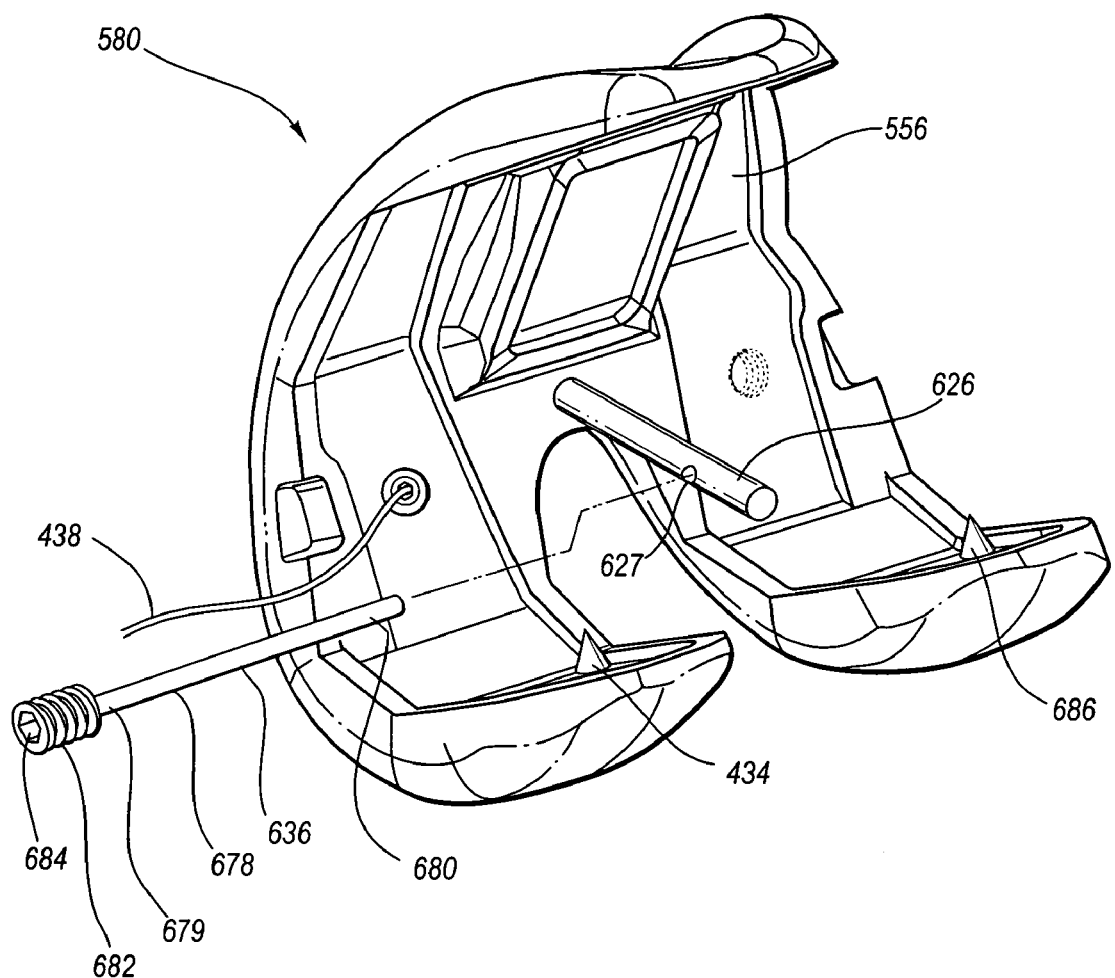
FIG. 57 is a perspective view of an alternative embodiment of the femoral implant.

Depicted in FIG. 57 is an alternative embodiment of a femoral implant 580 incorporating features of the present invention. Again, like elements of different embodiments are identified by like reference characters. In contrast to bone apposition surface 556 being substantially flat, an elongated post 626 is formed projecting from bone apposition surface 556. An opening 627 extends through the side of post 626. An elongated pin 678 has a proximal end 679 and an opposing distal end 680. An enlarged threaded head 682 is formed at proximal end 679. A polygonal socket 684 is formed on an end face of head 682 to receive a driver. A first bore is formed on resected surface 534 (FIG. 52) of femur 530 to receive post 626. Either before or after femoral implant 580 is positioned on resected surface 534 with line 438 extending through tunnel 90, a second bore is formed into or through femur 530 lateral to medial or medial to lateral so that the second bore is aligned with opening 627 in post 626. Pin 678 is then advanced into the second bore so that pin 678 passes through opening 627 of post 626. Pin 678 is then secured in place by screwing threaded head 682 of post 626 into the femur. Post 262 thus helps to prevent any unwanted movement of femoral implant 580. As also depicted in FIG. 57, spikes 686 project from bone apposition surface 556. It is appreciated that any number of spikes, fins, or other forms of projections can be formed on bone apposition surface 556 and can be used in conjunction with or independent of post 626.

In one embodiment, in addition to using anchor assembly 810 to attach the femoral implant to the femur 530, a bone cement can be employed to further enhance the adhesion of the femoral implant to resected femur 530. The bone cement can be applied before and/or during mounting of the femoral implant. For example, the femoral implant can be partially attached and then a syringe or other form of delivery tube used to inject bone cement between the femoral implant and femur 530. In addition, a porous or fibrous material, such as a wire mesh, may be attached to bone apposition surface 556 of the femoral implant to thereby foster bone growth between the femoral implant and resected femur 530 and/or to provide surface area for attaching the bone cement between the femoral implant and resected femur 530. In one embodiment, one or more pockets can be formed on bone apposition surface 556. An inlay of porous bone ingrowth material, such as previously discussed with regard to inlay 320, can be secured within the pockets.

Depicted in FIGS. 58-64 are connectible two-piece femoral implants incorporating features of the present invention. The implants can be used in knee arthroplasty wherein the two parts are independently slid in from the medial or lateral side of the knee through an incision and then connected and mounted onto resected articulation surface 534 of femur 530. A coupling member, such as a bolt, screw, pin, or the like, can be used to attach one part of the femoral implant to the other. Optionally, one part may be mounted on resected articulation surface 534 followed by the other part being connected thereto. One or more lines 438 connected to the femoral implant is used in conjunction with a corresponding anchor assembly 810 or alternative thereof, as discussed above, to connect the femoral implant to femur 530. Because the smaller parts of the two-piece femoral implant can be sequentially inserted through an incision, the required incision can be smaller than required for unitary implants.

Figure 58:
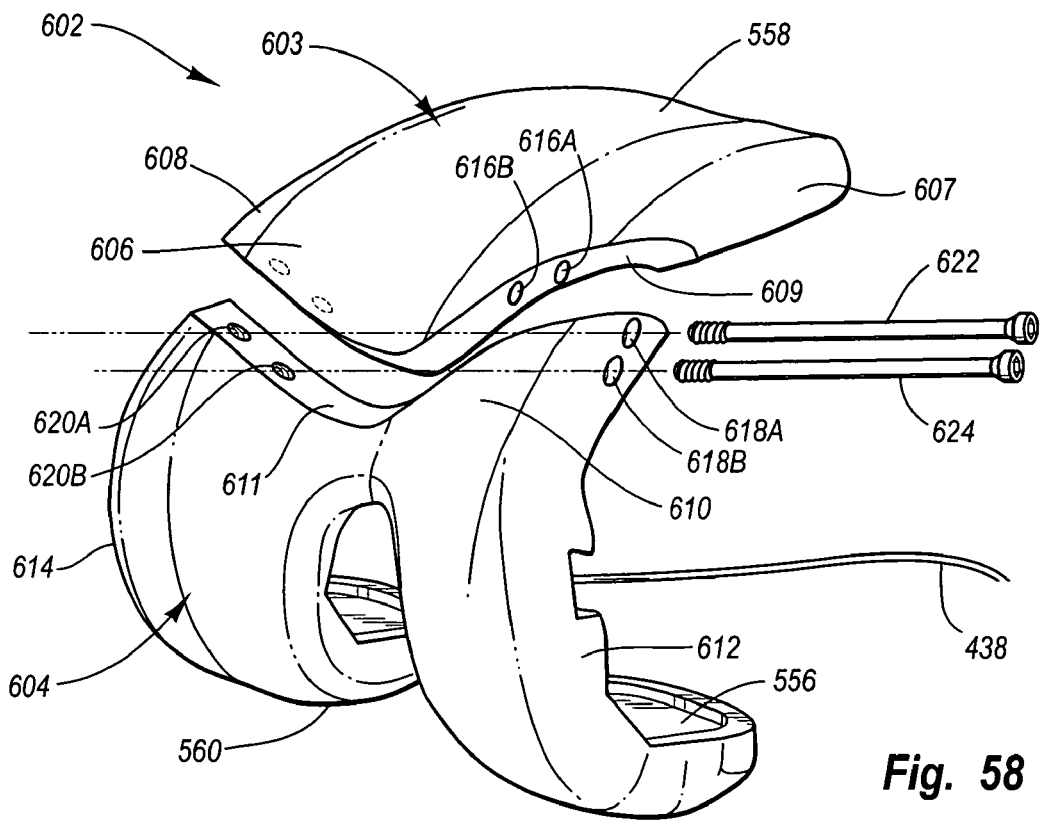
FIG. 58 is a perspective view of a laterally bisected, two-piece femoral implant in a disassemble state.
Figure 59:
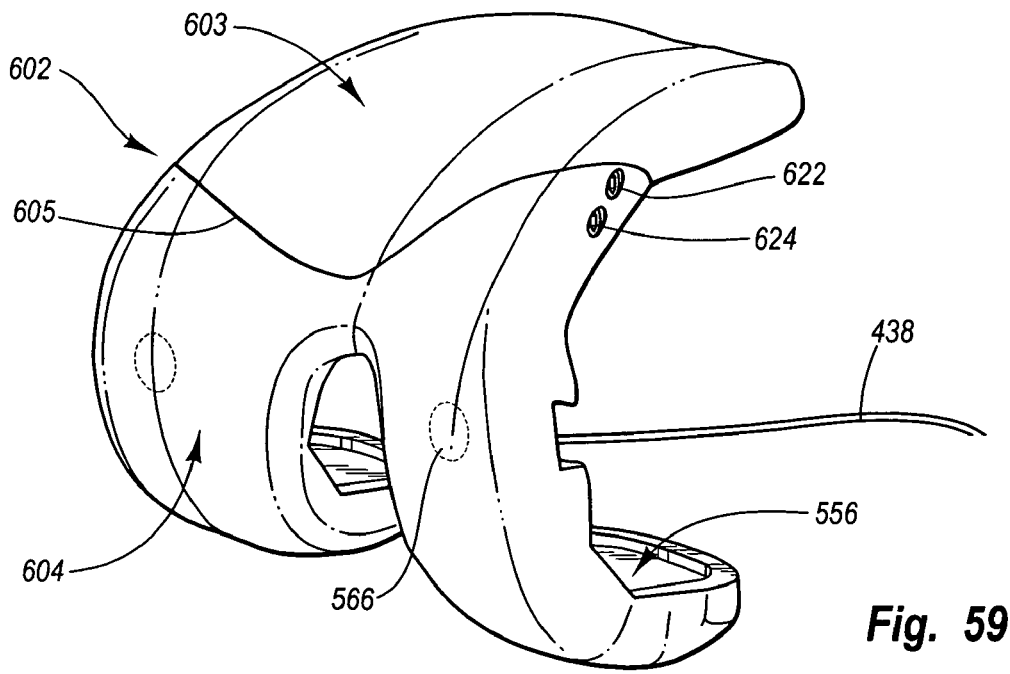
FIG. 59 is a perspective view of the implant shown in FIG. 58 in an assembled state.

FIG. 58 is a perspective view of a two-piece femoral implant 602 in a divided state while FIG. 59 is a perspective view of femoral implant 602 shown in an assembled state. In one embodiment, femoral implant 602 can be designated as "end use" in that the entire structure is configured to be permanently mounted onto the resected articulation surface during a resurfacing procedure and is designed for permanent daily use by a patient.

Femoral implant 602 is centrally divided lateral to medial and comprises a patellar condyle 603, which includes anterior end 558, and a tibial condyle 604, which includes posterior end 560. Patellar condyle 603 includes at a substantially V-shaped posterior end 606. Posterior end 606 terminates at an end face 609 that extends between a medial side 607 and a lateral side 608 of patellar condyle 603. A pair of spaced apart linear passageways 616A-B transversely extend through posterior end 606 of patellar condyle 603 so as to enter and exit through end face 609.

Tibial condyle 604 terminates at a V-notched anterior end 610 that is complementary to V-shaped posterior end 606 of patellar condyle 603. Anterior end 610 terminates at an end face 611 that also extends between a medial side 612 and lateral side 614 of tibial condyle 604. A pair of spaced apart passageways 618A-B transversely extend through anterior end 610 of tibial condyle 604 between medial side 612 and end face 611. A pair of threaded sockets 620A-B are formed on end face 611 toward lateral side 614 in alignment with passageways 618A-B.

When patellar condyle 603 and tibial condyle 604 are mated, a joint line 605 is formed at the intersection. In one embodiment, joint line 605 is positioned so that it corresponds to the location of the sulcus of femur 530 when femoral implant 602 is mounted on femur 530. In the mated position, passageways 616A-B, passageways 618A-B, and sockets 620A-B are aligned. As a results, bolts 622 and 624 having threaded ends can be passed through passageways 616A-B, 618A-B and screwed into sockets 620A-B so as to securely connect patellar condyle 603 and tibial condyle 604. It is appreciated that bolts 622 and 624 can be replaced with a variety of other structures to connect patellar condyle 603 and tibial condyle 604.

Femoral implant 602 further comprises line 438 connected to patellar condyle 603 and/or tibial condyle 604. Again, by extending the one or more lines 438 though a corresponding tunnel on the femur, anchor assembly 810 or an alternative thereto can be used to secure the lines 438 and thus femoral implant 602 to femur 530 as discussed in the above embodiments.

Figure 60:
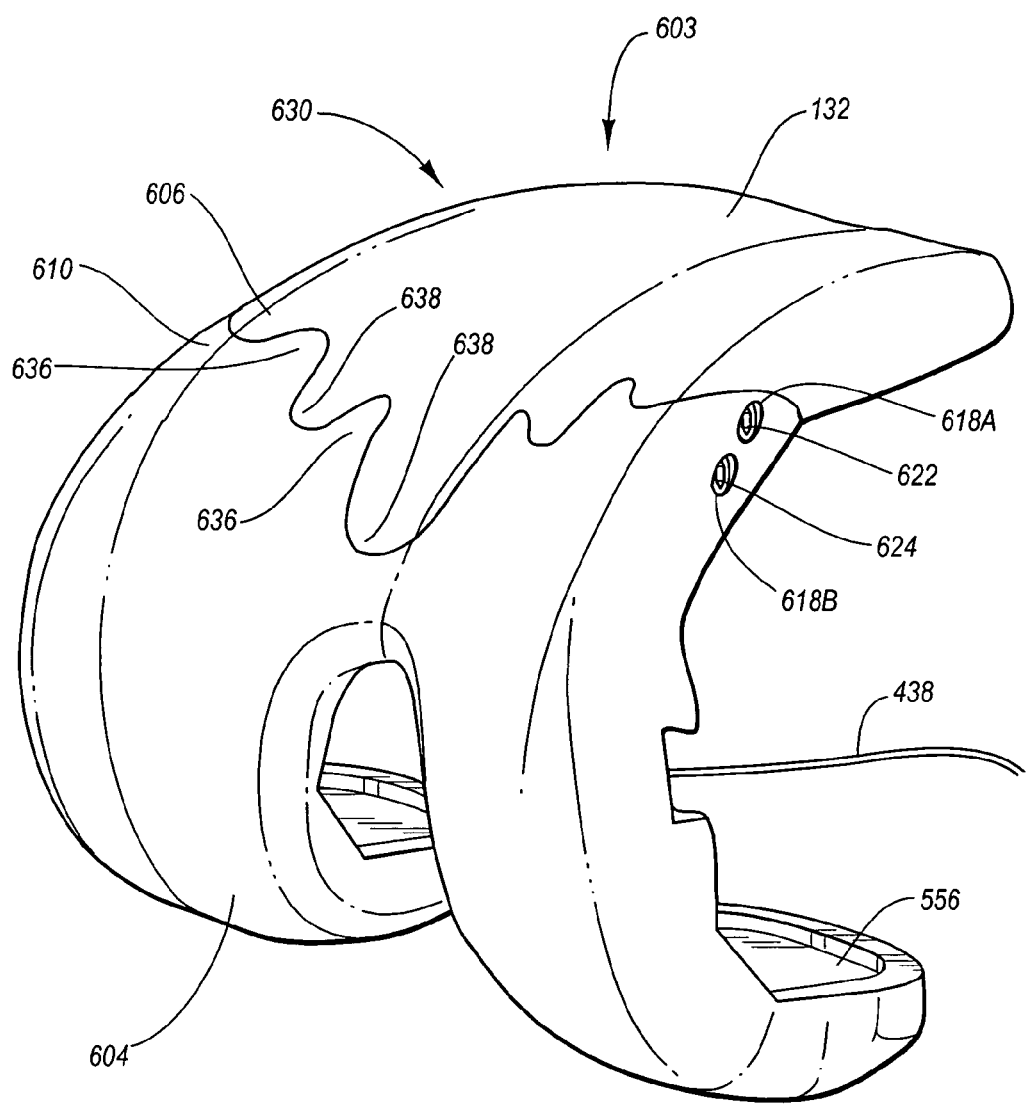
FIG. 60 is a perspective view of an alternative embodiment of the implant shown in FIGS. 58 and 59.

Depicted in FIG. 60 is a femoral implant 630 that is substantially the same as femoral implant 602. The only difference is that interlocking teeth 636 and 638 are formed along posterior end 606 of patellar condyle 603 and anterior end 610 of tibial condyle 604, respectively. Interlocking teeth 636 and 638 provide greater engagement and stability between patellar condyle 603 and tibial condyle 604.

Figure 61:
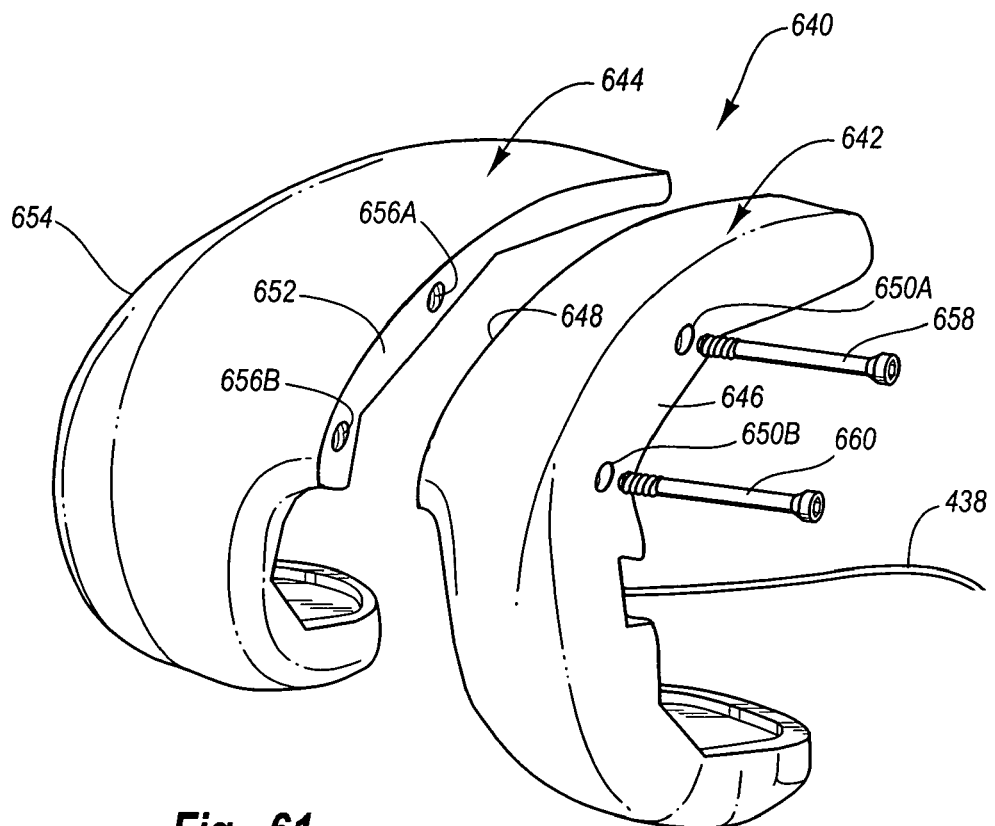
FIG. 61 is a perspective view of a longitudinally bisected, two-piece femoral implant in a disassemble state.
Figure 62:
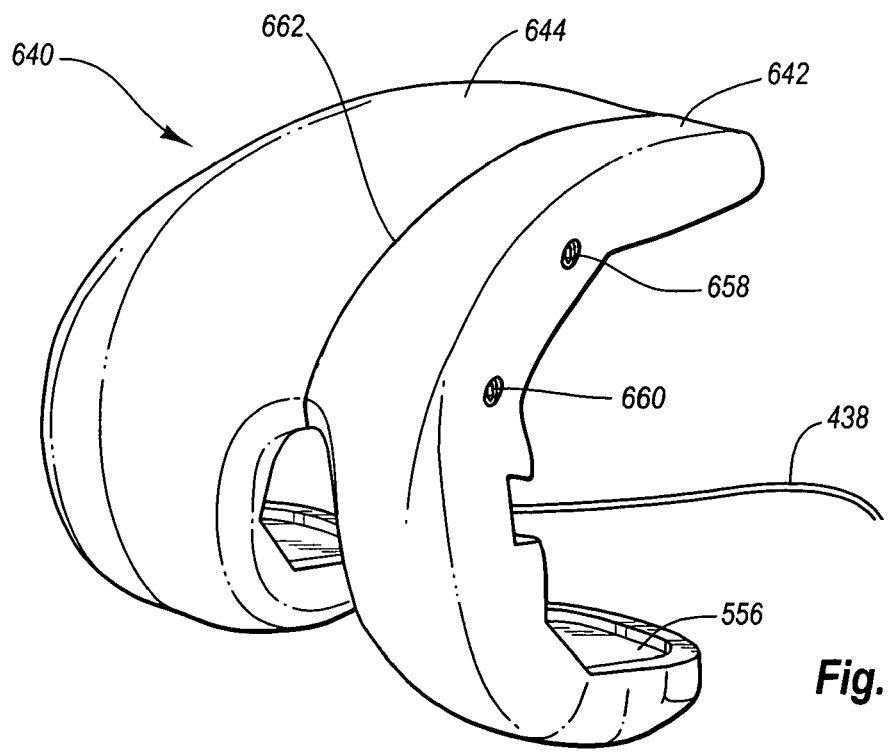
FIG. 62 is a perspective view of the implant shown in FIG. 61 in an assembled state.

Depicted in FIGS. 61 and 62 is another alternative embodiment a two-piece femoral implant 640. Femoral implant 640 is centrally divided anterior to posterior so as to comprise a substantially U-shaped medial condyle 642 a substantially U-shaped lateral condyle 644. Medial condyle 642 has a medial side face 646 and a lateral side face 648. A pair of spaced apart passageways 650A-B transversely extend through medial condyle 642 between side faces 646 and 648.

Lateral condyle 644 also has a medial side face 652 and a lateral side face 654. A pair of spaced apart threaded sockets 656A-B are formed on medial face 652 of lateral condyle 644. When condyles 642 and 644 are mated, a joint line 662 is formed at the intersection. In one embodiment, joint line 662 is positioned so that it corresponds to the location of the trochlear groove of femur 530 when femoral implant 640 is mounted on femur 530. In the mated position, passageways 650A-B are aligned with threaded sockets 656A-B. As a result, fasteners 658 and 660 each having a threaded end can be selectively passed through passageways 650A-B and screwed into sockets 656A-B so as to secure condyles 642 and 644 together. Again, line 438 is mounted to medial condyle 642 and/or lateral condyle 644 to facilitate attachment of femoral implant 640 to femur 530.

Figure 63:
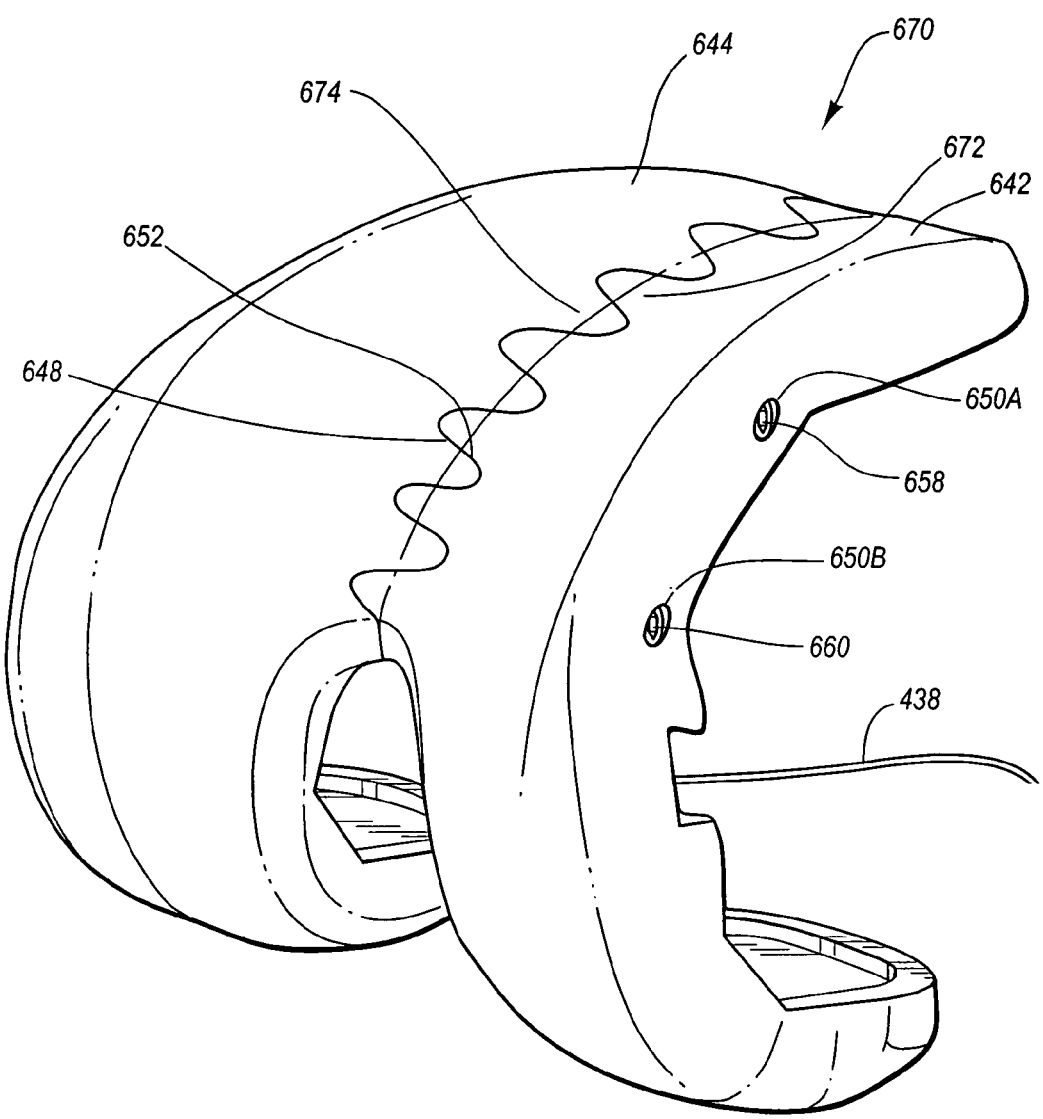
FIG. 63 is a perspective view of an alternative embodiment of the implant shown in FIGS. 61 and 62.
Figure 64A:
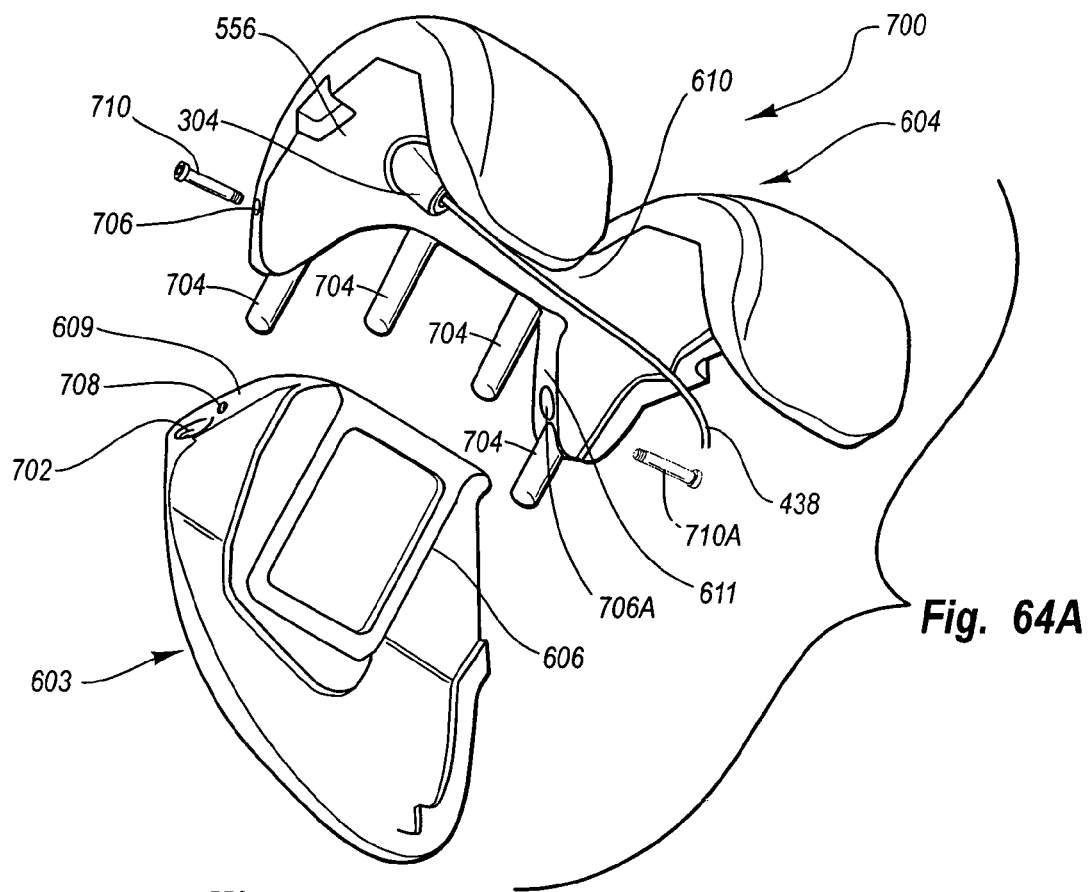
FIGS. 64A-D are perspective views of another alternative embodiment of a laterally bisected, two-piece femoral implant.
Figure 64B:
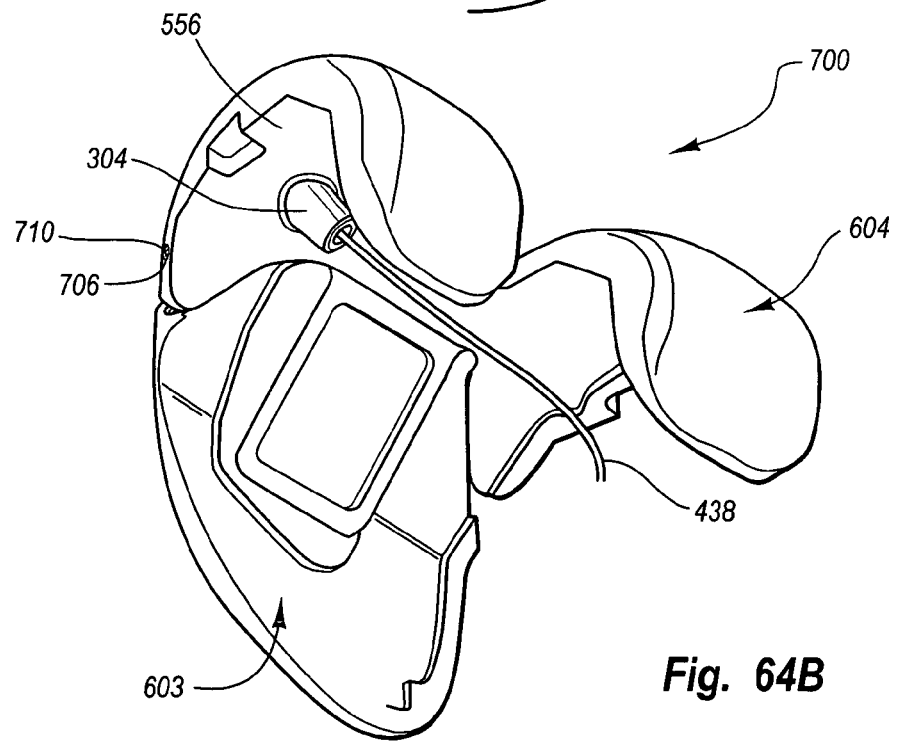
Figure 64C:
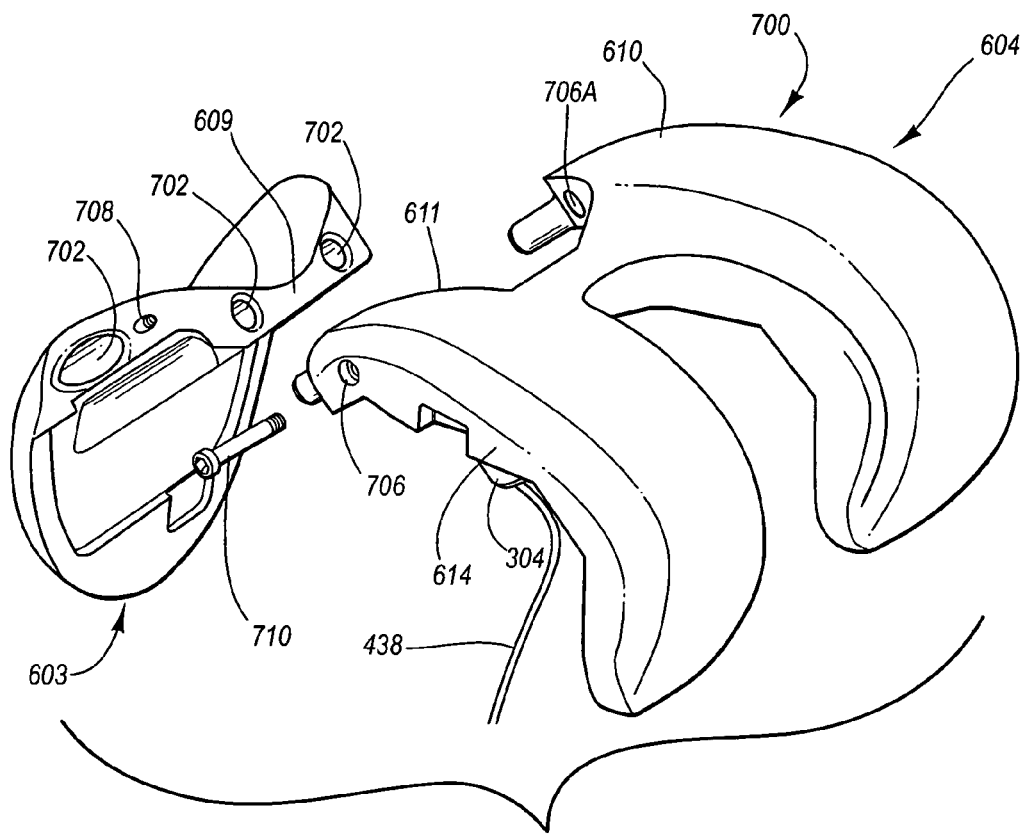
Figure 64D:
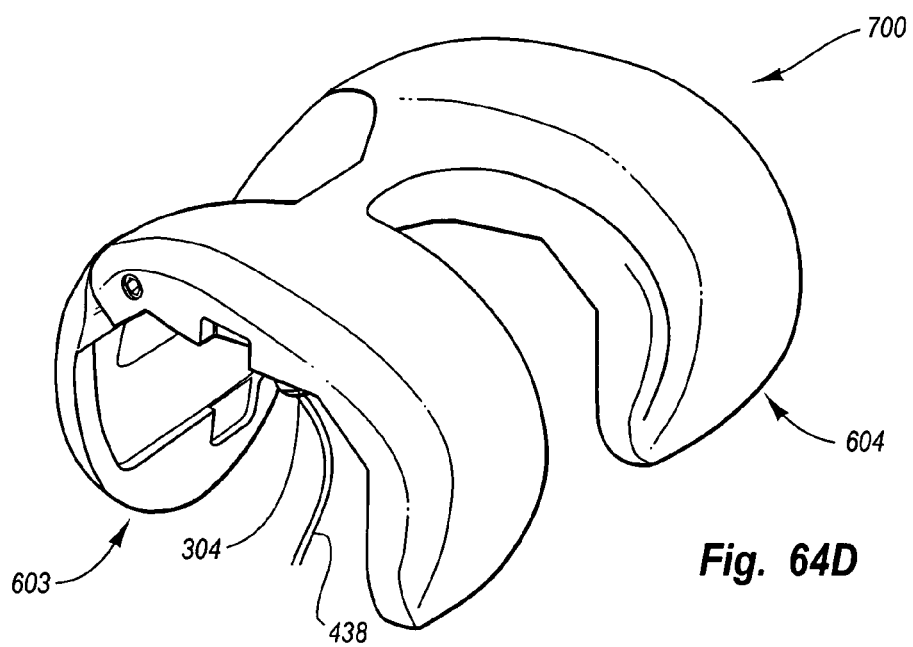

Depicted in FIG. 63 is a femoral implant 670 that is substantially the same as femoral implant 640. The only difference is that a plurality of interlocking teeth 672 and 674 are formed along lateral side face 648 of medial condyle 642 and medial side face 652 of lateral condyle 644, respectively. Interlocking teeth 672 and 674 provide greater engagement and stability between medial condyle 642 and lateral condyle 644.

Depicted in FIGS. 64A-D is another embodiment of a two-piece femoral implant 700 incorporating features of the present invention. Femoral implant 700 is substantially similar to implant 602 discussed above with regard to FIGS. 58 and 59. As such, like elements are identified by like reference characters. In contrast to implant 602, a plurality of spaced apart holes 702 are formed on end face 609 of posterior end 606 of patellar condyle 603. A plurality of spaced apart pegs 704 project from end face 611 of anterior end 610 of tibial condyle 604. Pegs 704 are formed complementary to holes 702 such that when patellar condyle 603 and tibial condyle 604 are mated together, pegs 704 are received within holes 702 so as to rigidly hold condyles 603 and 604 together.

In contrast to having a pair of bolts transversely extending across patellar condyle 603 in femoral implant 602, femoral implant 700 comprises a passageway 706 that extends from lateral side 614 of tibial condyle 604 to end face 611 at anterior end 610 of tibial condyle 604. A threaded socket 708 is formed on end face 609 of posterior end 606 of patellar condyle 603. When condyles 603 and 604 are mated, passageway 706 and socket 708 are aligned. A bolt 710 having a threaded end is passed through passageway 706 and screwed into socket 708 so as to secure condyles 603 and 604 together. In one alternative, a complementary passageway 706A and socket 708A can also be formed on the medial side of condyles 603 and 604 to provide further engagement by a bolt 710A.

Although not required, in the embodiment depicted line 438 is shown connected to a stem projecting from bone apposition surface 556. Alternatively, one or more lines 438 can connect directly to bone apposition surface 556.

Figure 65:
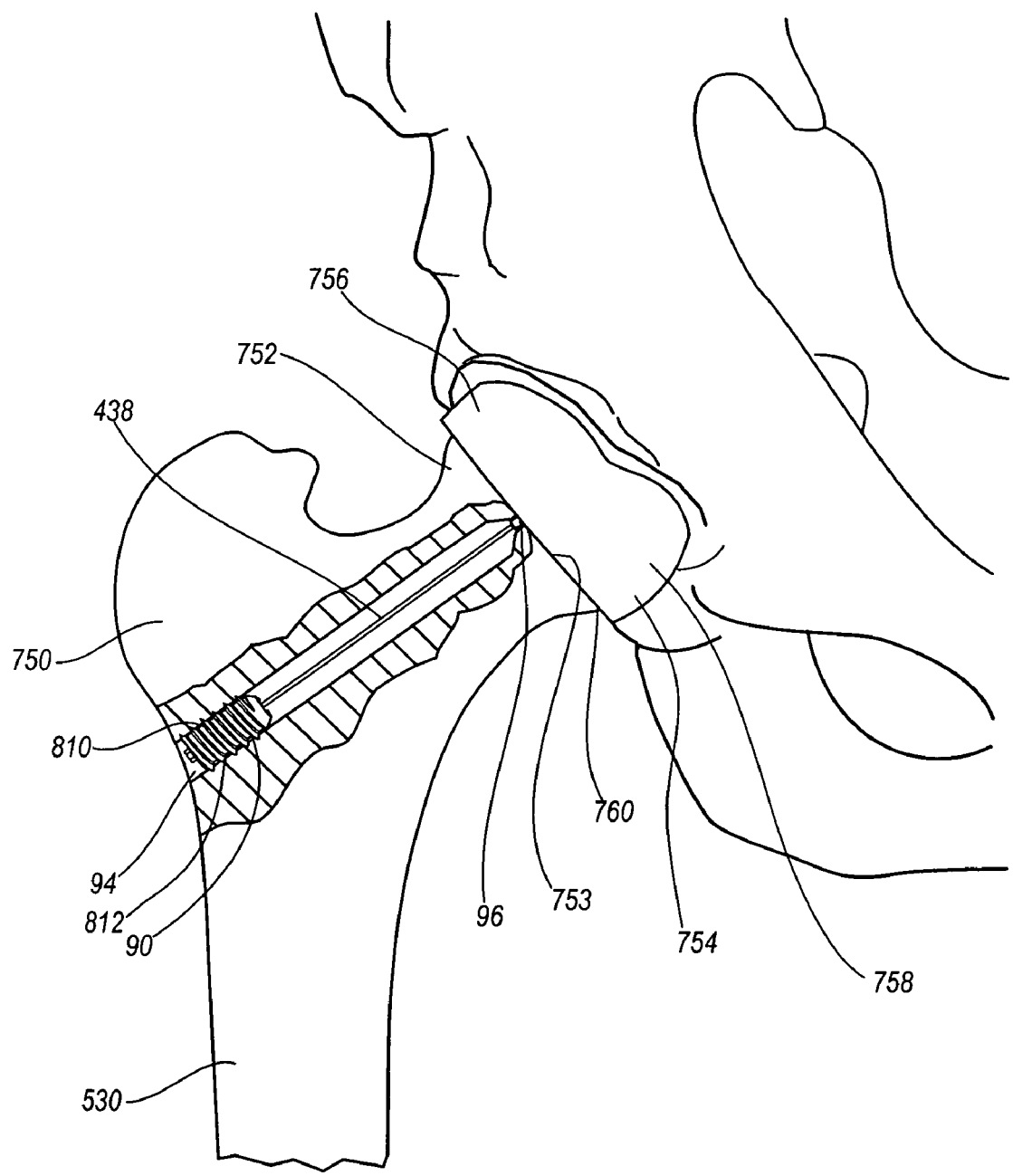
FIG. 65 is a partial cross sectional side view of an inventive implant mounted on the proximal end of a femur.
Figure 66:
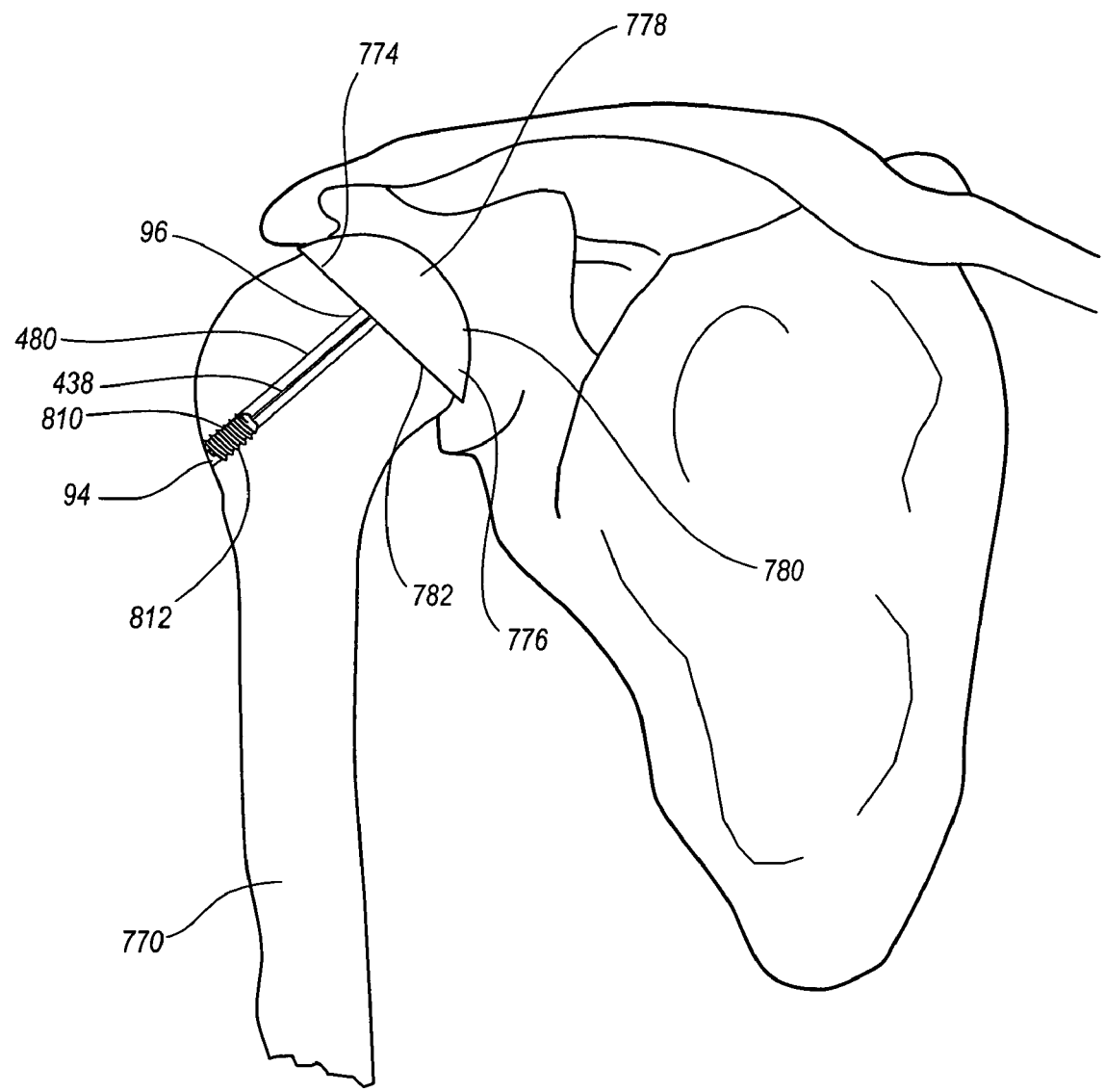
FIG. 66 is a partial cross sectional side view of an inventive implant mounted on the proximal end of a humerus.
Figure 67:
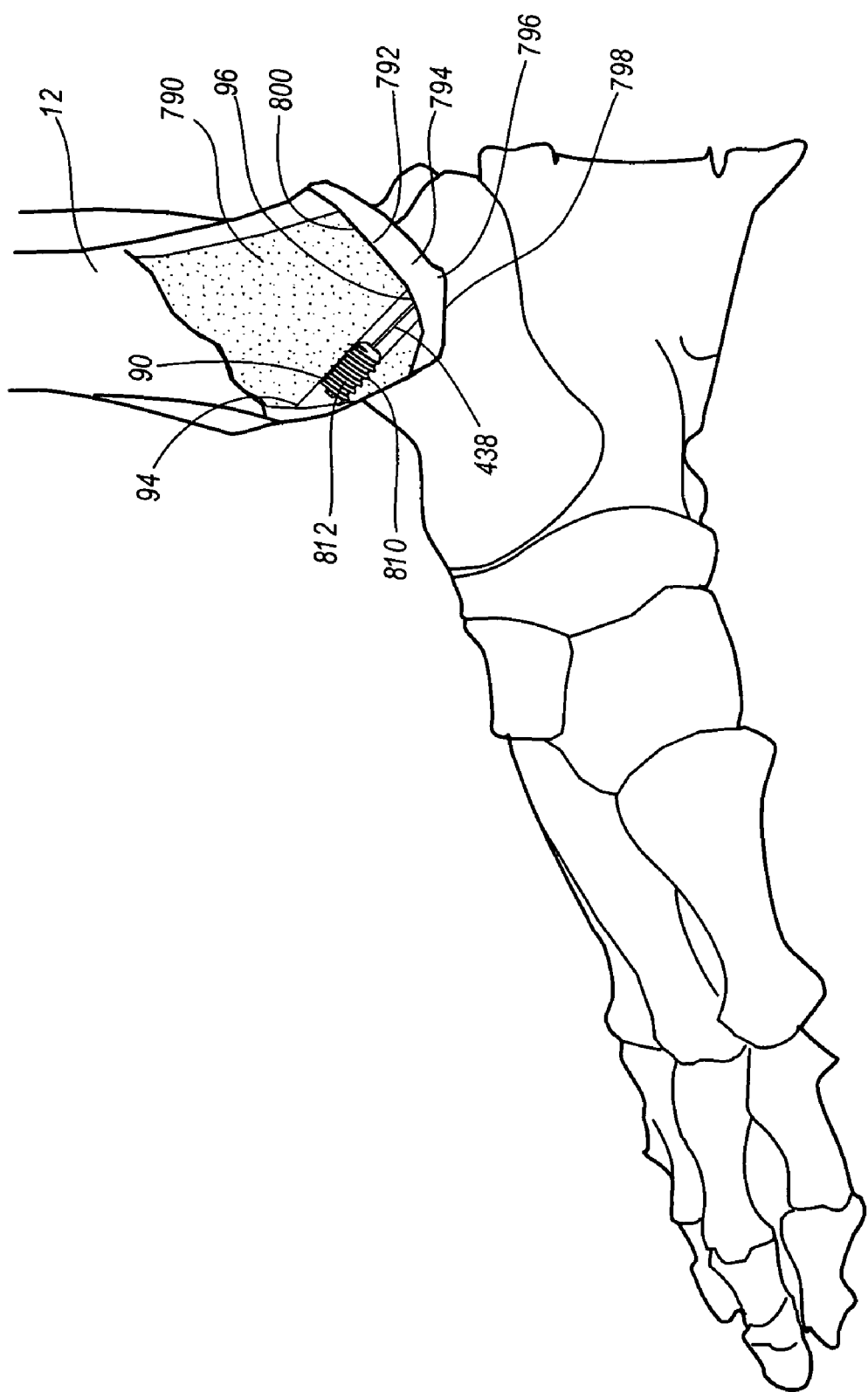
FIG. 67 is a partial cross sectional side view of an inventive implant mounted on the distal end of a tibia.

Depicted in FIGS. 65-67 are still other examples of inventive implants mounted on resected articulation surfaces of other orthopedic joints. For example, depicted in FIG. 65 is femur 530 having a proximal end 750 that would normally terminate at a femoral head 752 having an articulation surface. In the depicted drawing, femoral head 752 has been resected to from a resected articulation surface 753. In each of the embodiments depicted in FIGS. 65-67, it is appreciated that the resected articulation surface can be formed using conventional techniques or by using a modified version of one or more of the methods disclosed herein in combination with forming a tunnel.

A proximal femoral implant 754 is shown mounted on resected articulation surface 753. Implant 754 comprises a body 756 having an articular surface 758 and an opposing bone apposition surface 760. Articular surface 758 engages with the acetabular socket while bone apposition surface 760 biases against resected articulation surface 753.

Tunnel 90 is formed on femur 530 using any desired technique. Second end 96 of tunnel 90 is formed on resected articulation surface 753 while first end 94 of tunnel 90 is formed on the shaft of femur 530 at a location spaced apart from resected articulation surface 753. A line 438 is mounted to implant 754 and projects from bone apposition surface 760. Line 438 is passed through tunnel 90 and is secured therein using anchor assembly 810 or an alternative thereto. Anchor assembly 810 and line 438 thus combine to secure implant 754 to femur 530.

Depicted in FIG. 66 is a humerus 770 having a proximal end 772 that would normally terminate at a humerus head having an articulation surface. In the depicted drawing, the humerus head has been resected to form a resected articulation surface 774. A proximal humerus implant 776 is shown mounted on resected articulation surface 774. Implant 776 comprises a body 778 having an articular surface 780 and an opposing bone apposition surface 782. Articular surface 780 engages with the scapula while bone apposition surface 782 biases against resected articulation surface 774.

Tunnel 90 is formed on humerus 770. Second end 96 of tunnel 90 is formed on resected articulation surface 774 while first end 94 of tunnel 90 is formed on the shaft of humerus 770 at a location spaced apart from resected articulation surface 774. A line 438 is connected to implant 776 so as to project from bone apposition surface 782 of implant 776. Anchor assembly 810 is disposed within tunnel 90 and is coupled with implant 776 through line 438 so as to secure implant 776 to humerus 770.

Depicted in FIG. 67 is tibia 12 having a distal end 790 that would normally terminate at an articulation surface such as the inferior articular surface and the malleolar articular surface. In the depicted drawing, distal end 790 of tibia 12 has been resected to form a resected articulation surface 792. A distal tibial implant 794 is shown mounted to resected articulation surface 792. Implant 794 comprises a body 796 having an articular surface 798 and an opposing bone apposition surface 800. Articular surface 798 engages with the talus or an implant thereat while bone apposition surface 800 biases against resected articulation surface 792.

Tunnel 90 is formed on tibia 12. Second end 96 of tunnel 90 is formed on resected articulation surface 798 while first end 94 of tunnel 90 is formed on tibia 12 at a location proximally spaced apart from resected articulation surface 792. Line 438 is connected to implant 794 so as to project from bone apposition surface 800. Line 438 is disposed within tunnel 90 and connected to anchor assembly 810 so as to secure implant 794 to tibia 12.

Set forth above are several different embodiments of the present invention. It is appreciated that the different features of the different embodiments can be mixed and matched to produce a variety of other embodiments within the scope of the present invention. By way of example and not by limitation, each of the different implants can be made with or without an inlay of porous bone ingrowth material on the bone apposition surface; each different implant can have one or more different lines that are connected in one or more different ways; and each different implant can be made as an integral body or two or more separate parts. For example, each implant can comprise a metal tray that is mounted to the bone and a plastic bearing plate that is mounted to the tray. It is likewise appreciated that the different methods steps for the different embodiments can also be mixed and matched and used with other techniques. Finally, it is again noted that the implants described herein are only by way of example and not by limitation. The present invention can also be used in association with resurfacing articulation surfaces of other orthopedic joints.

Finally, the above embodiments primarily discuss mounting implants on resected articulation surfaces. On occasion, however, a sufficient portion of a natural articulation surface has been worn down or otherwise removed by events other than surgical resection so that it is not necessary to resect the wear surface which is still functioning as a natural articulation surface. On these occasions, it is envisioned that the implant can be mounted directly on the worn natural articulation surface with minimal or no surgical resection of the articulation surface.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method comprising:
   passing a first end of a flexible line through a channel in a bone anchor and through a channel of a first driver removably coupled in a force transferring relationship with the bone anchor to drive the bone anchor;
   removably coupling a portion of the line passed through the first driver to a line tensioner by attaching the line to a line attachment point movably disposed on the line tensioner;
   removably coupling the line tensioner with the first driver;
   moving the line attachment point with respect to the line tensioner to apply a tensioning force to the line;
   advancing a collet into the bone anchor while the tensioning force is maintained on the line, the collet at least partially encircling the line and having a plurality of flexible arms that radially, inwardly constrict to engage the line when the collet is advanced into the bone anchor; and
   after the step including applying tensioning force to the line, decoupling the first driver from the bone anchor.

2. A method as recited in claim 1, wherein the first driver is a tubular member, the channel thereof extending along a central longitudinal axis thereof.

3. A method as recited in claim 1, further comprising removably coupling a second driver to the collet, the second driver having a channel through which the line extends.

4. A method as recited in claim 3, wherein at least a portion of the second driver is disposed within the channel of the first driver.

5. A method as recited in claim 1, wherein the collet is at least partially disposed within the channel of the bone anchor prior to passing the proximal end of the flexible line through the channel in the bone anchor.

6. A method as recited in claim 1, wherein the collet is positioned within the channel of the bone anchor after the proximal end of the flexible line is passed through the channel in the bone anchor.

7. A method as recited in claim 1, further comprising securing a second end of the line to an implant.

8. A method as recited in claim 7, wherein the implant has a top articular surface and an opposing bone apposition surface, the implant being configured to replace a portion of an articulation surface of a joint of a patient.

9. A method as recited in claim 1, further comprising slidably connecting an implant to the line at a location between the first end of the line and an opposing second end of the line.

10. A method as recited in claim 1, wherein advancing the collet into the bone anchor comprises screwing the collet into the bone anchor.

11. A method for mounting an implant at an orthopedic joint, the method comprising the acts of:
   forming a first tunnel through a bone, the first tunnel having an open second end on a natural or resected articulation surface of the bone and an open first end at a location on the bone spaced apart from the natural or resected articulation surface;
   passing a first end of a flexible first line through the first tunnel, the first line being connected to an implant having a bone apposition surface;
   positioning the bone apposition surface of the implant over the natural or resected articulation surface of the bone; and
   securing at least a portion of the first line within the first tunnel by:
      passing the first end of the first line through a channel in a bone anchor; and
      screwing the bone anchor into the tunnel so that one or more threads projecting from an exterior surface of the bone anchor engage with the bone bounding the first tunnel so as to secure the bone anchor within the first tunnel.

12. A method as recited in claim 11, wherein the act of forming the first tunnel comprises:
   biasing a tubular guide sleeve against the location on the bone that is spaced apart from the natural or resected articulating surface; and
   passing a drill tool through the guide sleeve and into the bone so that the drill tool exits the bone on the natural or resected articulating surface.

13. A method as recited in claim 11, wherein the act of forming the first tunnel through the bone comprises forming the tunnel through the proximal end or distal end of a femur, tibia, humerus, radius, or ulna.

14. A method as recited in claim 11, wherein the implant comprises a body having an articular surface and the opposing bone apposition surface, a stem projecting from the bone apposition surface, the method further comprising positioning the implant on the natural or resected articulating surface so that a least a portion of the stem is received within the second end of the first tunnel.

15. A method as recited in claim 14, further comprising advancing a cross pin through the bone and into an opening formed on a side of the stem.

16. A method as recited in claim 11, wherein the implant comprises a top articular surface.

17. A method as recited in claim 11, further comprising mounting an articular surface to the implant.

18. A method as recited in claim 11, further comprising securing a portion of the first line within the channel of the bone anchor.

19. A method as recited in claim 18, wherein securing the portion of the first line within the channel of the bone anchor comprises positioning or manipulating a lock at least partially disposed within the channel of the bone anchor so that the first line is secured within the bone anchor.

20. A method as recited in claim 18, further comprising:
   passing the first end of the first line through a collet; and
   the act of securing the portion of the first line within the channel of the bone anchor comprises advancing the collet into the channel of the bone anchor, the collet having a plurality of flexible arms that radially, inwardly constrict to engage the first line when the collet is advanced into the bone anchor.

21. A method as recited in claim 20, further comprising tensioning the first line extending between the implant and the bone anchor prior to advancing the collet into the channel of the bone anchor.

22. A method as recited in claim 20, further comprising severing the first line proximal of the bone anchor after the collet is advanced into the channel of the bone anchor.

23. A method as recited in claim 18, further comprising backing the bone anchor back toward the first end of the first tunnel after securing a portion of the first line within the channel of the bone anchor.

24. A method as recited in claim 11, further comprising:
   forming a second tunnel through the bone, the second tunnel having an open second end on a natural or resected articulation surface of the bone and an open first end at a location on the bone spaced apart from the natural or resected articulation surface; and
   positioning a second end of the first line within the second tunnel, the implant being slidably mounted on the first line between the first end and the opposing second end.

25. A method as recited in claim 24, further comprising securing the second end of the first line to the bone.

26. A method as recited in claim 11, further comprising:
   forming a second tunnel through the bone, the second tunnel having an open second end on a natural or resected articulation surface of the bone and an open first end at a location on the bone spaced apart from the natural or resected articulation surface; and
   passing a flexible second line through the second tunnel, the second line being connected to the implant.

27. A method as recited in claim 26, further comprising securing at least a portion of the second line within the second tunnel.

* * * * *